United States Patent
Staudt et al.

(10) Patent No.: US 11,725,248 B2
(45) Date of Patent: Aug. 15, 2023

(54) EVALUATION OF MANTLE CELL LYMPHOMA AND METHODS RELATED THERETO

(71) Applicants: The United States of America, as represented by the Secretary, Department of Health and Human Services, Bethesda, MD (US); British Columbia Cancer Agency Branch, Vancouver (CA); Julius-Maximilians—University of Würzburg, Würzburg (DE); Oregon Health & Science University, Portland, OR (US); Hospital Clinic de Barcelona, Barcelona (ES); Universitat de Barcelona, Barcelona (ES); Oslo University Hospital HF, Oslo (NO); Board of Regents of the University of Nebraska, Lincoln, NE (US); The Cleveland Clinic Foundation, Cleveland, OH (US); Mayo Foundation for Medical Education and Research, Rochester, MN (US)

(72) Inventors: Louis M. Staudt, Bethesda, MD (US); David William Scott, Vancouver (CA); George W. Wright, Rockville, MD (US); Andreas Rosenwald, Wurzburg (DE); Pau Abrisqueta, Barcelona (ES); Rita Braziel, West Linn, OR (US); Elias Campo Guerri, Barcelona (ES); Wing C. Chan, Pasadena, CA (US); Joseph M. Connors, Vancouver (CA); Jan Delabie, Toronto (CA); Diego Villa, Vancouver (CA); Kai Fu, Omaha, NE (US); Randy D. Gascoyne, North Vancouver (CA); Timothy Greiner, Council Bluffs, IA (US); Elaine S. Jaffe, Great Falls, VA (US); Pedro Jares, Barcelona (ES); Anja Mottok, Vancouver (CA); German Ott, Bietigheim-Bissingen (DE); Lisa M. Rimsza, Scottsdale, AZ (US); Graham Slack, Richmond (CA); Dennis Weisenburger, Glendora, CA (US); Erlend B. Smeland, Oslo (NO); James Robert Cook, Shaker Heights, OH (US)

(73) Assignees: The United States of America, as represented by the Secretary, Department of Health and Human Services, Bethesda, MD (US); British Columbia Cancer Agency Branch, Vancouver (CA); Julius-Maximilians-University of Würzburg, Würzburg (DE); Oregon Health & Science University, Portland, OR (US); Hospital Clinic de Barcelona, Barcelona (ES); Universitat de Barcelona, Barcelona (ES); Oslo University Hospital HF, Oslo (NO); The Cleveland Clinic Foundation, Cleveland, OH (US); Mayo Foundation for Medical Education and Research, Rochester, MN (US)

(*) Notice: Subject to any disclaimer, the term of this patent is extended or adjusted under 35 U.S.C. 154(b) by 1304 days.

(21) Appl. No.: 16/094,965
(22) PCT Filed: Apr. 20, 2017
(86) PCT No.: PCT/US2017/028628
§ 371 (c)(1),
(2) Date: Oct. 19, 2018
(87) PCT Pub. No.: WO2017/184861
PCT Pub. Date: Oct. 26, 2017

(65) Prior Publication Data
US 2019/0153539 A1    May 23, 2019

Related U.S. Application Data
(60) Provisional application No. 62/325,213, filed on Apr. 20, 2016.

(51) Int. Cl.
*C12Q 1/6886*    (2018.01)
(52) U.S. Cl.
CPC ..... *C12Q 1/6886* (2013.01); *C12Q 2600/106* (2013.01); *C12Q 2600/118* (2013.01); *C12Q 2600/158* (2013.01)
(58) Field of Classification Search
CPC ............ C12Q 1/6886; C12Q 2600/118; C12Q 2600/158; C12Q 2600/106
See application file for complete search history.

(56) References Cited

U.S. PATENT DOCUMENTS

| 7,919,237 B2 | 4/2011 | Dimitrov et al. | |
| 2005/0164231 A1* | 7/2005 | Staudt ................... | G16B 40/20 435/6.16 |

(Continued)

FOREIGN PATENT DOCUMENTS

| WO | WO 2005/024043 A2 | 3/2005 |
| WO | WO 2008/013910 A2 | 1/2008 |

(Continued)

OTHER PUBLICATIONS

Kwak, M. etal; "Gene expression analysis in formalin fixed paraffin embedded melanomas is associated with density of corresponding immune cells in those tissues". Sci Rep 10, 18336 (2020), pp. 1-8 (Year: 2020).*

(Continued)

*Primary Examiner* — Karlheinz R. Skowronek
*Assistant Examiner* — Meredith Abbott Vassell
(74) *Attorney, Agent, or Firm* — Leydig, Voit & Mayer, Ltd.

(57) ABSTRACT

The present invention provides methods of determining a survival predictor score of a subject having mantle cell (Continued)

lymphoma (MCL). The present invention also provides methods of predicting the survival outcome of a subject having MCL and provides methods of selecting a treatment for a subject having MCL.

20 Claims, 18 Drawing Sheets

Specification includes a Sequence Listing.

(56) References Cited

U.S. PATENT DOCUMENTS

| | | | |
|---|---|---|---|
| 2007/0105136 | A1 | 5/2007 | Staudt et al. |
| 2009/0181393 | A1 | 7/2009 | Mulligan et al. |
| 2009/0233279 | A1 | 9/2009 | Glinskii |
| 2009/0253583 | A1 | 10/2009 | Yoganathan |
| 2011/0152115 | A1 | 6/2011 | Staudt et al. |
| 2012/0225432 | A1 | 9/2012 | Campo Guerri et al. |

FOREIGN PATENT DOCUMENTS

| | | |
|---|---|---|
| WO | WO 2009/149359 A2 | 12/2009 |
| WO | WO 2014/197936 A1 | 12/2014 |
| WO | WO 2015/069790 A1 | 5/2015 |
| WO | WO 2015/085172 A2 | 6/2015 |
| WO | WO 2016/057705 A1 | 4/2016 |
| WO | WO 2017/184861 A1 | 10/2017 |

OTHER PUBLICATIONS

Linton, K. et al; "Microarray Gene Expression Analysis of Fixed Archival Tissue Permits Molecular Classification and Identification of Potential Therapeutic Targets in Diffuse Large B-Cell Lymphoma", The Journal of Molecular Diagnostics, vol. 14, Issue 3, 2012, pp. 223-232 (Year: 2012).*

Vose, Julie M. "Mantle cell lymphoma: 2015 update on diagnosis, risk-stratification, and clinical management." American journal of hematology 90.8 (2015): 739-745 (Year: 2015).*

Hartmann, Elena M., German Ott, and Andreas Rosenwald. "Molecular outcome prediction in mantle cell lymphoma." (2009): 63-73 (Year: 2009).*

Alizadeh et al., "Distinct types of diffuse large B-cell lymphoma identified by gene expression profiling," Nature, 403 (6769), 503-511 (2000).

Argatoff et al., "Mantle cell lymphoma: A clinicopathologic study of 80 cases," Blood, 89 (6), 2067-2078 (1997).

Bomben et al., "701 Identification of a Novel Gene Expression Signature in Mantle Cell Lymphoma from the Fondazione Italiana Linfomi (FIL)-MCL-0208 Trial: A Focus on the B Cell Receptor Pathway," ASH 57th Annual Meeting & Exposition, Dec. 5-8, 2015 (2 pages).

Campo, "Mantle Cell Lymphoma," Presentation, Mar. 3, 2013 at 102nd Annual Meeting USCAP (6 pages).

Cao et al., "Serial analysis of gene expression of lobular carcinoma in situ identifies down regulation of claudin 4 and overexpression of matrix metalloproteinase 9," Breast Cancer Research, 10 (5), R91 (2008) (10 pages).

Cheah et al., "Mantle cell lymphoma," J. Clin. Oncol., 34 (11), 1256-1269 (2016).

De Jong et al., "Immunohistochemical prognostic markers in diffuse large B-cell lymphoma: Validation of tissue microarray as a prerequisite for broad clinical applications—A study from the Lunenburg Lymphoma Biomarker Consortium," J. Clin. Oncol., 25 (7), 805-812 (2007).

De Leeuw et al., "Comprehensive whole genome array CGH profiling of mantle-cell lymphoma model genomes" Human Molecular Genetics, 13 (17), 1827-1837 (2004).

Determann et al., "Ki-67 predicts outcome in advanced-stage mantle cell lymphoma patients treated with anti-CD20 immunochemotherapy: results from randomized trials of the European MCL Network and the German Low Grade Lymphoma Study Group," Blood, 111 (4), 2385-2387 (2008).

Dreyling et al., "New paradigms in mantle cell lymphoma: Is it time to risk-stratify treatment based on the proliferative signature?" Ciin. Cancer Res., 20 (20), 5194-5206 (2014).

Dreyling et al., "How to manage mantle cell lymphoma," Leukemia, 28 (11), 2117-2130 (2014).

Ek et al., "Parallel Gene Expression Profiling of Mantle Cell Lymphoma—How Do we Transform Omics Data into Clinical Practice," Current Genomics, 8, 171-179 (2007).

Fernàndez et al., "Genomic and gene expression profiling defines indolent forms of mantle cell lymphoma," Cancer Res., 70 (4), 1408-1418 (2010).

Filipits et al., "The PAM50 risk-of-recurrence score predicts risk for late distant recurrence after endocrine therapy in postmenopausal women with endocrine-responsive early breast cancer," Clin. Cancer Res., 20 (5), 1298-1305 (2014).

Fortina et al., "Digital mRNA profiling," Nat. Biotechnol., 26 (3), 293-294 (2008).

Geisler et al., "Nordic MCL2 trial update: Six-year follow-up after intensive immunochemotherapy for untreated mantle cell lymphoma followed by BEAM or BEAC + autologous stem-cell support: Still very long survival but late relapses do occur," Br. J. Haematol., 158 (3), 355-362 (2012).

Geiss et al., "Direct multiplexed measurement of gene expression with color-coded probe pairs," Nature Biotechnol, 26 (3), 317-325 (2008) (with comment by Fortina et al., "Digital mRNA profiling," Nature Biotechnol., 26 (3), 293-294 (2008).

Gene Expression Omnibus, GEO Accession No. GSE93291. https://www.ncbi.nlm.nih.gov/geo/query/acc.cgi, public Mar. 17, 2017 (2 pages).

Hartmann et al., "Five-gene model to predict survival in mantle-cell lymphoma using frozen or formalin-fixed, paraffin-embedded tissue," J. Clin. Oncol., 26 (30), 4966-4972 (2008).

Hartmann et al., "Pathway discovery in mantle cell lymphoma by integrated analysis of high-resolution gene expression and copy number profiling," Blood, 116 (6), 953-961 (2010).

Henson et al., "Candidate genes contributing to the aggressive phenotype of mantle cell lymphoma," Acta Histochem., 113 (7), 729-742 (2011) author manuscript.

Hofmann et al., "Altered apoptosis pathways in mantle cell lymphoma detected by oligonucleotide microarray," Blood, 98 (3), 787-794 (2001).

Hoster et al., "A new prognostic index (MIPI) for patients with advanced-stage mantle cell lymphoma," Blood, 111 (2), 558-565 (2008).

Hoster et al., "Confirmation of the mantle-cell lymphoma International Prognostic Index in randomized trials of the European Mantle-Cell Lymphoma Network," J. Clin. Oncol., 32 (13), 1338-1346 (2014).

Hoster et al., "Prognostic value of Ki-67 index, cytology, and growth pattern in mantle-cell lymphoma: Results from randomized trials of the European Mantle Cell Lymphoma Network," J. Clin. Oncol., 34 (12), 1386-1394 (2016).

Huang et al., "Simultaneous recovery of DNA and RNA from formalin-fixed paraffin-embedded tissue and application in epidemiologic studies," Cancer Epidemiol. Biomarkers Prev., 19 (4), 973-977 (2010) (retracted May 1, 2014).

Igarashi et al., "Factors affecting toxicity, response and progression-free survival in relapsed patients with indolent B-cell lymphoma and mantle cell lymphoma treated with rituximab: a Japanese phase II study," Ann. Oncol., 13 (6), 928-943 (2002).

International Preliminary Report on Patentability, Application No. PCT/US2017/028628, dated Oct. 23, 2018 (7 pages).

Iqbal et al., "Gene expression profiling in lymphoma diagnosis and management," Best Pract. Res. Clin. Haematol., 22 (2), 191-210 (2009).

International Search Report, Application No. PCT/US2017/028628, dated Jul. 18, 2017 (5 pages).

(56) References Cited

OTHER PUBLICATIONS

Jacobs et al., "Genome-wide, high-resolution detection of copy number, loss of heterozygosity, and genotypes from formalin-fixed, paraffin-embedded tumor tissue using microarrays," Cancer Res., 67 (6), 2544-2551 (2007).
Jares et al., "Molecular pathogenesis of mantle cell lymphoma," J. Clin. Invest., 122 (10), 3416-3423 (2012).
Jares et al., "Genetic and molecular pathogenesis of mantle cell lymphoma: perspectives for new targeted therapeutics," Nat. Rev. Cancer, 7 (10), 750-762 (2007).
Katzenberger et al., "The Ki67 proliferation index is a quantitative indicator of clinical risk in mantle cell lymphoma," Blood, 107 (8), 3407 (2006), (1 page).
Kienle et al, "Quantitative gene expression deregulation in mantle-cell lymphoma: Correlation with clinical and biologic factors," J. Clin. Oncol., 25 (19), 2770-2777 (2007).
Klapper et al., "Ki-67 as a prognostic marker in mantle cell lymphoma-consensus guidelines of the pathology panel of the European MCL Network," J. Hematop., 2(2), 103-111 (2009).
Kulkarni, "Digital Multiplexed Gene Expression Analysis Using the NanoString nCounter System," Curr. Protac. Mol. Biol., Unit 25B. 10. Supplement 94 (2011) (17 pages).
Lardelli et al., "Lymphocytic lymphoma of intermediate differentiation. Morphologic and immunophenotypic spectrum and clinical correlations," Am. J. Surg. Pathol., 14 (8), 752-763 (1990).
Martinez et al., "The molecular signature of mantle cell lymphoma reveals multiple signals favoring cell survival," Cancer Res., 63 (23), 8226-8232 (2003).
Matsumura et al., "Gene expression analysis of plant host-pathogen interactions by SuperSAGE," Proc. Natl. Acad. Sci. USA, 100 (26), 15718-15723 (2003).
Montgomery et al., "Pathology consultation on intermediate-to-large B-cell lymphomas," Am. J. Clin. Pathol., 141 (3), 305-317 (2014).
Mortazavi et al. "Mapping and quantifying mammalian transcriptomes by RNA-Seq," Nat. Methods, 5 (7), 621-628 (2008).
Nordström et al., "SOX11 and TP53 add prognostic information to MIPI in a homogenously treated cohort of mantle cell lymphoma—A Nordic Lymphoma Group study," Br. J. Haematol., 166 (1), 98-108 (2014).
Orchard et al., "A subset of t(11;14) lymphoma with mantle cell features displays mutated IgVH genes and includes patients with good prognosis, nonnodal disease," Blood, 101 (12), 4975-4981 (2003).
Ortega-Paino et al., "Functionally associated targets in mantle cell lymphoma as defined by DNA microarrays and RNA interference," Blood, 111 (3), 1617-1624 (2008).
Pollard et al., "Supervised Distance Matrices: Theory and Applications to Genomics," Paper 238 (2008) (32 pages).
Puvvada et al., "Molecular classification, pathway addiction, and therapeutic targeting in diffuse large B cell lymphoma," Cancer Genet, 206 (7-8), 257-265 (2013) author manuscript.
Rizzatti et al., "Gene expression profiling of mantle cell lymphoma cells reveals aberrant expression of genes from the PI3K-AKT, WNT and TGFbeta signalling pathways," Br. J. Haematol., 130 (4), 516-526 (2005).
Robetorye et al., "Microarray analysis of B-cell lymphoma cell lines with the t(14;18)," J. Mol Diagn., 4 (3), 123-136 (2002).
Rosenwald et al., "The use of molecular profiling to predict survival after chemotherapy for diffuse large-B-cell lymphoma," N. Engl. J. Med., 346 (25), 1937-1947 (2002).
Rosenwald et al. "The proliferation gene expression signature is a quantitative integrator of oncogenic events that predicts survival in mantle cell lymphoma," Cancer Cell, 3 (2), 185-197 (2003).
Rosenwald, "DNA microarrays in lymphoid malignancies," Oncology Journal, 17 (12), 1743-1748 (2003).
Rubio-Moscardo et al., "Mantle-cell lymphoma genotypes identified with CGH to BAC microarrays define a leukemic subgroup of disease and predict patient outcome," Blood, 105 (11), 4445-4454 (2005).
Rummel et al., "Bendamustine plus rituximab versus CHOP plus rituximab as first-line treatment for patients with indolent and mantle-cell lymphomas: an open-label, multicentre, randomised, phase 3 non-inferiority trial," Lancet, 381 (9873), 1203-1210 (2013).
Saba et al., Pathogenic role of B-cell receptor signaling and canonical NF-κB activation in mantle cell lymphoma, Blood, 128 (1), 82-92 (2016).
Salaverria et al., "Specific secondary genetic alterations in mantle cell lymphoma provide prognostic in formation independent of the gene expression-based proliferation signature," J. Clin. Oncol., 25 (10), 1216-1222 (2007).
Scott et al., "Determining cell-of-origin subtypes of diffuse large B-cell lymphoma using gene expression in formalin-fixed paraffin-embedded tissue," Blood, 123 (8), 1214-1217 (2014).
Scott et al., "Prognostic significance of the proliferation signature in mantle cell lymphoma measured using digital gene expression in formalin-fixed paraffin-embedded tissue biopsies," abstract No. 7510 (previously No. 163878) and presentation at the 2016 annual meeting of the American Society of Clinical Oncology, J. Clin. Oncol., 34 (15 suppl.), May 20, 2016 abstract title published Apr. 20, 2016, (2 pages).
Scott et al., "New Molecular Assay for the Proliferation Signature in Mantle Cell Lymphoma Applicable to Formalin-Fixed Paraffin-Embedded Biopsies," J. Ciin. Oncol., 35 (15), 1668-1677 (2017).
Shaffer et al., "Signatures of the immune response," Immunity, 15 (3), 375-385 (2001).
Staudt et al., "The biology of human lymphoid malignancies revealed by gene expression profiling," Adv. Immunol., 87, 163-208 (2005) author manuscript.
Swerdlow et al., "The 2016 revision of the World Health Organization classification of lymphoid neoplasms," Blood, 127 (20), 2375-2390 (2016).
Thieblemont et al., "Small lymphocytic lymphoma, marginal zone B-cell lymphoma, and mantle cell lymphoma exhibit distinct gene-expression profiles allowing molecular diagnosis" Blood, 103 (7), 2727-2737 (2004).
Tiemann et al., "Hislopathology, cell proliferation indices and clinical outcome in 304 patients with mantle cell lymphoma (MCL): A clinicopathological study from the European MCL Network," Br. J. Haematol., 131 (1), 29-38 (2005).
Van Der Velden et al., "B-cell prolymphocytic leukemia: a specific subgroup of mantle cell lymphoma" Blood, 124 (3), 412-419 (2014).
Velculescu et al., "Serial analysis of gene expression," Science, 270 (5235), 484-487 (1995).
Wright et al., "A gene expression-based method to diagnose clinically distinct subgroups of diffuse large B cell lymphoma," Proc. Natl. Acad. Sci. USA, 100 (17), 9991-9996 (2003).
Written Opinion of the International Searching Authority, Application No. PCT/US2017/028628, (6 pages).

* cited by examiner

SEQUENCE LISTING

```
<160> NUMBER OF SEQ ID NOS: 165

<210> SEQ ID NO 1
<211> LENGTH: 100
<212> TYPE: DNA
<213> ORGANISM: Artificial Sequence
<220> FEATURE:
<223> OTHER INFORMATION: Synthetic

<400> SEQUENCE: 1
gattccttgg ctacttagtc ccgagagcct agatattaaa gagatcaatg ggaataaaat      60
cacctgccgg ggtctggtgg agtacttcaa ggcttatata                          100

<210> SEQ ID NO 2
<211> LENGTH: 100
<212> TYPE: DNA
<213> ORGANISM: Artificial Sequence
<220> FEATURE:
<223> OTHER INFORMATION: Synthetic
```

<400> SEQUENCE: 2
gggaacttcc aggataacct gcagatgctc acaccgcaac tcaatgccat cattgcggcg    60
tccgcttccg tcaagtcttc acagaagctg aagcagatgt                         100

<210> SEQ ID NO 3
<211> LENGTH: 100
<212> TYPE: DNA
<213> ORGANISM: Artificial Sequence
<220> FEATURE:
<223> OTHER INFORMATION: Synthetic

<400> SEQUENCE: 3
ctgcgttcga atccataaca agttccgatc agaggtgaaa ccaacagcca gtgatatgct    60
atacatgact tgggacccag cactagccca aattgcaaaa                         100

<210> SEQ ID NO 4
<211> LENGTH: 100
<212> TYPE: DNA
<213> ORGANISM: Artificial Sequence
<220> FEATURE:
<223> OTHER INFORMATION: Synthetic

<400> SEQUENCE: 4
cccaagatcc cacatggaga aagggagttc tgggaattat gtaacaagtg taatttgatg    60
agaccaaagc gttcccatca ctgtagccgc tgcggccact                         100

<210> SEQ ID NO 5
<211> LENGTH: 100
<212> TYPE: DNA
<213> ORGANISM: Artificial Sequence
<220> FEATURE:
<223> OTHER INFORMATION: Synthetic

<400> SEQUENCE: 5
agaggcatct gtgaaattcc atgtgctgct gacatcctat gaattgatca ccattgacat    60
ggctattttg ggctctattg attgggcctg cctcatcgtg                         100

<210> SEQ ID NO 6
<211> LENGTH: 100
<212> TYPE: DNA
<213> ORGANISM: Artificial Sequence
<220> FEATURE:
<223> OTHER INFORMATION: Synthetic

<400> SEQUENCE: 6
cacagagacc cctttctgca cgaacataca gcatagatgg tccaaatgca tcaagacctc    60
agagtgctcg accctctatt aatgaaatac cagagagaac                         100

<210> SEQ ID NO 7
<211> LENGTH: 100
<212> TYPE: DNA
<213> ORGANISM: Artificial Sequence
<220> FEATURE:
<223> OTHER INFORMATION: Synthetic

<400> SEQUENCE: 7
cagattttac aggctgaatt attggcagta tatggagcag acccaggcac acaggattct    60
agtgggaaaa ctcccgttga ttatgcaagg caaggagggc                         100

<210> SEQ ID NO 8
<211> LENGTH: 100
<212> TYPE: DNA
<213> ORGANISM: Artificial Sequence
<220> FEATURE:
<223> OTHER INFORMATION: Synthetic

<400> SEQUENCE: 8
actgattata cctctagtat agatgtatgg tctgctggct gtgtgttggc tgagctgtta    60
ctaggacaac caatatttcc agggatagt ggtgtggatc                          100

<210> SEQ ID NO 9
<211> LENGTH: 100
<212> TYPE: DNA
<213> ORGANISM: Artificial Sequence
<220> FEATURE:
<223> OTHER INFORMATION: Synthetic

<400> SEQUENCE: 9
ttcaagagag agacaggggt tgatttgact aaagacaaca tggcacttca gagggtacgg    60
gaagctgctg aaaaggctaa atgtgaactc tcctcatctg                         100

<210> SEQ ID NO 10
<211> LENGTH: 100
<212> TYPE: DNA
<213> ORGANISM: Artificial Sequence
<220> FEATURE:
<223> OTHER INFORMATION: Synthetic

<400> SEQUENCE: 10
gtccaaattc ttgggtggtg acatggaaca cacccatttg gtgaaaggct tggattttgc    60
tctgcttcaa aaggtacgag ctgagattgc cagcaaagag                         100

<210> SEQ ID NO 11
<211> LENGTH: 100
<212> TYPE: DNA
<213> ORGANISM: Artificial Sequence
<220> FEATURE:
<223> OTHER INFORMATION: Synthetic

<400> SEQUENCE: 11
ccaacattaa ttttcctaat ctcaagcaag actacccaga ctggtcaagc cgttgcaaac    60
aaatcatgaa gctctggaga aaggttccag cagctgacaa                         100

<210> SEQ ID NO 12
<211> LENGTH: 100
<212> TYPE: DNA
<213> ORGANISM: Artificial Sequence
<220> FEATURE:
<223> OTHER INFORMATION: Synthetic

<400> SEQUENCE: 12
tggttctaag atttctcatc ttctcatccc taggacaagc atagtgcctg catgcttcat    60
gatcagtaag tcctggctgc ataaaggact ctgatgtcaa                         100

<210> SEQ ID NO 13
<211> LENGTH: 100
<212> TYPE: DNA
<213> ORGANISM: Artificial Sequence
<220> FEATURE:
<223> OTHER INFORMATION: Synthetic

<400> SEQUENCE: 13
cctgtgttcc aagagaatt acattattga caaaagactc caagacgagg atgccagtag    60
tacccagcag aggcgccaga tatttagagt taataaagat                         100

<210> SEQ ID NO 14
<211> LENGTH: 100
<212> TYPE: DNA
<213> ORGANISM: Artificial Sequence
<220> FEATURE:
<223> OTHER INFORMATION: Synthetic

<400> SEQUENCE: 14
ttgaaggatg cattcagtct actagcatat tcagatccct ggaacagccc agttggaaat    60
cagcttgacc cgattcagag agaacctgtg tgctcagctc                         100

<210> SEQ ID NO 15
<211> LENGTH: 100
<212> TYPE: DNA
<213> ORGANISM: Artificial Sequence
<220> FEATURE:
<223> OTHER INFORMATION: Synthetic

<400> SEQUENCE: 15
agatccaata attcccttta gtgatggacc catcatctca aaatggggtg cgatttccag    60
atcttcccgt acaggttacc ataccacaga tcctgtccag                         100

<210> SEQ ID NO 16
<211> LENGTH: 100
<212> TYPE: DNA
<213> ORGANISM: Artificial Sequence
<220> FEATURE:
<223> OTHER INFORMATION: Synthetic

<400> SEQUENCE: 16
gtggaggccg aggacatttt cctgaagggc aggggttggc aacttttcaa catggagtgc    60
caaactgcta acccgtcttc tagtgtgtga aatagggac                          100

<210> SEQ ID NO 17
<211> LENGTH: 100
<212> TYPE: DNA
<213> ORGANISM: Artificial Sequence
<220> FEATURE:
<223> OTHER INFORMATION: Synthetic

<400> SEQUENCE: 17
catcgcgacg gccaaaagga gcggcgcggt cttcgtggtg ttcgtggcag gtgatgatga    60
acagtctaca cagatggctg caagttggga agatgataaa                         100

<210> SEQ ID NO 18
<211> LENGTH: 100
<212> TYPE: DNA
<213> ORGANISM: Artificial Sequence
<220> FEATURE:
<223> OTHER INFORMATION: Synthetic

<400> SEQUENCE: 18
ccacctcagt gacacggcca ttgggatgat gaccaggatt gcagttctca agtggctcta    60
ccacctctac atcaaaactc ctcggaagat gttccggcac                         100

<210> SEQ ID NO 19
<211> LENGTH: 100
<212> TYPE: DNA
<213> ORGANISM: Artificial Sequence
<220> FEATURE:
<223> OTHER INFORMATION: Synthetic

<400> SEQUENCE: 19
acagacaaga gtgggcgaca gtggaagctg aagtccttcc agaccaggga caaccagggc    60
attctctatg aagctgcacc cacctccacc ctcacctgtg    100

<210> SEQ ID NO 20
<211> LENGTH: 100
<212> TYPE: DNA
<213> ORGANISM: Artificial Sequence
<220> FEATURE:
<223> OTHER INFORMATION: Synthetic

<400> SEQUENCE: 20
cctctggact gaaccccaca tctgcacctc caacatctgc ttcagcggtc cctgtttctc    60
ctgttccaca gtcgccaata cctcccttac ttcaggaccc    100

<210> SEQ ID NO 21
<211> LENGTH: 100
<212> TYPE: DNA
<213> ORGANISM: Artificial Sequence
<220> FEATURE:
<223> OTHER INFORMATION: Synthetic

<400> SEQUENCE: 21
ctacctcttc aattggaatg gctttggggc cacaagtgac cgctttgccc tgagagctga    60
atctatcgac tgcatggttc cagtcaccga gagtctgctg    100

<210> SEQ ID NO 22
<211> LENGTH: 100
<212> TYPE: DNA
<213> ORGANISM: Artificial Sequence
<220> FEATURE:
<223> OTHER INFORMATION: Synthetic

<400> SEQUENCE: 22
tcagacaggg cctgatctcc gcagcccagt attacaagag ttgccgggac ctgctggggg    60
agaatttcca gaaggtcttt aatgagctgc tggtcctgct    100

<210> SEQ ID NO 23
<211> LENGTH: 100
<212> TYPE: DNA
<213> ORGANISM: Artificial Sequence
<220> FEATURE:
<223> OTHER INFORMATION: Synthetic

<400> SEQUENCE: 23
aggttgatgt tgaacagcac actttagcca agtatttgat ggagctgact ctcatcgact    60
atgatatggt gcattatcat ccttctaagg tagcagcagc    100

<210> SEQ ID NO 24
<211> LENGTH: 100
<212> TYPE: DNA
<213> ORGANISM: Artificial Sequence
<220> FEATURE:
<223> OTHER INFORMATION: Synthetic

<400> SEQUENCE: 24
ggaacatcag aaagcctggg ctttgaacct gaacggtttt gatgtagagg aagccaagat      60
ccttcggctc agtggaaaac cacaaaatgc gccagagggt                            100

<210> SEQ ID NO 25
<211> LENGTH: 100
<212> TYPE: DNA
<213> ORGANISM: Artificial Sequence
<220> FEATURE:
<223> OTHER INFORMATION: Synthetic

<400> SEQUENCE: 25
taccgaaaaa ccttaataca ctgctatgga ggacttggga gatcttgtct tgtagctgct      60
tgtctcctac tatacctgtc tgacacaata tcaccagagc                            100

<210> SEQ ID NO 26
<211> LENGTH: 100
<212> TYPE: DNA
<213> ORGANISM: Artificial Sequence
<220> FEATURE:
<223> OTHER INFORMATION: Synthetic

<400> SEQUENCE: 26
tcagggaccc tgtgtaggat ctcgtttgtg gtgagtgggc tgctctgagg tctccactgg      60
gctgccattt agccatgtgc catctctgaa gtcagaggtg                            100

<210> SEQ ID NO 27
<211> LENGTH: 100
<212> TYPE: DNA
<213> ORGANISM: Artificial Sequence
<220> FEATURE:
<223> OTHER INFORMATION: Synthetic

<400> SEQUENCE: 27
cagggacttc acctctacac tgtggtggtt tatgactttg cccaaggctg tcagatagtt      60
gatttggctg acctgaccca actagtggac agttgtaaat                            100

<210> SEQ ID NO 28
<211> LENGTH: 100
<212> TYPE: DNA
<213> ORGANISM: Artificial Sequence
<220> FEATURE:
<223> OTHER INFORMATION: Synthetic

<400> SEQUENCE: 28
cacgttgatt gatggcatcc gcgtggcaac aggctcctac agttttacat ggacggatgg      60
caaattaaac agcagtaact tggtaattct gtctggccaa                            100

<210> SEQ ID NO 29
<211> LENGTH: 100
<212> TYPE: DNA
<213> ORGANISM: Artificial Sequence
<220> FEATURE:
<223> OTHER INFORMATION: Synthetic

<400> SEQUENCE: 29
aagtcttttg tattgggtca ggagttgaat ttggggtggg aggatggatg caactgaagc      60
agagtgtggg tgcccagatg tgcgctatta gatgtttctc                            100

<210> SEQ ID NO 30
<211> LENGTH: 100
<212> TYPE: DNA
<213> ORGANISM: Artificial Sequence
<220> FEATURE:
<223> OTHER INFORMATION: Synthetic

<400> SEQUENCE: 30
ccgccccatt tccccttccag caaactcaac tcggcaatcc aagcacctag ataccagcac    60
aagtcggtta atccctgtct ggactgagcc tccgttggct                          100

<210> SEQ ID NO 31
<211> LENGTH: 100
<212> TYPE: DNA
<213> ORGANISM: Artificial Sequence
<220> FEATURE:
<223> OTHER INFORMATION: Synthetic

<400> SEQUENCE: 31
cctgctctaa cggggcgctg attccaggca atttatccaa ggaagaggag gaactgtctt    60
cccagatgtc cagctttaac gaagccatga ctcagatcag                          100

<210> SEQ ID NO 32
<211> LENGTH: 100
<212> TYPE: DNA
<213> ORGANISM: Artificial Sequence
<220> FEATURE:
<223> OTHER INFORMATION: Synthetic

<400> SEQUENCE: 32
agcagatgta gagggagaac tcttagcgtg caggaatcta atgccatcag caggcaaagc    60
catgcacacg cctaaaccat cagtaggtga agagaaagac                          100

<210> SEQ ID NO 33
<211> LENGTH: 100
<212> TYPE: DNA
<213> ORGANISM: Artificial Sequence
<220> FEATURE:
<223> OTHER INFORMATION: Synthetic

<400> SEQUENCE: 33
gtattgcacc atcagcaaag actttgccaa aaattgtagg gcgcaccaag gatgtgaaag    60
aggctgtcag aaagctggct tatcaggttt tagctgaaaa                          100

<210> SEQ ID NO 34
<211> LENGTH: 100
<212> TYPE: DNA
<213> ORGANISM: Artificial Sequence
<220> FEATURE:
<223> OTHER INFORMATION: Synthetic

<400> SEQUENCE: 34
tttcagctct tgacctgtcc cctctggctg cctctgagtc tgaatctccc aaagagagaa    60
accaatttct aagaggactg gattgcagaa gactcgggga                          100

<210> SEQ ID NO 35
<211> LENGTH: 100
<212> TYPE: DNA
<213> ORGANISM: Artificial Sequence
<220> FEATURE:
<223> OTHER INFORMATION: Synthetic

<400> SEQUENCE: 35
ggagatgtaa atttgccatg acttcctgga ggacagcagc atggagaaag atcctagaaa        60
aggcctctga cttccctcac ctcccaacca tcattacagg                              100

<210> SEQ ID NO 36
<211> LENGTH: 100
<212> TYPE: DNA
<213> ORGANISM: Artificial Sequence
<220> FEATURE:
<223> OTHER INFORMATION: Synthetic

<400> SEQUENCE: 36
acactccatc ttagcaggag atcccttga actagaatgc cctgtgaaat actgtgctaa        60
caggcctcat gtgacttggt gcaagctcaa tggaacaaca                              100

<210> SEQ ID NO 37
<211> LENGTH: 100
<212> TYPE: DNA
<213> ORGANISM: Artificial Sequence
<220> FEATURE:
<223> OTHER INFORMATION: Synthetic

<400> SEQUENCE: 37
ttgaacactt cctctccaaa atgccagagg cggaggagaa caaacagatc atccgcaaac        60
acgcgcagac cttcgttgcc ctctgtgcca cagatgtgaa                              100

<210> SEQ ID NO 38
<211> LENGTH: 100
<212> TYPE: DNA
<213> ORGANISM: Artificial Sequence
<220> FEATURE:
<223> OTHER INFORMATION: Synthetic

<400> SEQUENCE: 38
tgctaattta aagagactcc aaatctcaat gaagccagct cacagtgctg tgtgccccgg        60
tcacctagca agctgccgaa ccaaaagaat ttgcaccccg                              100

<210> SEQ ID NO 39
<211> LENGTH: 100
<212> TYPE: DNA
<213> ORGANISM: Artificial Sequence
<220> FEATURE:
<223> OTHER INFORMATION: Synthetic

<400> SEQUENCE: 39
attgattcag cctgtttggc gtttcccaga gtcatctgat tggacaggca tgggtgcaag        60
gaaaattagg gtactcaacc taagttcggt tccgatgaat                              100

<210> SEQ ID NO 40
<211> LENGTH: 100
<212> TYPE: DNA
<213> ORGANISM: Artificial Sequence
<220> FEATURE:
<223> OTHER INFORMATION: Synthetic

<400> SEQUENCE: 40
ccctcggtca gggattgaaa atagtacagt gactctgtct cacccaaatg ggaccacgtc        60
tgttaccagc atcctccata tcaaagaccc taagaatcag                              100

```
<210> SEQ ID NO 41
<211> LENGTH: 100
<212> TYPE: DNA
<213> ORGANISM: Artificial Sequence
<220> FEATURE:
<223> OTHER INFORMATION: Synthetic

<400> SEQUENCE: 41
tgatcccaaa tactgtgctg ctcctacaga acctgtcatt cacaacggaa gccaaggaac      60
aggaacaaat ggttcggaaa tcagtgatag tgattatcag                          100

<210> SEQ ID NO 42
<211> LENGTH: 100
<212> TYPE: DNA
<213> ORGANISM: Artificial Sequence
<220> FEATURE:
<223> OTHER INFORMATION: Synthetic

<400> SEQUENCE: 42
ctatatacat cacgttaaag taggactatc acacccagcc catgtggcta aaaaagctga      60
atcagacagt ggatgagaca cacaacggca gtgaagaacc                          100

<210> SEQ ID NO 43
<211> LENGTH: 100
<212> TYPE: DNA
<213> ORGANISM: Artificial Sequence
<220> FEATURE:
<223> OTHER INFORMATION: Synthetic

<400> SEQUENCE: 43
tggaggaggc agcagctatt attgcccagc ggcctgacaa cccaagggag ttcttcaagc      60
agcaggaaag agtcgcatcg gcctctgcgg gcagctgtga                          100

<210> SEQ ID NO 44
<211> LENGTH: 100
<212> TYPE: DNA
<213> ORGANISM: Artificial Sequence
<220> FEATURE:
<223> OTHER INFORMATION: Synthetic

<400> SEQUENCE: 44
gagtgtcaga agatgcgtta ttgggctcag agattgcaca ggtaacaggg aatgatgtgg      60
actcaggacc cgtgctgtgg tatgtgctaa gcccatctgg                          100

<210> SEQ ID NO 45
<211> LENGTH: 100
<212> TYPE: DNA
<213> ORGANISM: Artificial Sequence
<220> FEATURE:
<223> OTHER INFORMATION: Synthetic

<400> SEQUENCE: 45
tcatggtacg tagtccccgg cacctgtcgt tattcctata tcctcctgca actgtggttt      60
gaaactgcgc attctctagt agtatatatc gtgcctgtct                          100

<210> SEQ ID NO 46
<211> LENGTH: 100
<212> TYPE: DNA
<213> ORGANISM: Artificial Sequence
<220> FEATURE:
<223> OTHER INFORMATION: Synthetic
```

<400> SEQUENCE: 46
ccagtgtggt ggcctatgaa ggacaatcct ggcacgacta ctgcttccac tgcaaaaaat    60
gctccgtgaa tctggccaac aagcgctttg ttttccacca    100

<210> SEQ ID NO 47
<211> LENGTH: 100
<212> TYPE: DNA
<213> ORGANISM: Artificial Sequence
<220> FEATURE:
<223> OTHER INFORMATION: Synthetic

<400> SEQUENCE: 47
ccagggagtt tgcagcctaa attagcagag accatgaata acattgaccg cctacgaatg    60
gaaatccata agaatgaggc ttggctctct gaagtcgaag    100

<210> SEQ ID NO 48
<211> LENGTH: 100
<212> TYPE: DNA
<213> ORGANISM: Artificial Sequence
<220> FEATURE:
<223> OTHER INFORMATION: Synthetic

<400> SEQUENCE: 48
cccagtgcca atacaatttt gagctaagca ctcaaggtgg atactttaca ttttaaagct    60
ggaatcagca acagccctat gggaaaccag acaaagcatt    100

<210> SEQ ID NO 49
<211> LENGTH: 100
<212> TYPE: DNA
<213> ORGANISM: Artificial Sequence
<220> FEATURE:
<223> OTHER INFORMATION: Synthetic

<400> SEQUENCE: 49
tcggacaccg aggagaatgt caagaggcga acacacaacg tcttggagcg ccagaggagg    60
aacgagctaa aacggagctt ttttgccctg cgtgaccaga    100

<210> SEQ ID NO 50
<211> LENGTH: 100
<212> TYPE: DNA
<213> ORGANISM: Artificial Sequence
<220> FEATURE:
<223> OTHER INFORMATION: Synthetic

<400> SEQUENCE: 50
agaaaacact tgttgaaaa acgatctggg aagggttcgg caagagcttg aagctgcaga    60
aagtactcac gatgcacaga ggaaggaaat tgaggtttta    100

<210> SEQ ID NO 51
<211> LENGTH: 100
<212> TYPE: DNA
<213> ORGANISM: Artificial Sequence
<220> FEATURE:
<223> OTHER INFORMATION: Synthetic

<400> SEQUENCE: 51
aaactcattg tttccttgtg gtaagtgacc gagatgctgc cacaggacct gagacactga    60
tgaatggtgc tattttggac tttcaacatg ctccttggcg    100

```
<210> SEQ ID NO 52
<211> LENGTH: 100
<212> TYPE: DNA
<213> ORGANISM: Artificial Sequence
<220> FEATURE:
<223> OTHER INFORMATION: Synthetic

<400> SEQUENCE: 52
ccaacagctt gcctctgagg ttctggatca atataataaa aaacccgcag tttgtgttcg      60
acgtgcaaac atctgataac atggatgcgg tgctccttgt                           100

<210> SEQ ID NO 53
<211> LENGTH: 100
<212> TYPE: DNA
<213> ORGANISM: Artificial Sequence
<220> FEATURE:
<223> OTHER INFORMATION: Synthetic

<400> SEQUENCE: 53
ttcctcgggg gacatctggg taggctgtca tcctaatggc cagaagctct tcgtgtatga      60
cccgaacaat cctccctcgt cagaggttct ccgcatccag                           100

<210> SEQ ID NO 54
<211> LENGTH: 100
<212> TYPE: DNA
<213> ORGANISM: Artificial Sequence
<220> FEATURE:
<223> OTHER INFORMATION: Synthetic

<400> SEQUENCE: 54
gtgtctcttg atccatccga agcaggccct ccacgttatc taggagatcg ctacaagttt      60
tatctggaga atctcaccct ggggatacgg gaaagcagga                           100

<210> SEQ ID NO 55
<211> LENGTH: 100
<212> TYPE: DNA
<213> ORGANISM: Artificial Sequence
<220> FEATURE:
<223> OTHER INFORMATION: Synthetic

<400> SEQUENCE: 55
ctaagcattg acagaatatc ttaaaatggt aacctggggg tggcgggtgg gtgctgtgtg      60
cacggcagcc tagccagtgg ggatcctgct gtttattata                           100

<210> SEQ ID NO 56
<211> LENGTH: 50
<212> TYPE: DNA
<213> ORGANISM: Artificial Sequence
<220> FEATURE:
<223> OTHER INFORMATION: Synthetic

<400> SEQUENCE: 56
cattgatctc tttaatatct aggctctcgg gactaagtag ccaaggaatc                 50

<210> SEQ ID NO 57
<211> LENGTH: 38
<212> TYPE: DNA
<213> ORGANISM: Artificial Sequence
<220> FEATURE:
<223> OTHER INFORMATION: Synthetic

<400> SEQUENCE: 57
atggcattga gttgcggtgt gagcatctgc aggttatc                              38
```

```
<210> SEQ ID NO 58
<211> LENGTH: 50
<212> TYPE: DNA
<213> ORGANISM: Artificial Sequence
<220> FEATURE:
<223> OTHER INFORMATION: Synthetic

<400> SEQUENCE: 58
tggctgttgg tttcacctct gatcggaact tgttatggat tcgaacgcag            50

<210> SEQ ID NO 59
<211> LENGTH: 48
<212> TYPE: DNA
<213> ORGANISM: Artificial Sequence
<220> FEATURE:
<223> OTHER INFORMATION: Synthetic

<400> SEQUENCE: 59
cacttgttac ataattccca gaactccctt tctccatgtg ggatcttg              48

<210> SEQ ID NO 60
<211> LENGTH: 50
<212> TYPE: DNA
<213> ORGANISM: Artificial Sequence
<220> FEATURE:
<223> OTHER INFORMATION: Synthetic

<400> SEQUENCE: 60
tgatcaattc ataggatgtc agcagcacat ggaatttcac agatgcctct            50

<210> SEQ ID NO 61
<211> LENGTH: 50
<212> TYPE: DNA
<213> ORGANISM: Artificial Sequence
<220> FEATURE:
<223> OTHER INFORMATION: Synthetic

<400> SEQUENCE: 61
tgcatttgga ccatctatgc tgtatgttcg tgcagaaagg ggtctctgtg            50

<210> SEQ ID NO 62
<211> LENGTH: 50
<212> TYPE: DNA
<213> ORGANISM: Artificial Sequence
<220> FEATURE:
<223> OTHER INFORMATION: Synthetic

<400> SEQUENCE: 62
gtgcctgggt ctgctccata tactgccaat aattcagcct gtaaaatctg            50

<210> SEQ ID NO 63
<211> LENGTH: 50
<212> TYPE: DNA
<213> ORGANISM: Artificial Sequence
<220> FEATURE:
<223> OTHER INFORMATION: Synthetic

<400> SEQUENCE: 63
gccaacacac agccagcaga ccatacatct atactagagg tataatcagt            50

<210> SEQ ID NO 64
<211> LENGTH: 50
<212> TYPE: DNA
<213> ORGANISM: Artificial Sequence
<220> FEATURE:
<223> OTHER INFORMATION: Synthetic
```

<400> SEQUENCE: 64
tgaagtgcca tgttgtcttt agtcaaatca acccctgtct ctctcttgaa                50

<210> SEQ ID NO 65
<211> LENGTH: 50
<212> TYPE: DNA
<213> ORGANISM: Artificial Sequence
<220> FEATURE:
<223> OTHER INFORMATION: Synthetic

<400> SEQUENCE: 65
agcctttcac caaatgggtg tgttccatgt caccacccaa gaatttggac                50

<210> SEQ ID NO 66
<211> LENGTH: 50
<212> TYPE: DNA
<213> ORGANISM: Artificial Sequence
<220> FEATURE:
<223> OTHER INFORMATION: Synthetic

<400> SEQUENCE: 66
gcttgaccag tctgggtagt cttgcttgag attaggaaaa ttaatgttgg                50

<210> SEQ ID NO 67
<211> LENGTH: 50
<212> TYPE: DNA
<213> ORGANISM: Artificial Sequence
<220> FEATURE:
<223> OTHER INFORMATION: Synthetic

<400> SEQUENCE: 67
caggcactat gcttgtccta gggatgagaa gatgagaaat cttagaacca                50

<210> SEQ ID NO 68
<211> LENGTH: 50
<212> TYPE: DNA
<213> ORGANISM: Artificial Sequence
<220> FEATURE:
<223> OTHER INFORMATION: Synthetic

<400> SEQUENCE: 68
cctcgtcttg gagtcttttg tcaataatgt aattctcttg ggaacacagg                50

<210> SEQ ID NO 69
<211> LENGTH: 50
<212> TYPE: DNA
<213> ORGANISM: Artificial Sequence
<220> FEATURE:
<223> OTHER INFORMATION: Synthetic

<400> SEQUENCE: 69
gggctgttcc agggatctga atatgctagt agactgaatg catccttcaa                50

<210> SEQ ID NO 70
<211> LENGTH: 50
<212> TYPE: DNA
<213> ORGANISM: Artificial Sequence
<220> FEATURE:
<223> OTHER INFORMATION: Synthetic

<400> SEQUENCE: 70
caccccattt tgagatgatg ggtccatcac taaagggaat tattggatct                50

```
<210> SEQ ID NO 71
<211> LENGTH: 46
<212> TYPE: DNA
<213> ORGANISM: Artificial Sequence
<220> FEATURE:
<223> OTHER INFORMATION: Synthetic

<400> SEQUENCE: 71
ttgaaaagtt gccaacccct gcccttcagg aaaatgtcct cggcct        46

<210> SEQ ID NO 72
<211> LENGTH: 42
<212> TYPE: DNA
<213> ORGANISM: Artificial Sequence
<220> FEATURE:
<223> OTHER INFORMATION: Synthetic

<400> SEQUENCE: 72
ctgccacgaa caccacgaag accgcgccgc tcctttggc cg        42

<210> SEQ ID NO 73
<211> LENGTH: 45
<212> TYPE: DNA
<213> ORGANISM: Artificial Sequence
<220> FEATURE:
<223> OTHER INFORMATION: Synthetic

<400> SEQUENCE: 73
tgagaactgc aatcctggtc atcatcccaa tggccgtgtc actga        45

<210> SEQ ID NO 74
<211> LENGTH: 35
<212> TYPE: DNA
<213> ORGANISM: Artificial Sequence
<220> FEATURE:
<223> OTHER INFORMATION: Synthetic

<400> SEQUENCE: 74
tccctggtct ggaaggactt cagcttccac tgtcg        35

<210> SEQ ID NO 75
<211> LENGTH: 39
<212> TYPE: DNA
<213> ORGANISM: Artificial Sequence
<220> FEATURE:
<223> OTHER INFORMATION: Synthetic

<400> SEQUENCE: 75
gaccgctgaa gcagatgttg gaggtgcaga tgtggggtt        39

<210> SEQ ID NO 76
<211> LENGTH: 46
<212> TYPE: DNA
<213> ORGANISM: Artificial Sequence
<220> FEATURE:
<223> OTHER INFORMATION: Synthetic

<400> SEQUENCE: 76
gggcaaagcg gtcacttgtg gccccaaagc cattccaatt gaagag        46

<210> SEQ ID NO 77
<211> LENGTH: 40
<212> TYPE: DNA
<213> ORGANISM: Artificial Sequence
<220> FEATURE:
<223> OTHER INFORMATION: Synthetic
```

<400> SEQUENCE: 77
gtcccggcaa ctcttgtaat actgggctgc ggagatcagg                                40

<210> SEQ ID NO 78
<211> LENGTH: 50
<212> TYPE: DNA
<213> ORGANISM: Artificial Sequence
<220> FEATURE:
<223> OTHER INFORMATION: Synthetic

<400> SEQUENCE: 78
agtcagctcc atcaaatact tggctaaagt gtgctgttca acatcaacct                     50

<210> SEQ ID NO 79
<211> LENGTH: 50
<212> TYPE: DNA
<213> ORGANISM: Artificial Sequence
<220> FEATURE:
<223> OTHER INFORMATION: Synthetic

<400> SEQUENCE: 79
cctctacatc aaaaccgttc aggttcaaag cccaggcttt ctgatgttcc                     50

<210> SEQ ID NO 80
<211> LENGTH: 50
<212> TYPE: DNA
<213> ORGANISM: Artificial Sequence
<220> FEATURE:
<223> OTHER INFORMATION: Synthetic

<400> SEQUENCE: 80
agacaagatc tcccaagtcc tccatagcag tgtattaagg tttttcggta                     50

<210> SEQ ID NO 81
<211> LENGTH: 41
<212> TYPE: DNA
<213> ORGANISM: Artificial Sequence
<220> FEATURE:
<223> OTHER INFORMATION: Synthetic

<400> SEQUENCE: 81
cctcagagca gcccactcac cacaaacgag atcctacaca g                             41

<210> SEQ ID NO 82
<211> LENGTH: 47
<212> TYPE: DNA
<213> ORGANISM: Artificial Sequence
<220> FEATURE:
<223> OTHER INFORMATION: Synthetic

<400> SEQUENCE: 82
cagccttggg caaagtcata aaccaccaca gtgtagaggt gaagtcc                       47

<210> SEQ ID NO 83
<211> LENGTH: 50
<212> TYPE: DNA
<213> ORGANISM: Artificial Sequence
<220> FEATURE:
<223> OTHER INFORMATION: Synthetic

<400> SEQUENCE: 83
atgtaaaact gtaggagcct gttgccacgc ggatgccatc aatcaacgtg                     50

<210> SEQ ID NO 84
<211> LENGTH: 50
<212> TYPE: DNA
<213> ORGANISM: Artificial Sequence
<220> FEATURE:
<223> OTHER INFORMATION: Synthetic

<400> SEQUENCE: 84
catccatcct cccaccccaa attcaactcc tgacccaata caaaagactt        50

<210> SEQ ID NO 85
<211> LENGTH: 50
<212> TYPE: DNA
<213> ORGANISM: Artificial Sequence
<220> FEATURE:
<223> OTHER INFORMATION: Synthetic

<400> SEQUENCE: 85
ctaggtgctt ggattgccga gttgagtttg ctggaaggga aatggggcgg        50

<210> SEQ ID NO 86
<211> LENGTH: 50
<212> TYPE: DNA
<213> ORGANISM: Artificial Sequence
<220> FEATURE:
<223> OTHER INFORMATION: Synthetic

<400> SEQUENCE: 86
ctcctcttcc ttggataaat tgcctggaat cagcgccccg ttagagcagg        50

<210> SEQ ID NO 87
<211> LENGTH: 48
<212> TYPE: DNA
<213> ORGANISM: Artificial Sequence
<220> FEATURE:
<223> OTHER INFORMATION: Synthetic

<400> SEQUENCE: 87
ctgatggcat tagattcctg cacgctaaga gttctccctc tacatctg        48

<210> SEQ ID NO 88
<211> LENGTH: 50
<212> TYPE: DNA
<213> ORGANISM: Artificial Sequence
<220> FEATURE:
<223> OTHER INFORMATION: Synthetic

<400> SEQUENCE: 88
cttggtgcgc cctacaattt ttggcaaagt ctttgctgat ggtgcaatac        50

<210> SEQ ID NO 89
<211> LENGTH: 35
<212> TYPE: DNA
<213> ORGANISM: Artificial Sequence
<220> FEATURE:
<223> OTHER INFORMATION: Synthetic

<400> SEQUENCE: 89
gggagattca gactcagagg cagccagagg ggaca        35

<210> SEQ ID NO 90
<211> LENGTH: 45
<212> TYPE: DNA
<213> ORGANISM: Artificial Sequence
<220> FEATURE:
<223> OTHER INFORMATION: Synthetic

<400> SEQUENCE: 90
ctttctccat gctgctgtcc tccaggaagt catggcaaat ttaca                45

<210> SEQ ID NO 91
<211> LENGTH: 50
<212> TYPE: DNA
<213> ORGANISM: Artificial Sequence
<220> FEATURE:
<223> OTHER INFORMATION: Synthetic

<400> SEQUENCE: 91
atttcacagg gcattctagt tcaaagggat ctcctgctaa gatggagtgt           50

<210> SEQ ID NO 92
<211> LENGTH: 50
<212> TYPE: DNA
<213> ORGANISM: Artificial Sequence
<220> FEATURE:
<223> OTHER INFORMATION: Synthetic

<400> SEQUENCE: 92
gatctgtttg ttctcctccg cctctggcat tttggagagg aagtgttcaa           50

<210> SEQ ID NO 93
<211> LENGTH: 50
<212> TYPE: DNA
<213> ORGANISM: Artificial Sequence
<220> FEATURE:
<223> OTHER INFORMATION: Synthetic

<400> SEQUENCE: 93
cagcactgtg agctggcttc attgagattt ggagtctctt taaattagca           50

<210> SEQ ID NO 94
<211> LENGTH: 50
<212> TYPE: DNA
<213> ORGANISM: Artificial Sequence
<220> FEATURE:
<223> OTHER INFORMATION: Synthetic

<400> SEQUENCE: 94
tgcctgtcca atcagatgac tctgggaaac gccaaacagg ctgaatcaat           50

<210> SEQ ID NO 95
<211> LENGTH: 50
<212> TYPE: DNA
<213> ORGANISM: Artificial Sequence
<220> FEATURE:
<223> OTHER INFORMATION: Synthetic

<400> SEQUENCE: 95
catttgggtg agacagagtc actgtactat tttcaatccc tgaccgaggg           50

<210> SEQ ID NO 96
<211> LENGTH: 45
<212> TYPE: DNA
<213> ORGANISM: Artificial Sequence
<220> FEATURE:
<223> OTHER INFORMATION: Synthetic

<400> SEQUENCE: 96
ttccgttgtg aatgacaggt tctgtaggag cagcacagta tttgg                45

<210> SEQ ID NO 97
<211> LENGTH: 50
<212> TYPE: DNA
<213> ORGANISM: Artificial Sequence
<220> FEATURE:
<223> OTHER INFORMATION: Synthetic

<400> SEQUENCE: 97
tagccacatg ggctgggtgt gatagtccta ctttaacgtg atgtatatag          50

<210> SEQ ID NO 98
<211> LENGTH: 35
<212> TYPE: DNA
<213> ORGANISM: Artificial Sequence
<220> FEATURE:
<223> OTHER INFORMATION: Synthetic

<400> SEQUENCE: 98
ctcccttggg ttgtcaggcc gctgggcaat aatag                          35

<210> SEQ ID NO 99
<211> LENGTH: 42
<212> TYPE: DNA
<213> ORGANISM: Artificial Sequence
<220> FEATURE:
<223> OTHER INFORMATION: Synthetic

<400> SEQUENCE: 99
ccctgttacc tgtgcaatct ctgagcccaa taacgcatct tc                  42

<210> SEQ ID NO 100
<211> LENGTH: 50
<212> TYPE: DNA
<213> ORGANISM: Artificial Sequence
<220> FEATURE:
<223> OTHER INFORMATION: Synthetic

<400> SEQUENCE: 100
tgcaggagga tataggaata acgacaggtg ccggggacta cgtaccatga          50

<210> SEQ ID NO 101
<211> LENGTH: 38
<212> TYPE: DNA
<213> ORGANISM: Artificial Sequence
<220> FEATURE:
<223> OTHER INFORMATION: Synthetic

<400> SEQUENCE: 101
gtggaagcag tagtcgtgcc aggattgtcc ttcatagg                       38

<210> SEQ ID NO 102
<211> LENGTH: 50
<212> TYPE: DNA
<213> ORGANISM: Artificial Sequence
<220> FEATURE:
<223> OTHER INFORMATION: Synthetic

<400> SEQUENCE: 102
cggtcaatgt tattcatggt ctctgctaat ttaggctgca aactccctgg          50

<210> SEQ ID NO 103
<211> LENGTH: 50
<212> TYPE: DNA
<213> ORGANISM: Artificial Sequence
<220> FEATURE:
<223> OTHER INFORMATION: Synthetic

```
<400> SEQUENCE: 103
tgtaaagtat ccaccttgag tgcttagctc aaaattgtat tggcactggg                  50

<210> SEQ ID NO 104
<211> LENGTH: 45
<212> TYPE: DNA
<213> ORGANISM: Artificial Sequence
<220> FEATURE:
<223> OTHER INFORMATION: Synthetic

<400> SEQUENCE: 104
cgctccaaga cgttgtgtgt tcgcctcttg acattctcct cggtg                       45

<210> SEQ ID NO 105
<211> LENGTH: 50
<212> TYPE: DNA
<213> ORGANISM: Artificial Sequence
<220> FEATURE:
<223> OTHER INFORMATION: Synthetic

<400> SEQUENCE: 105
caagctcttg ccgaacccTt cccagatcgt ttttcaacaa agtgttttct                  50

<210> SEQ ID NO 106
<211> LENGTH: 50
<212> TYPE: DNA
<213> ORGANISM: Artificial Sequence
<220> FEATURE:
<223> OTHER INFORMATION: Synthetic

<400> SEQUENCE: 106
aggtcctgtg gcagcatctc ggtcacttac cacaaggaaa caatgagttt                  50

<210> SEQ ID NO 107
<211> LENGTH: 50
<212> TYPE: DNA
<213> ORGANISM: Artificial Sequence
<220> FEATURE:
<223> OTHER INFORMATION: Synthetic

<400> SEQUENCE: 107
ctgcgggttt tttattatat tgatccagaa cctcagaggc aagctgttgg                  50

<210> SEQ ID NO 108
<211> LENGTH: 39
<212> TYPE: DNA
<213> ORGANISM: Artificial Sequence
<220> FEATURE:
<223> OTHER INFORMATION: Synthetic

<400> SEQUENCE: 108
agagcttctg gccattagga tgacagccta cccagatgt                              39

<210> SEQ ID NO 109
<211> LENGTH: 50
<212> TYPE: DNA
<213> ORGANISM: Artificial Sequence
<220> FEATURE:
<223> OTHER INFORMATION: Synthetic

<400> SEQUENCE: 109
cgatctccta gataacgtgg agggcctgct tcggatggat caagagacac                  50
```

<210> SEQ ID NO 110
<211> LENGTH: 50
<212> TYPE: DNA
<213> ORGANISM: Artificial Sequence
<220> FEATURE:
<223> OTHER INFORMATION: Synthetic

<400> SEQUENCE: 110
ccacccgcca cccccaggtt accattttaa gatattctgt caatgcttag        50

<210> SEQ ID NO 111
<211> LENGTH: 50
<212> TYPE: DNA
<213> ORGANISM: Artificial Sequence
<220> FEATURE:
<223> OTHER INFORMATION: Synthetic

<400> SEQUENCE: 111
tatataagcc ttgaagtact ccaccagacc ccggcaggtg attttattcc        50

<210> SEQ ID NO 112
<211> LENGTH: 50
<212> TYPE: DNA
<213> ORGANISM: Artificial Sequence
<220> FEATURE:
<223> OTHER INFORMATION: Synthetic

<400> SEQUENCE: 112
acatctgctt cagcttctgt gaagacttga cggaagcgga cgccgcaatg        50

<210> SEQ ID NO 113
<211> LENGTH: 45
<212> TYPE: DNA
<213> ORGANISM: Artificial Sequence
<220> FEATURE:
<223> OTHER INFORMATION: Synthetic

<400> SEQUENCE: 113
caatttgggc tagtgctggg tcccaagtca tgtatagcat atcac        45

<210> SEQ ID NO 114
<211> LENGTH: 46
<212> TYPE: DNA
<213> ORGANISM: Artificial Sequence
<220> FEATURE:
<223> OTHER INFORMATION: Synthetic

<400> SEQUENCE: 114
gccgcagcgg ctacagtgat gggaacgctt tggtctcatc aaatta        46

<210> SEQ ID NO 115
<211> LENGTH: 50
<212> TYPE: DNA
<213> ORGANISM: Artificial Sequence
<220> FEATURE:
<223> OTHER INFORMATION: Synthetic

<400> SEQUENCE: 115
cacgatgagg caggcccaat caatagagcc caaaatagcc atgtcaatgg        50

<210> SEQ ID NO 116
<211> LENGTH: 50
<212> TYPE: DNA
<213> ORGANISM: Artificial Sequence
<220> FEATURE:
<223> OTHER INFORMATION: Synthetic

<400> SEQUENCE: 116
gttctctctg gtatttcatt aatagagggt cgagcactct gaggtcttga      50

<210> SEQ ID NO 117
<211> LENGTH: 50
<212> TYPE: DNA
<213> ORGANISM: Artificial Sequence
<220> FEATURE:
<223> OTHER INFORMATION: Synthetic

<400> SEQUENCE: 117
gccctccttg ccttgcataa tcaacgggag ttttcccact agaatcctgt      50

<210> SEQ ID NO 118
<211> LENGTH: 50
<212> TYPE: DNA
<213> ORGANISM: Artificial Sequence
<220> FEATURE:
<223> OTHER INFORMATION: Synthetic

<400> SEQUENCE: 118
gatccacacc actatcccct ggaaatattg gttgtcctag taacagctca      50

<210> SEQ ID NO 119
<211> LENGTH: 50
<212> TYPE: DNA
<213> ORGANISM: Artificial Sequence
<220> FEATURE:
<223> OTHER INFORMATION: Synthetic

<400> SEQUENCE: 119
cagatgagga gagttcacat ttagccttt cagcagcttc ccgtaccctc      50

<210> SEQ ID NO 120
<211> LENGTH: 50
<212> TYPE: DNA
<213> ORGANISM: Artificial Sequence
<220> FEATURE:
<223> OTHER INFORMATION: Synthetic

<400> SEQUENCE: 120
ctctttgctg gcaatctcag ctcgtacctt ttgaagcaga gcaaaatcca      50

<210> SEQ ID NO 121
<211> LENGTH: 46
<212> TYPE: DNA
<213> ORGANISM: Artificial Sequence
<220> FEATURE:
<223> OTHER INFORMATION: Synthetic

<400> SEQUENCE: 121
cagctgctgg aacctttctc cagagcttca tgatttgttt gcaacg      46

<210> SEQ ID NO 122
<211> LENGTH: 50
<212> TYPE: DNA
<213> ORGANISM: Artificial Sequence
<220> FEATURE:
<223> OTHER INFORMATION: Synthetic

<400> SEQUENCE: 122
ttgacatcag agtcctttat gcagccagga cttactgatc atgaagcatg      50

<210> SEQ ID NO 123
<211> LENGTH: 50
<212> TYPE: DNA
<213> ORGANISM: Artificial Sequence
<220> FEATURE:
<223> OTHER INFORMATION: Synthetic

<400> SEQUENCE: 123
atctttatta actctaaata tctggcgcct ctgctgggta ctactggcat             50

<210> SEQ ID NO 124
<211> LENGTH: 46
<212> TYPE: DNA
<213> ORGANISM: Artificial Sequence
<220> FEATURE:
<223> OTHER INFORMATION: Synthetic

<400> SEQUENCE: 124
tgagcacaca ggttctctct gaatcgggtc aagctgattt ccaact                 46

<210> SEQ ID NO 125
<211> LENGTH: 50
<212> TYPE: DNA
<213> ORGANISM: Artificial Sequence
<220> FEATURE:
<223> OTHER INFORMATION: Synthetic

<400> SEQUENCE: 125
ctggacagga tctgtggtat ggtaacctgt acgggaagat ctggaaatcg             50

<210> SEQ ID NO 126
<211> LENGTH: 47
<212> TYPE: DNA
<213> ORGANISM: Artificial Sequence
<220> FEATURE:
<223> OTHER INFORMATION: Synthetic

<400> SEQUENCE: 126
cctattctca cacactagaa gacgggttag cagtttggca ctccatg                47

<210> SEQ ID NO 127
<211> LENGTH: 50
<212> TYPE: DNA
<213> ORGANISM: Artificial Sequence
<220> FEATURE:
<223> OTHER INFORMATION: Synthetic

<400> SEQUENCE: 127
tttatcatct tcccaacttg cagccatctg tgtagactgt tcatcatcac             50

<210> SEQ ID NO 128
<211> LENGTH: 46
<212> TYPE: DNA
<213> ORGANISM: Artificial Sequence
<220> FEATURE:
<223> OTHER INFORMATION: Synthetic

<400> SEQUENCE: 128
cggaacatct tccgaggagt tttgatgtag aggtggtaga gccact                 46

<210> SEQ ID NO 129
<211> LENGTH: 38
<212> TYPE: DNA
<213> ORGANISM: Artificial Sequence
<220> FEATURE:
<223> OTHER INFORMATION: Synthetic

<400> SEQUENCE: 129
tggaggtggg tgcagcttca tagagaatgc cctggttg                           38

<210> SEQ ID NO 130
<211> LENGTH: 50
<212> TYPE: DNA
<213> ORGANISM: Artificial Sequence
<220> FEATURE:
<223> OTHER INFORMATION: Synthetic

<400> SEQUENCE: 130
gggtcctgaa gtaagggagg tattggcgac tgtggaacag gagaaacagg              50

<210> SEQ ID NO 131
<211> LENGTH: 45
<212> TYPE: DNA
<213> ORGANISM: Artificial Sequence
<220> FEATURE:
<223> OTHER INFORMATION: Synthetic

<400> SEQUENCE: 131
gactctcggt gactggaacc atgcagtcga tagattcagc tctca                   45

<210> SEQ ID NO 132
<211> LENGTH: 44
<212> TYPE: DNA
<213> ORGANISM: Artificial Sequence
<220> FEATURE:
<223> OTHER INFORMATION: Synthetic

<400> SEQUENCE: 132
accagcagct cattaaagac cttctggaaa ttctcccca gcag                     44

<210> SEQ ID NO 133
<211> LENGTH: 50
<212> TYPE: DNA
<213> ORGANISM: Artificial Sequence
<220> FEATURE:
<223> OTHER INFORMATION: Synthetic

<400> SEQUENCE: 133
gctgctgcta ccttagaagg atgataatgc accatatcat agtcgatgag              50

<210> SEQ ID NO 134
<211> LENGTH: 50
<212> TYPE: DNA
<213> ORGANISM: Artificial Sequence
<220> FEATURE:
<223> OTHER INFORMATION: Synthetic

<400> SEQUENCE: 134
accctctggc gcattttgtg gttttccact gagccgaagg atcttggctt              50

<210> SEQ ID NO 135
<211> LENGTH: 49
<212> TYPE: DNA
<213> ORGANISM: Artificial Sequence
<220> FEATURE:
<223> OTHER INFORMATION: Synthetic

<400> SEQUENCE: 135
ctctggtgat attgtgtcag acaggtatag taggagacaa gcagctaca               49

<210> SEQ ID NO 136
<211> LENGTH: 44
<212> TYPE: DNA
<213> ORGANISM: Artificial Sequence
<220> FEATURE:
<223> OTHER INFORMATION: Synthetic

<400> SEQUENCE: 136
tgacttcaga gatggcacat ggctaaatgg cagcccagtg gaga          44

<210> SEQ ID NO 137
<211> LENGTH: 50
<212> TYPE: DNA
<213> ORGANISM: Artificial Sequence
<220> FEATURE:
<223> OTHER INFORMATION: Synthetic

<400> SEQUENCE: 137
atttacaact gtccactagt tgggtcaggt cagccaaatc aactatctga    50

<210> SEQ ID NO 138
<211> LENGTH: 50
<212> TYPE: DNA
<213> ORGANISM: Artificial Sequence
<220> FEATURE:
<223> OTHER INFORMATION: Synthetic

<400> SEQUENCE: 138
ttggccagac agaattacca agttactgct gtttaatttg ccatccgtcc    50

<210> SEQ ID NO 139
<211> LENGTH: 50
<212> TYPE: DNA
<213> ORGANISM: Artificial Sequence
<220> FEATURE:
<223> OTHER INFORMATION: Synthetic

<400> SEQUENCE: 139
gagaaacatc taatagcgca catctgggca cccacactct gcttcagttg    50

<210> SEQ ID NO 140
<211> LENGTH: 47
<212> TYPE: DNA
<213> ORGANISM: Artificial Sequence
<220> FEATURE:
<223> OTHER INFORMATION: Synthetic

<400> SEQUENCE: 140
caacggaggc tcagtccaga cagggattaa ccgacttgtg ctggtat       47

<210> SEQ ID NO 141
<211> LENGTH: 50
<212> TYPE: DNA
<213> ORGANISM: Artificial Sequence
<220> FEATURE:
<223> OTHER INFORMATION: Synthetic

<400> SEQUENCE: 141
ctgatctgag tcatggcttc gttaaagctg gacatctggg aagacagttc    50

<210> SEQ ID NO 142
<211> LENGTH: 50
<212> TYPE: DNA
<213> ORGANISM: Artificial Sequence
<220> FEATURE:
<223> OTHER INFORMATION: Synthetic

<400> SEQUENCE: 142
gtctttctct tcacctactg atggtttagg cgtgtgcatg gctttgcctg            50

<210> SEQ ID NO 143
<211> LENGTH: 50
<212> TYPE: DNA
<213> ORGANISM: Artificial Sequence
<220> FEATURE:
<223> OTHER INFORMATION: Synthetic

<400> SEQUENCE: 143
ttttcagcta aaacctgata agccagcttt ctgacagcct ctttcacatc            50

<210> SEQ ID NO 144
<211> LENGTH: 50
<212> TYPE: DNA
<213> ORGANISM: Artificial Sequence
<220> FEATURE:
<223> OTHER INFORMATION: Synthetic

<400> SEQUENCE: 144
tccccgagtc ttctgcaatc cagtcctctt agaaattggt ttctctcttt            50

<210> SEQ ID NO 145
<211> LENGTH: 46
<212> TYPE: DNA
<213> ORGANISM: Artificial Sequence
<220> FEATURE:
<223> OTHER INFORMATION: Synthetic

<400> SEQUENCE: 145
taatgatggt tgggaggtga gggaagtcag aggccttttc taggat                46

<210> SEQ ID NO 146
<211> LENGTH: 50
<212> TYPE: DNA
<213> ORGANISM: Artificial Sequence
<220> FEATURE:
<223> OTHER INFORMATION: Synthetic

<400> SEQUENCE: 146
tgttgttcca ttgagcttgc accaagtcac atgaggcctg ttagcacagt            50

<210> SEQ ID NO 147
<211> LENGTH: 50
<212> TYPE: DNA
<213> ORGANISM: Artificial Sequence
<220> FEATURE:
<223> OTHER INFORMATION: Synthetic

<400> SEQUENCE: 147
ttcacatctg tggcacagag ggcaacgaag gtctgcgcgt gtttgcggat            50

<210> SEQ ID NO 148
<211> LENGTH: 45
<212> TYPE: DNA
<213> ORGANISM: Artificial Sequence
<220> FEATURE:
<223> OTHER INFORMATION: Synthetic

<400> SEQUENCE: 148
tgcaaattct tttggttcgg cagcttgcta ggtgaccggg gcaca                 45

<210> SEQ ID NO 149
<211> LENGTH: 50
<212> TYPE: DNA
<213> ORGANISM: Artificial Sequence
<220> FEATURE:
<223> OTHER INFORMATION: Synthetic

<400> SEQUENCE: 149
attcatcgga accgaactta ggttgagtac cctaattttc cttgcaccca            50

<210> SEQ ID NO 150
<211> LENGTH: 50
<212> TYPE: DNA
<213> ORGANISM: Artificial Sequence
<220> FEATURE:
<223> OTHER INFORMATION: Synthetic

<400> SEQUENCE: 150
ctgattctta gggtctttga tatggaggat gctggtaaca gacgtggtcc            50

<210> SEQ ID NO 151
<211> LENGTH: 50
<212> TYPE: DNA
<213> ORGANISM: Artificial Sequence
<220> FEATURE:
<223> OTHER INFORMATION: Synthetic

<400> SEQUENCE: 151
ctgataatca ctatcactga tttccgaacc atttgttcct gttccttggc            50

<210> SEQ ID NO 152
<211> LENGTH: 50
<212> TYPE: DNA
<213> ORGANISM: Artificial Sequence
<220> FEATURE:
<223> OTHER INFORMATION: Synthetic

<400> SEQUENCE: 152
ggttcttcac tgccgttgtg tgtctcatcc actgtctgat tcagcttttt            50

<210> SEQ ID NO 153
<211> LENGTH: 39
<212> TYPE: DNA
<213> ORGANISM: Artificial Sequence
<220> FEATURE:
<223> OTHER INFORMATION: Synthetic

<400> SEQUENCE: 153
cgcagaggcc gatgcgactc tttcctgctg cttgaagaa                       39

<210> SEQ ID NO 154
<211> LENGTH: 40
<212> TYPE: DNA
<213> ORGANISM: Artificial Sequence
<220> FEATURE:
<223> OTHER INFORMATION: Synthetic

<400> SEQUENCE: 154
ttagcacata ccacagcacg ggtcctgagt ccacatcatt                      40

<210> SEQ ID NO 155
<211> LENGTH: 50
<212> TYPE: DNA
<213> ORGANISM: Artificial Sequence
<220> FEATURE:
<223> OTHER INFORMATION: Synthetic

```
<400> SEQUENCE: 155
agacaggcac gatatatact actagagaat gcgcagtttc aaaccacagt        50

<210> SEQ ID NO 156
<211> LENGTH: 50
<212> TYPE: DNA
<213> ORGANISM: Artificial Sequence
<220> FEATURE:
<223> OTHER INFORMATION: Synthetic

<400> SEQUENCE: 156
tggtggaaaa caaagcgctt gttggccaga ttcacggagc attttttgca        50

<210> SEQ ID NO 157
<211> LENGTH: 50
<212> TYPE: DNA
<213> ORGANISM: Artificial Sequence
<220> FEATURE:
<223> OTHER INFORMATION: Synthetic

<400> SEQUENCE: 157
cttcgacttc agagagccaa gcctcattct tatggatttc cattcgtagg        50

<210> SEQ ID NO 158
<211> LENGTH: 50
<212> TYPE: DNA
<213> ORGANISM: Artificial Sequence
<220> FEATURE:
<223> OTHER INFORMATION: Synthetic

<400> SEQUENCE: 158
aatgctttgt ctggtttccc atagggctgt tgctgattcc agctttaaaa        50

<210> SEQ ID NO 159
<211> LENGTH: 50
<212> TYPE: DNA
<213> ORGANISM: Artificial Sequence
<220> FEATURE:
<223> OTHER INFORMATION: Synthetic

<400> SEQUENCE: 159
tctggtcacg cagggcaaaa aagctccgtt ttagctcgtt cctcctctgg        50

<210> SEQ ID NO 160
<211> LENGTH: 50
<212> TYPE: DNA
<213> ORGANISM: Artificial Sequence
<220> FEATURE:
<223> OTHER INFORMATION: Synthetic

<400> SEQUENCE: 160
taaaacctca atttccttcc tctgtgcatc gtgagtactt tctgcagctt        50

<210> SEQ ID NO 161
<211> LENGTH: 50
<212> TYPE: DNA
<213> ORGANISM: Artificial Sequence
<220> FEATURE:
<223> OTHER INFORMATION: Synthetic

<400> SEQUENCE: 161
cgccaaggag catgttgaaa gtccaaaata gcaccattca tcagtgtctc        50
```

-continued

```
<210> SEQ ID NO 162
<211> LENGTH: 50
<212> TYPE: DNA
<213> ORGANISM: Artificial Sequence
<220> FEATURE:
<223> OTHER INFORMATION: Synthetic

<400> SEQUENCE: 162
acaaggagca ccgcatccat gttatcagat gtttgcacgt cgaacacaaa          50

<210> SEQ ID NO 163
<211> LENGTH: 50
<212> TYPE: DNA
<213> ORGANISM: Artificial Sequence
<220> FEATURE:
<223> OTHER INFORMATION: Synthetic

<400> SEQUENCE: 163
ctggatgcgg agaacctctg acgagggagg attgttcggg tcatacacga          50

<210> SEQ ID NO 164
<211> LENGTH: 50
<212> TYPE: DNA
<213> ORGANISM: Artificial Sequence
<220> FEATURE:
<223> OTHER INFORMATION: Synthetic

<400> SEQUENCE: 164
tcctgctttc ccgtatcccc agggtgagat tctccagata aaacttgtag          50

<210> SEQ ID NO 165
<211> LENGTH: 50
<212> TYPE: DNA
<213> ORGANISM: Artificial Sequence
<220> FEATURE:
<223> OTHER INFORMATION: Synthetic

<400> SEQUENCE: 165
tataataaac agcaggatcc ccactggcta ggctgccgtg cacacagcac          50
```

EVALUATION OF MANTLE CELL LYMPHOMA AND METHODS RELATED THERETO

CROSS-REFERENCE TO RELATED APPLICATIONS

This patent application is a U.S. National Phase of International Patent Application No. PCT/US2017/028628, filed Apr. 20, 2017, which claims the benefit of U.S. Provisional Patent Application No. 62/325,213, filed Apr. 20, 2016, each of which is incorporated by reference in its entirety herein.

STATEMENT REGARDING FEDERALLY SPONSORED RESEARCH AND DEVELOPMENT

This invention was made with government support under grant no. CA157581 awarded by the National Institutes of Health. This invention was made with government support under project number ZIA BC 011006-05 by the National Institutes of Health, National Cancer Institute. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 35,279 Byte ASCII (Text) file named "740542_ST25.txt" created on Oct. 18, 2018.

BACKGROUND OF THE INVENTION

Mantle cell lymphoma (MCL) is an incurable B-cell malignancy with a broad array of clinical and biological features. The vast majority of cases harbor the t(11;14)(q13;q32) translocation leading to overexpression of cyclin D1 and dysregulation of the cell cycle. Although most patients have aggressive disease that requires immediate treatment, there is a group of patients in whom the disease is indolent and can be observed for years without treatment. Recently, it was recognized that MCL encompasses two subtypes, each with distinct biology: conventional MCL and a leukemic non-nodal variant characterized by lymphocytosis, splenomegaly, no (or minimal) lymphadenopathy and an indolent clinical course. There is no universally accepted treatment regimen for MCL at this time. Most centers make treatment decisions on the basis of the patient's age, with intensive regimens offered to younger patients.

A number of prognostic tools have been developed for MCL. The most prominent is the MCL International Prognostic Index (MIPI), which combines clinical and laboratory values to assign patients to low-, intermediate-, or high-risk groups. MIPI has been validated in randomized clinical trials. In 2003, the Lymphoma/Leukemia Molecular Profiling Project (LLMPP) consortium performed gene expression profiling on MCL and demonstrated that a coordinated signature of gene expression associated with proliferation was the strongest molecular predictor of survival and integrated the prognostic power of other molecular markers.

However, this proliferation signature, requiring fresh frozen (FF) material and using a microarray-based platform, has not penetrated clinical practice. Ki-67 proliferation index (PI), measured using immunohistochemistry (IHC), has been proposed as a surrogate measure of the proliferation signature and has been shown to be prognostic in numerous studies, both alone and in combination with the MIPI. However, serious concerns have been raised regarding the analytic validity of the Ki-67 PI in lymphoma and other malignancies, particularly regarding inter-laboratory and inter-observer variability.

Recently, technologies have been developed to reliably quantify gene expression in RNA from formalin-fixed paraffin-embedded (FFPE) tissue, allowing the development of clinically relevant, intermediate density, gene expression-based assays. Better methods using these technologies are needed to provide a consistent, reproducible score that better predicts MCL prognosis. The present invention provides such methods.

BRIEF SUMMARY OF THE INVENTION

The present invention provides a method of determining a survival predictor score of a human subject having MCL, which method comprises obtaining or providing a biopsy sample from the subject; isolating RNA gene expression product from the biopsy sample; obtaining gene expression data from the RNA gene expression product, wherein the gene expression data comprises signal values that represent expression levels for one or more genes as described herein; and determining a survival predictor score from the gene expression data, wherein the survival predictor score is determined by calculating a multiplication product for each of the one or more genes, wherein the multiplication product is the mathematical product of the signal value or log transformation of the signal value of a gene with a coefficient value for that gene, the coefficient value for the gene as described herein, and summing the multiplication products when there is more than one multiplication product.

The present invention also provides a method of predicting the survival outcome of a human subject having MCL comprising determining the survival predictor score of the subject as described herein; and classifying the subject as belonging to one of the following groups based on the survival predictor score: good prognosis, intermediate prognosis, and poor prognosis.

The present invention also provides a method of selecting a treatment for a human subject having MCL comprising classifying the subject as described herein; selecting a treatment for the subject based on the subject's classification; and providing the treatment to the subject.

DETAILED DESCRIPTION OF THE INVENTION

Figure 1:
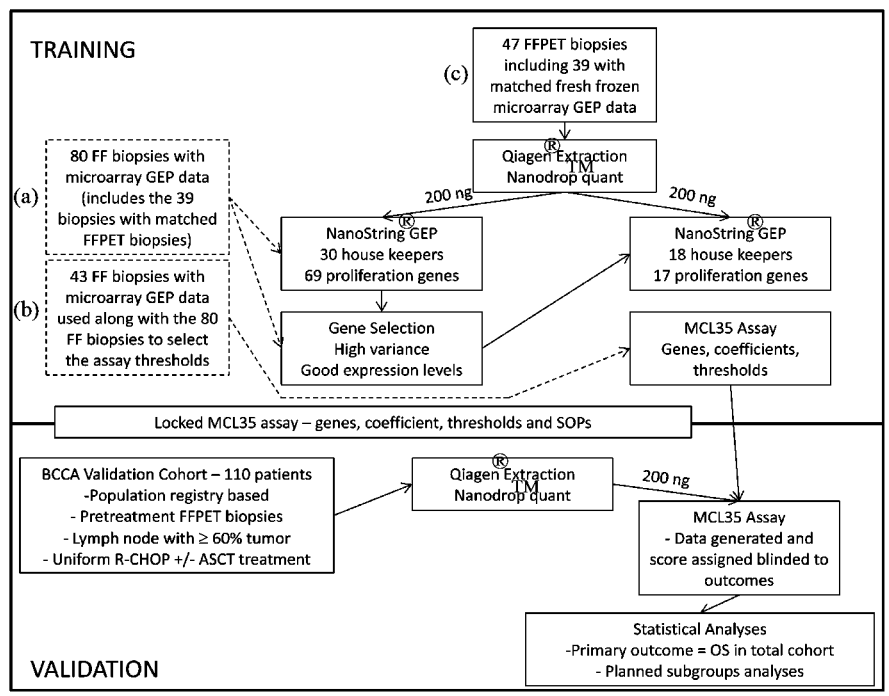
FIG. 1 is a flowchart showing validation of a method of determining a survival predictor score in accordance with embodiments of the invention. The 80 FF biopsies are from Rosenwald et al., Cancer Cell, 3:185-197 (2003), incorporated by reference herein.

The present invention provides a method of determining a survival predictor score of a human subject having MCL, which method comprises obtaining or providing a biopsy sample from the subject; isolating RNA gene expression product from the biopsy sample; obtaining gene expression data from the RNA gene expression product, wherein the gene expression data comprises signal values that represent expression levels for one or more genes of Table 1 below; and determining a survival predictor score from the gene expression data, wherein the survival predictor score is determined by calculating a multiplication product for each of the one or more genes, wherein the multiplication product is the mathematical product of the log transformation of the signal value of a gene with a coefficient value for that gene, and summing the multiplication products when there is more than one multiplication product.

In another embodiment, the present invention also provides a method of determining a survival predictor score of a human subject having MCL, which method comprises obtaining or providing a biopsy sample from the subject; isolating RNA gene expression product from the biopsy sample; obtaining gene expression data from the RNA gene expression product, wherein the gene expression data comprises signal values that represent expression levels for one or more genes of Table 1 below; and determining a survival predictor score from the gene expression data, wherein the survival predictor score is determined by calculating a multiplication product for each of the one or more genes, wherein the multiplication product is the mathematical product of the signal value of a gene with a coefficient value for that gene, and summing the multiplication products when there is more than one multiplication product.

In another embodiment, the present invention also provides a method of determining a survival predictor score of a human subject having MCL, which method comprises obtaining or providing a biopsy sample from the subject; isolating RNA gene expression product from the biopsy sample; obtaining gene expression data from the RNA gene expression product, wherein the gene expression data comprises signal values that represent expression levels for each gene of Table 1 below; and determining a survival predictor score from the gene expression data, wherein the survival predictor score is determined by calculating a multiplication product for each gene of Table 1 below, wherein the multiplication product is the mathematical product of the log transformation of the signal value of a gene with a coefficient value for that gene, and summing the multiplication products.

In another embodiment, the present invention also provides a method of determining a survival predictor score of a human subject having MCL, which method comprises obtaining or providing a biopsy sample from the subject; isolating RNA gene expression product from the biopsy sample; obtaining gene expression data from the RNA gene expression product, wherein the gene expression data comprises signal values that represent expression levels for each gene of Table 1 below; and determining a survival predictor score from the gene expression data, wherein the survival predictor score is determined by calculating a multiplication product for each gene of Table 1 below, wherein the multiplication product is the mathematical product of the signal value of a gene with a coefficient value for that gene, and summing the multiplication products.

In another embodiment, the present invention provides a method of determining a survival predictor score of a human subject having MCL, which method comprises obtaining or providing a biopsy sample from the subject; isolating RNA gene expression product from the biopsy sample; obtaining gene expression data from the RNA gene expression product, wherein the gene expression data comprises signal values that represent expression levels for one or more genes of Table 1 below; and determining a survival predictor score from the gene expression data, wherein the survival predictor score is determined by calculating a multiplication product for each of the one or more genes, wherein the multiplication product is the mathematical product of the log transformation of the signal value of a gene with a coefficient value for that gene, the coefficient value for the gene as listed in Table 1 below, and summing the multiplication products when there is more than one multiplication product.

In another embodiment, the present invention also provides a method of determining a survival predictor score of a human subject having MCL, which method comprises obtaining or providing a biopsy sample from the subject; isolating RNA gene expression product from the biopsy sample; obtaining gene expression data from the RNA gene expression product, wherein the gene expression data comprises signal values that represent expression levels for one or more genes of Table 1 below; and determining a survival predictor score from the gene expression data, wherein the survival predictor score is determined by calculating a multiplication product for each of the one or more genes, wherein the multiplication product is the mathematical product of the signal value of a gene with a coefficient value for that gene, the coefficient value for the gene as listed in Table 1 below, and summing the multiplication products when there is more than one multiplication product.

In another embodiment, the present invention also provides a method of determining a survival predictor score of a human subject having MCL, which method comprises obtaining or providing a biopsy sample from the subject; isolating RNA gene expression product from the biopsy sample; obtaining gene expression data from the RNA gene expression product, wherein the gene expression data comprises signal values that represent expression levels for each gene of Table 1 below; and determining a survival predictor score from the gene expression data, wherein the survival predictor score is determined by calculating a multiplication product for each gene of Table 1 below, wherein the multiplication product is the mathematical product of the log transformation of the signal value of a gene with a coefficient value for that gene, the coefficient value for the gene listed in Table 1 below, and summing the multiplication products.

In another embodiment, the present invention also provides a method of determining a survival predictor score of a human subject having MCL, which method comprises obtaining or providing a biopsy sample from the subject; isolating RNA gene expression product from the biopsy sample; obtaining gene expression data from the RNA gene expression product, wherein the gene expression data comprises signal values that represent expression levels for each gene of Table 1 below; and determining a survival predictor score from the gene expression data, wherein the survival predictor score is determined by calculating a multiplication product for each gene of Table 1 below, wherein the multiplication product is the mathematical product of the signal value of a gene with a coefficient value for that gene, the coefficient value for the gene listed in Table 1 below, and summing the multiplication products.

The inventive method comprises isolating sufficient RNA gene expression product from a human subject, e.g., from a biopsy sample from a subject, such as from fresh tissue, a snap-frozen biopsy sample from a subject, or a formalin-fixed and paraffin-embedded (FFPE) biopsy sample from a subject. As understood by one of ordinary skill in the art, the phrase "a snap-frozen biopsy sample from a subject" means that a biopsy sample is first taken from a subject and afterwards snap-frozen, and the phrase "obtaining or providing a formalin-fixed and paraffin-embedded (FFPE) biopsy sample from the subject" means that a biopsy sample is first taken from a subject and afterwards fixed with formalin and embedded in paraffin. For MCL samples, for example, since the tumor can be in any anatomic location, the biopsy can be from any tissue.

The gene expression product is RNA, for example, total cellular mRNA. The RNA gene expression product may be obtained from the subject in any suitable manner. For example, one or more biopsy samples may be obtained from a patient that has been diagnosed as having MCL, and the biopsy samples can be formalin-fixed and paraffin-embedded using protocols that are known in the art or are commercially available (see, e.g., Keirnan, J. (ed.), *Histological and Histochemical Methods: Theory and Practice*, 4th edition, Cold Spring Harbor Laboratory Press (2008), incorporated herein by reference. The RNA gene expression product can be extracted from an FFPE biopsy sample using methods that are known in the art or are commercially available (see, e.g., Huang et al., *Cancer Epidemiol Biomarkers Prev.*, 19: 973-977 (2010), incorporated herein by reference; QIAGEN® AllPREP DNA/RNA FFPE Kit, RNAEASY™ FFPE Kit (QIAGEN®, Venlo, Netherlands)).

The inventive method further comprises obtaining gene expression data from the isolated RNA gene expression product, wherein the gene expression data comprises data for genes in a gene expression signature. The phrase "gene expression data" as used herein refers to information regarding the relative or absolute level of expression of RNA gene expression product. "Gene expression data" may be acquired for an individual cell, or for a group of cells such as a tumor or biopsy sample. Any effective method of quantifying the expression of at least one gene, gene set, or group of gene sets may be used to acquire gene expression data for use in the invention. For example, gene expression data may be measured or estimated using one or more microarrays.

Nucleic acid microarrays generally comprise nucleic acid probes derived from individual genes and placed in an ordered array on a support. This support may be, for example, a glass slide, a nylon membrane, or a silicon wafer. Gene expression patterns in a sample are obtained by hybridizing the microarray with the RNA gene expression product from the sample. The RNA gene expression product from a sample is labeled with a radioactive, fluorescent, or other label to allow for detection. Following hybridization, the microarray is washed, and hybridization of RNA gene expression product to each nucleic acid probe on the microarray is detected and quantified using a detection device such as a phosphorimager or scanning confocal microscope.

The microarray may be a cDNA microarray or an oligonucleotide microarray. cDNA arrays consist of hundreds or thousands of cDNA probes immobilized on a solid support, and are described in detail in, e.g., Southern et al., *Genomics*, 13: 1008-1017 (1992); Southern et al., *Nucl. Acids. Res.*, 22: 1368-1373 (1994); Gress et al., *Oncogene*, 13: 1819-1830 (1996); Pietu et al., *Genome Res.*, 6: 492-503 (1996); Schena et al., *Science*, 270: 467-470 (1995); DeRisi et al., *Nat. Genet.*, 14: 457-460 (1996); Schena et al., *Proc. Natl. Acad. Sci. USA*, 93: 10614-10619 (1996); Shalon et al., *Genome Res.*, 6: 639-645 (1996); DeRisi et al., *Science*, 278: 680-686 (1997); Heller et al., *Proc. Natl. Acad. Sci. USA*, 94: 2150-2155 (1997); and Lashkari et al., *Proc. Natl. Acad. Sci. USA*, 94: 13057-13062 (1997). Oligonucleotide arrays differ from cDNA arrays in that the probes are 20- to 25-mer oligonucleotides. Oligonucleotide arrays are generally produced by in situ oligonucleotide synthesis in conjunction with photolithographic masking techniques (see, e.g., Pease et al., *Proc. Natl. Acad. Sci. USA*, 91: 5022-5026 (1994); Lipshutz et al., *Biotechniques*, 19: 442-447 (1995); Chee et al., *Science*, 274: 610-14 (1996); Lockhart et al., *Nat. Biotechnol.*, 14: 1675-1680 (1996); and Wodicka et al., *Nat. Biotechnol.*, 15: 1359-1367 (1997)). The solid support for oligonucleotide arrays is typically a glass or silicon surface.

Methods and techniques applicable to array synthesis and use have been described in, for example, U.S. Pat. Nos. 5,143,854, 5,242,974, 5,252,743, 5,324,633, 5,384,261, 5,424,186, 5,445,934, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, and 6,410,229, and U.S. Patent Application Publication 2003/0104411. Techniques for the synthesis of microarrays using mechanical synthesis methods are described in, for example, U.S. Pat. Nos. 5,384,261 and 6,040,193. Microarrays may be nucleic acids on beads, gels, polymeric surfaces, fibers such as fiber optics, glass or any other appropriate substrate (see, e.g., U.S. Pat. Nos. 5,708,153, 5,770,358, 5,789,162, 5,800,992, and 6,040,193).

Microarrays may be packaged in such a manner as to allow for diagnostic use, or they may be an all-inclusive device (see, e.g., U.S. Pat. Nos. 5,856,174 and 5,922,591). Microarrays directed to a variety of purposes are commercially available from, e.g., Affymetrix® (Attymetrix®, Santa Clara, Calif., USA).

In an embodiment, the signal value comprises digital counts. Gene expression data can be obtained and analyzed using a variety of digital methods known in the art, such as, for example, serial analysis of gene expression (SAGE) (see, e.g., Velculescu et al., *Science*, 270(5235): 484-487 (1995)), SuperSAGE (see e.g., Matsumura et al., *Proc. Natl. Acad. Sci. USA*, 100 (26): 15718-15723 (2003)), digital northern analysis (see, e.g., Cao et al., *Breast Cancer Research*, 10: R91 (2008)), and RNA-seq (see, e.g., Mortazavi et al. *Nat Methods*, 5(7):621-628 (2008)). In an embodiment, the RNA gene expression data is obtained using a NanoString Technologies® nCounter® assay available from NanoString Technologies®, Inc. (Seattle, Wash., USA).

The nCounter® assay can detect the expression of up to 800 genes in a single reaction with high sensitivity and linearity across a broad range of expression levels. The nCounter® assay is based on direct digital detection of mRNA molecules of interest using target-specific, color-coded probe pairs, and does not require the conversion of mRNA to cDNA by reverse transcription or the amplification of the resulting cDNA by PCR. Each target gene of interest is detected using a pair of reporter and capture probes carrying 35- to 50-nucleotide target-specific sequences. In addition, each reporter probe carries a unique color code at the 5' end that enables the molecular barcoding of the genes of interest, while the capture probes all carry a biotin label at the 3' end that provides a molecular handle for attachment of target genes to facilitate downstream digital detection. After solution-phase hybridization between target mRNA and reporter-capture probe pairs, excess probes are removed and the probe/target complexes are aligned and immobilized in an nCounter® cartridge, which is then placed in a digital analyzer for image acquisition and data processing. Hundreds of thousands of color codes designating mRNA targets of interest are directly imaged on the surface of the cartridge. The expression level of a gene is measured by counting the number of times the color-coded barcode for that gene is detected, and the barcode counts are then tabulated. NanoString Technologies® technology and analysis of digital gene expression data is described in detail in, e.g., Kulkarni, M. M., "Digital Multiplexed Gene Expression Analysis Using the NanoString Technologies® nCounter® System," *Current Protocols in Molecular Biology.* 94: 25B.10.1-25B.10.17 (2011), incorporated herein by reference; Geiss et al., *Nature Biotechnology*, 26: 317-325 (2008), incorporated herein by reference; and U.S. Pat. No. 7,919,237, incorporated herein by reference.

The term "gene expression signature" as used herein refers to a group of coordinately expressed genes. The genes making up a particular signature may be expressed in a specific cell lineage, stage of differentiation, or during a particular biological response. The genes may reflect biological aspects of the tumors in which they are expressed, such as the cell of origin of the cancer, the nature of the non-malignant cells in the biopsy, and the oncogenic mechanisms responsible for the cancer (see, e.g., Shaffer et al., *Immunity*, 15: 375-385 (2001), incorporated herein by reference). Examples of gene expression signatures include lymph node (see Shaffer et al., supra), proliferation (see, e.g., Rosenwald et al., *New Engl. J. Med.*, 346: 1937-1947 (2002), incorporated herein by reference), MHC class II, ABC DLBCL high, B-cell differentiation, T-cell, macrophage, immune response-1, immune response-2, and germinal center B cell.

Genes of a gene expression signature of the present invention are shown in Table 1 with their respective coefficient values and target DNA sequences. When gene expression is detected using RNA, the sequences detected are the RNA sequences of the DNA target sequences, where the DNA sequences have thymine replaced with uracil.

TABLE 1

| Human Gene | Anti-Proliferation/ Housekeeper/ Proliferation Gene | Coeff. Value | GenBank Accession | Position | Target DNA (SEQ ID NO:) | Capture Probe (SEQ ID NO:) | Reporter Probe (SEQ ID NO:) |
|---|---|---|---|---|---|---|---|
| ATL1 | Anti-Proliferation | −19.64 | NM_015915.4 | 1141-1240 | 1 | 56 | 111 |
| FMNL3 | Anti-Proliferation | −21.46 | NM_175736.4 | 2434-2533 | 2 | 57 | 112 |
| GLIPR1 | Anti-Proliferation | −29.91 | NM_006851.2 | 256-355 | 3 | 58 | 113 |
| ZDHHC21 | Anti-Proliferation | −23.47 | NM_178566.4 | 713-812 | 4 | 59 | 114 |
| CHD4 | Housekeeper | 0.75 | NM_001273.2 | 2681-2780 | 5 | 60 | 115 |
| ERBB2IP | Housekeeper | 0.75 | NM_018695.2 | 3676-3775 | 6 | 61 | 116 |
| GIT2 | Housekeeper | 0.75 | NM_057169.2 | 606-705 | 7 | 62 | 117 |
| GSK3B | Housekeeper | 0.75 | NM_002093.2 | 926-1025 | 8 | 63 | 118 |
| HSPA9 | Housekeeper | 0.75 | NM_004134.4 | 976-1075 | 9 | 64 | 119 |
| IK | Housekeeper | 0.75 | NM_006083.3 | 557-656 | 10 | 65 | 120 |
| MLL2 | Housekeeper | 0.75 | NM_003482.3 | 6071-6170 | 11 | 66 | 121 |
| NEU3 | Housekeeper | 0.75 | NM_006656.5 | 1841-1940 | 12 | 67 | 122 |
| R3HDM1 | Housekeeper | 0.75 | NM_015361.2 | 1276-1375 | 13 | 68 | 123 |
| RANBP9 | Housekeeper | 0.75 | NM_005493.2 | 2001-2100 | 14 | 69 | 124 |
| RC3H2 | Housekeeper | 0.75 | NM_018835.2 | 2911-3010 | 15 | 70 | 125 |
| TRIM56 | Housekeeper | 0.75 | NM_030961.1 | 2571-2670 | 16 | 71 | 126 |
| UBXN4 | Housekeeper | 0.75 | NM_014607.3 | 344-443 | 17 | 72 | 127 |
| VAC14 | Housekeeper | 0.75 | NM_018052.3 | 1476-1575 | 18 | 73 | 128 |
| VRK3 | Housekeeper | 0.75 | NM_016440.3 | 821-920 | 19 | 74 | 129 |
| WAC | Housekeeper | 0.75 | NM_100486.2 | 756-855 | 20 | 75 | 130 |
| WDR55 | Housekeeper | 0.75 | NM_017706.4 | 816-915 | 21 | 76 | 131 |
| ZNF598 | Housekeeper | 0.75 | NM_178167.2 | 2369-2468 | 22 | 77 | 132 |
| CCNB2 | Proliferation | 6.01 | NM_004701.2 | 981-1080 | 23 | 78 | 133 |
| CDC20 | Proliferation | 6.35 | NM_001255.2 | 431-530 | 24 | 79 | 134 |
| CDKN3 | Proliferation | 6.4 | NM_005192.3 | 511-610 | 25 | 80 | 135 |
| E2F2 | Proliferation | 6.02 | NM_004091.2 | 3606-3705 | 26 | 81 | 136 |
| ESPL1 | Proliferation | 6.5 | NM_012291.4 | 1286-1385 | 27 | 82 | 137 |
| FAM83D | Proliferation | 5.92 | NM_030919.2 | 866-965 | 28 | 83 | 138 |
| FOXM1 | Proliferation | 6.55 | NM_021953.2 | 3209-3308 | 29 | 84 | 139 |
| H2AFX | Proliferation | 6.08 | NM_002105.2 | 1393-1492 | 30 | 85 | 140 |
| KIF2C | Proliferation | 6.19 | NM_006845.3 | 1941-2040 | 31 | 86 | 141 |
| MKI67 | Proliferation | 6.65 | NM_002417.2 | 4021-4120 | 32 | 87 | 142 |
| NCAPG | Proliferation | 6.44 | NM_022346.3 | 781-880 | 33 | 88 | 143 |
| TOP2A | Proliferation | 6.46 | NM_001067.2 | 5377-5476 | 34 | 89 | 144 |
| ZWINT | Proliferation | 5.41 | NM_007057.3 | 851-950 | 35 | 90 | 145 |

In an embodiment, an equation used to determine a survival predictor score is (Eqn. 1):

$$y = \sum_i c_i \cdot \log_2(x_i)$$

wherein y is the survival predictor score, $c_i$ is the coefficient value for gene i, and $x_i$ is the signal value for gene i. In another embodiment, an equation used to determine a survival predictor score is (Eqn. 2):

$$y = \sum_i c_i \cdot (x_i)$$

with y, $c_i$, $x_i$, and i as defined above for Eqn. 1. It is noted that either normalized counts or the raw counts may be used in the model In an embodiment, the coefficients used to generate a survival predictor score may be refined, and survival predictor score cut-points used to subdivide patients may be refined. For example, using methods as described herein with the same genes as those in Table 1, the coefficients for each gene may be determined to be different than as listed in Table 1 based on, e.g., the use of different types of biopsy (e.g., fresh) or use of different microarrays that provide different signal values. In an embodiment, the above methods may be incorporated into other methods, for example a Bayesian method as described in International Patent Application Publication No. WO 2015/069790, which is incorporated herein by reference. In another embodiment, the other relevant clinical variables may be used in conjunction with the methods described herein. These variables may include, for example, components of the MIPI score (which include age, serum lactate dehydrogenase (LDH) levels, white blood cell count, and ECOG performance status). The other clinical variables may improve the survival predictor score by being included in a weighted model that includes each of the components as well as the gene expression proliferation as described herein.

The present invention also provides a method of predicting the survival outcome of a human subject having MCL comprising determining the survival predictor score of the subject as described herein; and classifying the subject as belonging to one of the following groups based on the survival predictor score: good prognosis, intermediate prognosis, and poor prognosis. The present invention also provides a method of selecting a treatment for a human subject having MCL comprising classifying the subject as described herein; selecting a treatment for the subject based on the subject's classification; and providing the treatment to the subject. In an embodiment, the present invention may be used to select patients in clinical trials of novel agents and regimens.

In an embodiment, the present invention also provides a method of predicting the survival outcome of a human subject having MCL comprising determining the survival predictor score of the subject as described herein; and classifying the subject as belonging to one of the following groups based on the survival predictor score: good prognosis wherein y is calculated as less than −143, intermediate prognosis wherein y is calculated as between −143 and −28, and poor prognosis wherein y is calculated as greater than −28. Such an embodiment uses Eqn. 1 as defined above.

In an embodiment, the present invention also provides a method of predicting the survival outcome of a human subject having MCL comprising determining the survival predictor score of the subject as described herein; and classifying the subject as belonging to one of the following groups based on the survival predictor score: good prognosis wherein y is calculated as less than about −100000, intermediate prognosis wherein y is calculated as between about −100000 and about −32000, and poor prognosis wherein y is calculated as greater than about −32000. Such an embodiment uses Eqn. 2 as defined above.

In an embodiment, the present invention also provides a method of predicting the survival outcome of a human subject having mantle cell lymphoma (MCL) comprising obtaining or providing a formalin-fixed and paraffin-embedded (FFPE) biopsy sample from the subject; isolating RNA gene expression product from the biopsy sample; obtaining gene expression data from the RNA gene expression product, wherein the gene expression data comprises signal values that represent expression levels for each gene i of Table 1; and determining a survival predictor score from the gene expression data, wherein the survival predictor score is determined by the equation:

$$y = \sum_i c_i \cdot \log_2(x_i)$$

wherein y is the survival predictor score, $c_i$ is the coefficient value as listed in Table 1 for gene i, and $x_i$ is the signal value for gene i.

In an embodiment, the present invention entails the development of a set of nucleic acid probes that are able to measure the abundance of particular mRNA species using the NanoString Technologies® platform for the purpose of gene expression profiling MCL in order to subdivide them into clinically relevant groups with distinct prognoses. In this embodiment, RNA is extracted from, e.g., FFPE, biopsies using standard commercial kits and then hybridized and detected. The resultant digital RNA counts reflect the relative abundance of mRNAs transcribed from different genes. These expression levels are then combined in statistical algorithms to create a survival predictor score that is strongly associated with the overall survival of that patient.

In an embodiment, the present invention also provides a method of selecting a treatment for a human subject having MCL comprising classifying the subject as described herein; selecting a treatment for the subject based on the subject's classification; and providing the treatment to the subject. The method can comprise isolating a RNA gene expression product from a biopsy sample from an MCL subject, and obtaining gene expression data from the isolated RNA gene expression product. Descriptions of the RNA gene expression product, gene expression data, and gene expression signature set forth herein in connection with other embodiments of the invention also are applicable to those same aspects of the aforesaid inventive method for selecting a treatment for a subject who already has been diagnosed with MCL.

The treatment selected may comprise any suitable therapeutic regimen or pharmaceutical agent that shows efficacy in treating MCL. Treatments for MCL include, for example, chemotherapy (e.g., CHOP (cyclophosphamide, hydroxydaunorubicin, oncovin (vincristine), and prednisone), immune based therapy (e.g., rituximab), radioimmunotherapy, biologic agents (e.g., protoesome inhibitors, BTK inhibitors, IMiDs and mTor inhibitors) and consolidative autologous stem cell transplantation. Treatments also include R-CHOP (CHOP with rituximab) or bendamustine plus rituximab (Rummel et al., Lancet, 381(9873):1203-10 (2013), incorporated herein by reference).

In an embodiment of the invention, the survival predictor score assigns a patient into poor, intermediate and good survival groups with median survivals of 1.1, 2.6, and 8.6 years, respectively, following treatment with R-CHOP with or without autologous stem cell transplantation.

MCL is recognized to be a heterogeneous group of lymphomas displaying a range of clinical behavior with some patients having slowly progressive disease that does not require immediate treatment, while others have disease that rapidly progress despite highly aggressive treatment. In an embodiment, the treatment is delayed, for example, if the subject is classified as having a good prognosis. In another embodiment, the treatment is administered immediately, for example, if the subject is classified as having a poor prognosis.

In an embodiment, the present invention provides a composition consisting of probes to the target sequences described herein. In another embodiment, the present invention also provides a kit comprising the probes, for example, a kit comprising components suitable for performing NanoString Technologies® nCounter® digital gene expression assays.

The following include certain aspects of the invention.

Aspect 1. A method of determining a survival predictor score of a human subject having mantle cell lymphoma (MCL), which method comprises:

(a) obtaining or providing a formalin-fixed and paraffin-embedded (FFPE) biopsy sample from the subject;

(b) isolating RNA gene expression product from the biopsy sample;

(c) obtaining gene expression data from the RNA gene expression product, wherein the gene expression data comprises signal values that represent expression levels for each gene of Table 1; and (d) determining a survival predictor score from the gene expression data, wherein the survival predictor score is determined by calculating a multiplication product for each gene of Table 1, wherein the multiplication product is the mathematical product of the log transformation of the signal value of a gene with a coefficient value for that gene, the coefficient value for the gene listed in Table 1, and summing the multiplication products.

Aspect 2. The method of aspect 1, wherein the survival predictor score is determined by the equation:

$$y = \sum_i c_i \cdot \log_2(x_i)$$

wherein y is the survival predictor score, $c_i$ is the coefficient value for gene i, and $x_i$ is the signal value for gene i.

Aspect 3. The method of aspect 1 or 2, wherein the RNA gene expression data is obtained using a NanoString Technologies® nCounter® assay.

Aspect 4. A method of predicting the survival outcome of a human subject having mantle cell lymphoma (MCL) comprising:
(a) determining the survival predictor score of the subject according to any one of aspects 1-3; and
(b) classifying the subject as belonging to one of the following groups based on the survival predictor score: (i) good prognosis, (ii) intermediate prognosis, and (iii) poor prognosis.

Aspect 5. A method of predicting the survival outcome of a human subject having mantle cell lymphoma (MCL) comprising:
(a) determining the survival predictor score of the subject according to aspect 4; and
(b) classifying the subject as belonging to one of the following groups based on the survival predictor score: (i) good prognosis wherein y is calculated as less than −143, (ii) intermediate prognosis wherein y is calculated as between −143 and −28, and (iii) poor prognosis wherein y is calculated as greater than −28.

Aspect 6. A method of selecting a treatment for a human subject having mantle cell lymphoma (MCL) comprising:
(a) classifying the subject according to aspect 4 or 5;
(b) selecting a treatment for the subject based on the subject's classification; and
(c) optionally providing the treatment to the subject.

Aspect 7. The method of aspect 6, wherein the subject is classified as having a good prognosis and the optional treatment is delayed.

Aspect 8. The method of aspect 6, wherein the subject is classified as having a poor prognosis and the optional treatment is administered immediately.

Aspect 9. The method of any one of aspects 6-8, wherein the treatment includes administration of R-CHOP (rituximab, cyclophosphamide, hydroxydaunorubicin, vincristine, and prednisone).

Aspect 10. A method of determining a survival predictor score of a human subject having mantle cell lymphoma (MCL), which method comprises:
(a) obtaining or providing a formalin-fixed and paraffin-embedded (FFPE) biopsy sample from the subject;
(b) isolating RNA gene expression product from the biopsy sample;
(c) obtaining gene expression data from the RNA gene expression product, wherein the gene expression data comprises signal values that represent expression levels for each gene of Table 1; and
(d) determining a survival predictor score from the gene expression data, wherein the survival predictor score is determined by
calculating a multiplication product for each gene of Table 1, wherein the multiplication product is the mathematical product of the signal value of a gene with a coefficient value for that gene, the coefficient value for the gene listed in Table 1, and
summing the multiplication products.

Aspect 11. The method of aspect 10, wherein the survival predictor score is determined by the equation:

$$y = \sum_i c_i \cdot (x_i)$$

wherein y is the survival predictor score, $c_i$ is the coefficient value for gene i, and $x_i$ is the signal value for gene i.

Aspect 12. The method of aspect 10 or 11, wherein the RNA gene expression data is obtained using a NanoString Technologies® nCounter® assay.

Aspect 13. A method of predicting the survival outcome of a human subject having mantle cell lymphoma (MCL) comprising:
(a) determining the survival predictor score of the subject according to any one of aspects 10-12; and
(b) classifying the subject as belonging to one of the following groups based on the survival predictor score: (i) good prognosis, (ii) intermediate prognosis, and (iii) poor prognosis.

Aspect 14. A method of predicting the survival outcome of a human subject having mantle cell lymphoma (MCL) comprising:
(a) determining the survival predictor score of the subject according to aspect 13; and
(b) classifying the subject as belonging to one of the following groups based on the survival predictor score: (i) good prognosis wherein y is calculated as less than about −100000, (ii) intermediate prognosis wherein y is calculated as between about −100000 and about −32000, and (iii) poor prognosis wherein y is calculated as greater than about −32000.

Aspect 15. A method of selecting a treatment for a human subject having mantle cell lymphoma (MCL) comprising:
(a) classifying the subject according to aspect 13 or 14;
(b) selecting a treatment for the subject based on the subject's classification; and
(c) optionally providing the treatment to the subject.

Aspect 16. The method of aspect 15, wherein the subject is classified as having a good prognosis and the optional treatment is delayed.

Aspect 17. The method of aspect 15, wherein the subject is classified as having a poor prognosis and the optional treatment is administered immediately.

Aspect 18. The method of any one of aspects 15-17, wherein the treatment includes administration of R-CHOP (rituximab, cyclophosphamide, hydroxydaunorubicin, vincristine, and prednisone).

Aspect 19. A method of predicting the survival outcome of a human subject having mantle cell lymphoma (MCL) comprising:
(a) obtaining or providing a formalin-fixed and paraffin-embedded (FFPE) biopsy sample from the subject;
(b) isolating RNA gene expression product from the biopsy sample;
(c) obtaining gene expression data from the RNA gene expression product, wherein the gene expression data comprises signal values that represent expression levels for each gene i of Table 1; and
(d) determining a survival predictor score from the gene expression data, wherein the survival predictor score is determined by the equation:

$$y = \sum_i c_i \cdot \log_2(x_i)$$

wherein y is the survival predictor score, $c_i$ is the coefficient value as listed in Table 1 for gene i, and $x_i$ is the signal value for gene i.

It shall be noted that the preceding are merely examples of embodiments. Other exemplary embodiments are apparent from the entirety of the description herein. It will also be understood by one of ordinary skill in the art that each of these embodiments may be used in various combinations with the other embodiments provided herein.

The following examples further illustrate the invention but, of course, should not be construed as in any way limiting its scope.

EXAMPLE

This example demonstrates the subdivision of patients with MCL into clinically relevant groups with distinct prognoses, in accordance with embodiments of the invention.

Methods

Study Design and Patient Population

The overall design of the process for developing and characterizing the assay for the proliferation signature in MCL is shown in FIG. 1. The study involved retrospective gene expression profiling of samples from patients with MCL, confirmed by expert pathology consensus review. Biopsies contributing to the training of the new assay included 80 biopsies described in Rosenwald et al. (Cancer Cell, 3:185-197 (2003), incorporated by reference herein) along with an additional 51 biopsies gathered from the clinical sites of the LLMPP (43 frozen and 8 FFPE). These biopsies, with tumor content of at least 60%, were obtained from patients who subsequently received a broad range of treatment regimens.

Thus, there were 3 different data sets that were considered as part of the training: (a) 80 Frozen Affymetrix® samples from the Rosenwald paper used to generate coefficients and to generate cut points, (b) 43 New Frozen samples used as an initial pre-validation check and as part of the set to generate cut-points, and (c) 47 FFPE samples used to adjust the model to account for the difference between Affymetrix® and Nanostring®. Set (a) and (b) were totally independent of each other, but 39 samples in set (c) were replicated in either set (a) or in set (b), and so set (c) only contributed 8 new samples. Thus, in total there were the 80 Rosenwald samples and 51 (43+8) non-Rosenwald samples.

Figure 2:
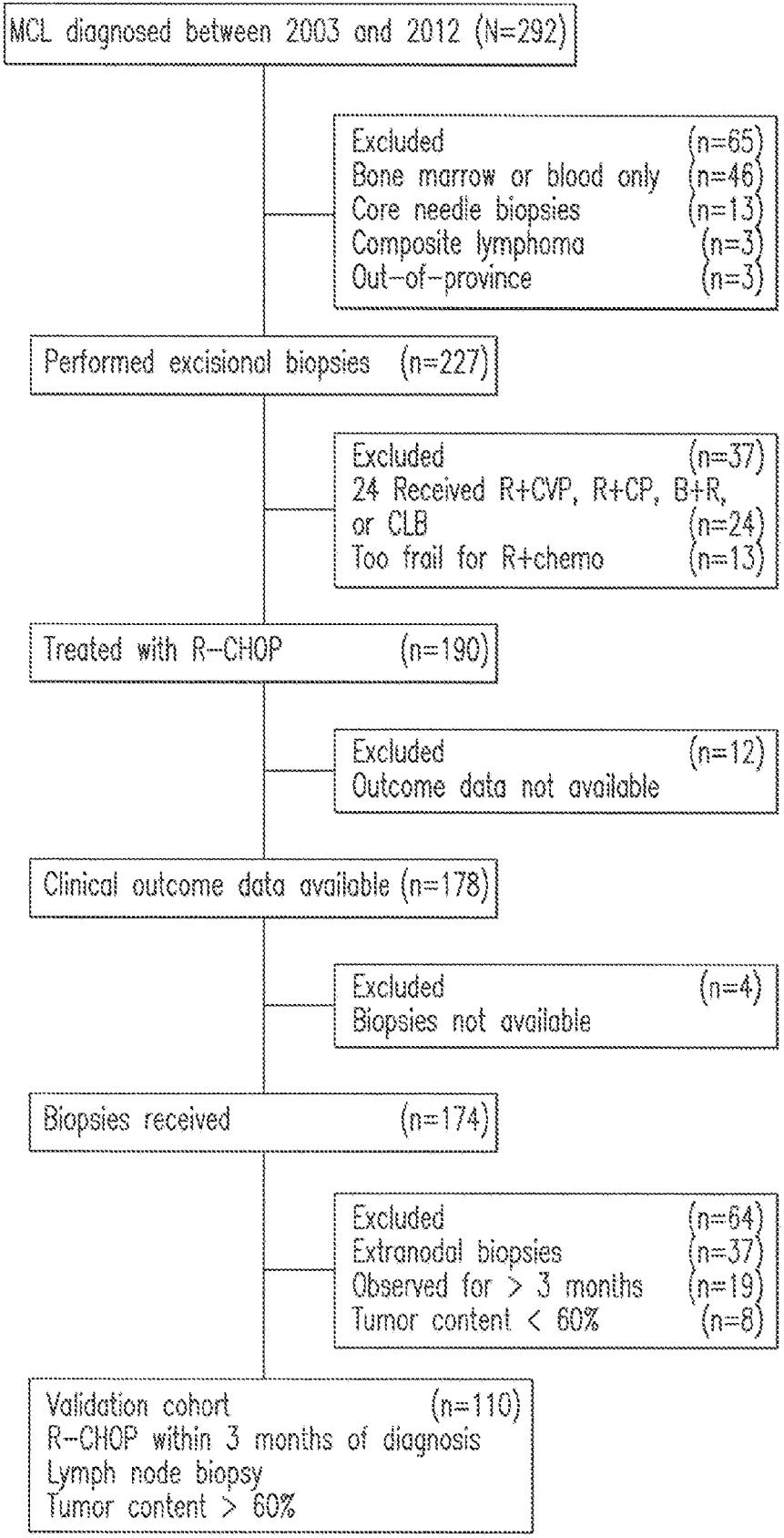
FIG. 2 is a flow chart showing patient flow for the validation cohort (B+R, bendamustine plus rituximab; CLB, chlorambucil; MCL: mantle cell lymphoma; R, rituximab; R-CHOP, rituximab plus cyclophosphamide, doxorunbicin, vincristine, and prednisone; R+CP, rituximab plus cyclophosphamide and prednisone; R+CVP, rituximab plus cyclophosphamide, vincristine, and prednisone), in accordance with embodiments of the invention.

The assay was validated using 110 pre-treatment biopsies from an independent cohort of patients treated at the British Columbia Cancer Agency (BCCA) (Table 2, FIG. 2).

TABLE 2

| Variable | Total Cohort | MCL35 categories | | | P value§ |
| --- | --- | --- | --- | --- | --- |
| | | Low-Risk Group | Standard-Risk Group | High-Risk Group | |
| Patients | | | | | |
| Assessable patients | 108 | 49 (45%) | 31 (29%) | 28 (26%) | |
| Male | 86 (80%) | 39 (80%) | 26 (84%) | 21 (75%) | 0.75 |
| Female | 22 (20%) | 10 (20%) | 5 (16%) | 7 (25%) | |
| Age - median (range) years | 62 (41-84) | 60 (41-84) | 64 (45-74) | 68 (41-81) | 0.18 |
| >65 years | 39 (36%) | 12 (24%) | 12 (39%) | 15 (54%) | 0.04 |
| Clinical features | | | | | |
| ECOG performance status | | | | | 0.20 |
| 0-1 | 75 (76%) | 39 (83%) | 20 (74%) | 16 (64%) | |
| 2-4 | 24 (24%) | 8 (17%) | 7 (26%) | 9 (36%) | |
| Missing | 9 | 2 | 4 | 3 | |
| White cell count - median (range) | 6.9 (1.7-79.2) | 6.4 (2.7-12.7) | 8.7 (1.7-41.4) | 7.9 (2.3-79.2) | 0.02 |
| LDH | | | | | 0.007 |
| Normal | 54 (57%) | 30 (68%) | 17 (63%) | 7 (29%) | |
| >Upper level of normal | 41 (43%) | 14 (32%) | 10 (27%) | 17 (71%) | |
| Missing | 13 | 5 | 4 | 4 | |
| MIPI | | | | | 0.001 |
| Low (<5.7) | 38 (41%) | 27 (61%) | 8 (31%) | 3 (13%) | |
| Intermediate (5.7-6.2) | 20 (22%) | 7 (16%) | 8 (31%) | 5 (22%) | |
| High (≥6.2) | 35 (38%) | 10 (23%) | 10 (38%) | 15 (65%) | |
| Missing | 15 | 5 | 5 | 5 | |
| Pathology | | | | | |
| Morphology | | | | | <0.001 |
| Classic | 95 (88%) | 49 (100%) | 29 (94%) | 17 (61%) | |
| Pleomorphic | 3 (3%) | 0 | 0 | 3 (11%) | |
| Blastoid | 10 (9%) | 0 | 2 (6%) | 8 (29%) | |
| Ki-67 proliferation index | | | | | <0.001 |
| <30% | 53 (49%) | 45 (92%) | 6 (19%) | 2 (7%) | |
| ≥30% | 55 (51%) | 4 (8%) | 25 (81%) | 26 (93%) | |
| TP53 immunohistochemistry | | | | | <0.001 |
| Negative | 93 (87%) | 49 (100%) | 26 (87%) | 18 (64%) | |
| Positive | 14 (13%) | 0 | 4 (13%) | 10 (36%) | |
| Fail | 1 | 0 | 1 | 0 | |
| CCND1 3'UTR | | | | | <0.001 |
| Wildtype | 89 (82%) | 49 (100%) | 27 (87%) | 13 (46%) | |
| Truncated | 19 (18%) | 0 | 4 (13%) | 15 (54%) | |
| Treatment | | | | | |
| R-CHOP | 108 (100%) | 49 (100%) | 31 (100%) | 28 (100%) | |
| Consolidative autologous stem cell transplant | | | | | 0.96^ |
| Per protocol intention-to-treat | 58 (84%*) | 31 (84%*) | 17 (89%*) | 10 (77%*) | |

TABLE 2-continued

| | | MCL35 categories | | | |
|---|---|---|---|---|---|
| Variable | Total Cohort | Low-Risk Group | Standard-Risk Group | High-Risk Group | P value[§] |
| Received transplant per protocol | 42 (72%[#]) | 24 (77%[#]) | 12 (71%[#]) | 6 (60%[#]) | |
| Received transplant outside protocol | 1 | 0 | 1 | 0 | |
| Median follow up - months | 78 | 98 | 68 | 75 | |

Table abbreviations:
ECOG: Eastern Cooperative Oncology Group; LDH: lactate dehydrogenase; MIPI; mantle cell lymphoma international prognostic index; UTR: untranslated region; R-CHOP: rituximab with cyclophosphamide, doxorubicin, vincristine and prednisone.
[§]P values are for comparisons across the 3 risk groups determined by the MCL35 score;
*percent of patients 65 years or younger;
[#]percentage of patients where there was an intention to consolidate with an autologous stem cell transplant;
^comparison across groups of number of patients that received an autologous stem cell transplant to the number where there was an intention to consolidate with an autologous stem cell transplant.

Patients diagnosed with MCL at the BCCA between 2003 and 2012 were identified using the BCCA Lymphoid Cancer Database. Inclusion in the validation cohort required a diagnostic excisional FFPE biopsy of a lymph node with tumor content of ≥60%, and treatment with R-CHOP (rituximab, cyclophosphamide, doxorubicin, vincristine, and prednisone) within 3 months of the diagnostic biopsy. Biopsies with a predominantly mantle zone involvement by lymphoma cells were excluded. All biopsies were centrally reviewed to confirm a diagnosis of conventional MCL and were positive for cyclin D1 by immunohistochemistry (Swerdlow et al., World Health Organization Classification of Tumours of Haematopoietic and Lymphoid Tissues. (ed 4th). Lyon, IARC Press (2008), incorporated herein by reference). BCCA policy during this era was to treat MCL using the R-CHOP regimen with a planned consolidative autologous stem cell transplantation (ASCT) for appropriate patients ≤65 years of age. A policy to provide maintenance rituximab (375 mg/m$^2$ intravenously every 3 months for 2 years) to patients who did not receive a consolidative ASCT was introduced in 2011. The study was approved by the University of British Columbia-BCCA Research Ethics Board.

Gene Expression Profiling

Gene expression profiling of RNA extracted from FF biopsies used in the training of the assay was performed on Affymetrix® U133 plus 2.0 microarrays (Thermo Fisher Scientific, Waltham, Mass., USA). Data are available at ncbi.nlm.nih.gov/geo/query/acc.cgi.

Nucleic acids were extracted from 10 µm sections of FFPE biopsies using the QIAGEN® AllPrep DNA/RNA/DNA FFPE Kits (QIAGEN®, Hilden, Germany) after deparaffinization according to the manufacturer's instructions. Gene expression was quantitated in 200 ng of RNA on the NanoString® platform (NanoString Technologies®, Seattle, Wash., USA), using the "high sensitivity" setting on the nCounter™ PrepStation and 490 fields of view on the nCounter™ Analyzer (Generation 2) or 1,155 fields of view when a Generation 1 analyzer was used. Normalization for RNA loading was performed using the geometric mean of 18 housekeeping genes. Samples in which this geometric mean was below value of 140 were deemed to have failed.

Probes to exon 3 and the 3'untranslated region (UTR) of CCND1 were used to assess the status of the CCND1 3'UTR (see below).

Immunohistochemistry and the MIPI

Ki-67 IHC (MIB-1) was performed on whole tissue sections on a Ventana Benchmark platform (Ventana Medical Systems, Tucson, Ariz., USA) and scored by counting 200 cells per biopsy according to the recommendations of Klapper et al. (J. Hematop., 2:103-11, (2009)), incorporated herein by reference. The Ki-67 PI was defined as the proportion of positive tumor cells. TP53 IHC (clone DO-7) was performed on tissue microarrays comprising duplicate 0.6 mm cores from FFPE blocks of the biopsies, with positivity defined as strong uniform nuclear staining of tumor cells; all positive biopsies had staining in greater than 30% of tumor cells. The MIPI was calculated per Hoster et al. (Blood, 111:558-565 (2008)), incorporated herein by reference.

Statistical Analysis

The statistical analysis plan was specified before the evaluation of gene expression from the validation cohort. Fisher's exact and Kruskal-Wallis exact tests were used to examine the significance of differences in patient and pathology characteristics between groups. The median follow up was estimated using the reverse censoring method (Schemper et al., Controlled Clinical Trials, 17:343-346, 1996, incorporated herein by reference). The primary endpoint of the study was overall survival (OS), which was calculated from the date of diagnosis to date of death from any cause. OS was estimated using the Kaplan-Meier method. A planned subgroup analysis was performed, which was limited to patients for whom there was a per-policy intention-to-treat with a consolidative ASCT.

Univariable analyses using Cox models were implemented to examine the relationship between continuous variables and OS. Log-rank tests were used to test the relationship between discrete variables and OS. Cox proportional hazards regression model score tests were used to test the association of variables with OS in combination with other variables. It was pre-specified that one-sided P values <0.05 would be considered significant.

More detail regarding the methods is provided below.

Proliferation Signature Modeling

Figure 3:
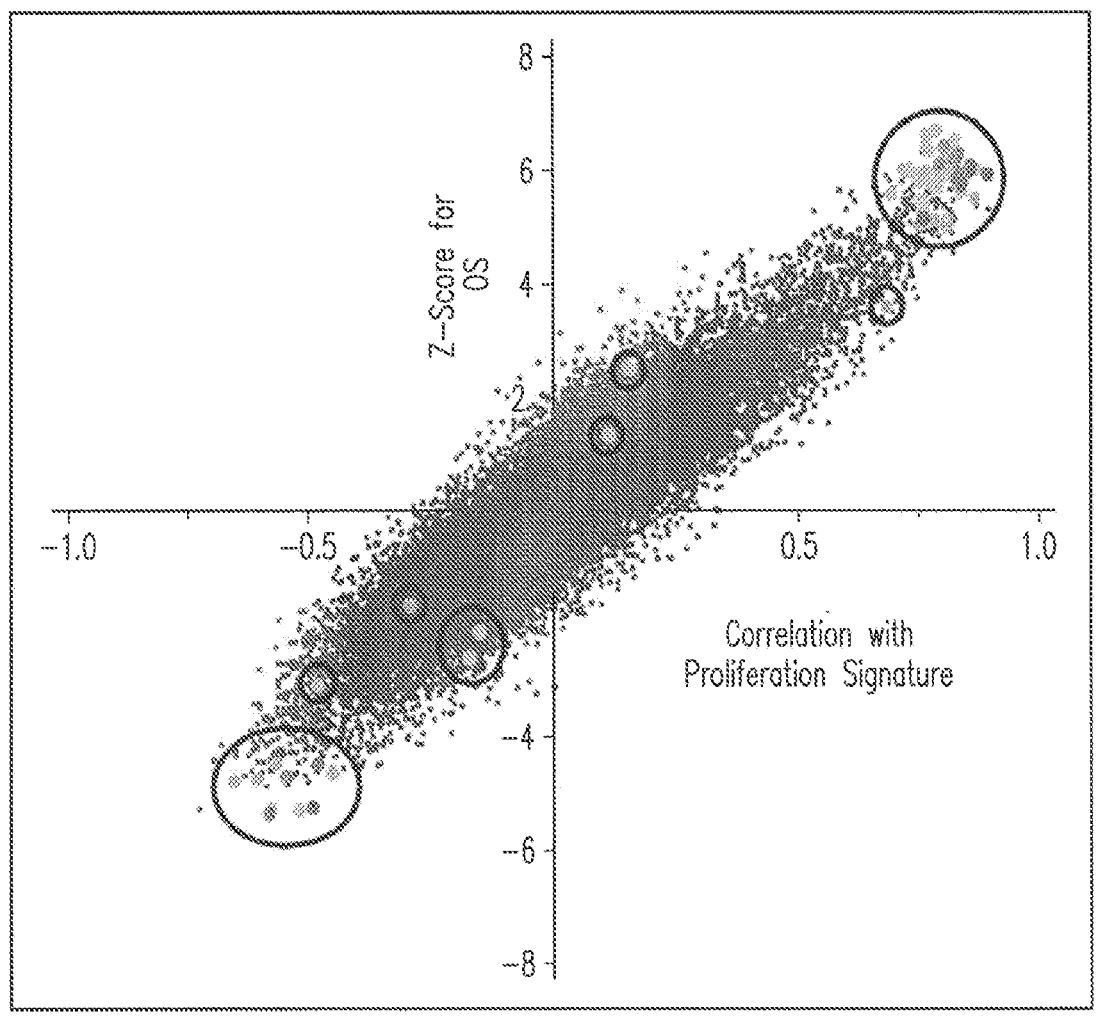
FIG. 3 is a dot plot showing gene expression data in the training cohort. The correlation of the expression of individual genes to the proliferation signature calculated in Rosenwald et al., Cancer Cell, 3:185-197 (2003), plotted against the Wald test Z-score for overall survival (OS) for that gene. The data are from gene expression profiling of 80 fresh frozen biopsies from Rosenwald et al., Cancer Cell, 3:185-197 (2003) using Affymetrix® U133 plus 2.0 microarrays. The large dots within the circles represent genes that were included in the NanoString® gene set, which was used to select genes to replicate the proliferation signature. A subset of these were selected for the MCL35 assay.

An initial set of 80 fresh frozen MCL biopsies, that had been previously studied on a custom Lymphochip Microarrays element (Rosenwald et al., Cancer Cell, 3:185-197 (2003), incorporated by reference herein), were analyzed with a U133 plus 2.0 platform, normalized with MAS5.0 software, and $log_2$ transformed. For each gene the association between that gene expression and survival was estimated using a Wald test statistic, the Pearson correlation was used between that gene's expression, and a proliferation signature was calculated (FIG. 3).

To translate the proliferation signature into a prognostic tool that could be applied to FFPE data, 47 FFPE biopsies were collected, including 39 biopsies with matched Affymetrix® gene expression data on RNA from fresh frozen biopsies. A NanoString® codeset was designed that included an initial set of 69 discriminative genes (11 associated with good prognosis and anti-correlated with the proliferation signature, 58 that were associated with poor survival and positively correlated with the proliferation signature) as well as 30 housekeeper genes that were well expressed and had low variance across MCL samples that could be used for normalization. RNA from the 47 FFPE samples were then analyzed on the NanoString® platform, and the genes were evaluated for their expression level, variance across the biopsies, and agreement with matched Affymetrix® expression.

Based on these observations a final refined codeset was created that included 17 predictive genes (13 correlated with proliferation, 4 anti-correlated with proliferation) and 18 housekeeping genes. The 47 FFPE samples were then re-analyzed with this refined codeset on which the final model was based.

As a template for the eventual FFPE model, predictive genes were reviewed on a set of 80 fresh frozen MCL biopsies described in Rosenwald et al. (Cancer Cell, 3:185-197 (2003)), analyzed with Affymetrix® U133 2.0 arrays. Signal values were generated with MAS5.0 and log 2 transformed. An individual model scores was generated for genes according to the following formula (Eqn. 3):

$$Score_j = \sum_i x_{ij} \rho_i Z_i$$

where $x_{ij}$ is the $\log_2$ transformed Affymetrix® signal value for gene i on sample j, $\rho_i$ is the Pearson correlation between gene i and the Rosenwald proliferation signature, and $Z_i$ is the Wald Z-score for the association between expression of gene i and overall survival. A positive predictive score was generated, for which the sum was over the 13 genes that were identified as positively correlated with proliferation, and a negative predictive score was generated where the sum was over the 4 genes that were negatively associated with proliferation. This model was applied to Affymetrix® microarray data from an independent set of 43 MCL biopsies that had not been previously analyzed. After ascertaining that both individual signatures showed a strong effect on this independent data set (P<0.001), all 123 patients were combined into a single data set, and a Cox proportional hazards model was fit to combine the two scores into a single Frozen Affymetrix® Proliferation Score (FAPS). Next all possible pairs thresholds that divided the samples into the three groups according to their FAPS was considered. Those thresholds were selected for which the three defined groups had most statistically significant association with survival as measured by the log rank test. Those with scores less than 243 are considered to be in a good prognosis group (low risk) those with scores between 243 and 358 are considered to be in an intermediate prognosis group (intermediate risk); and those with scores greater than 358 are considered to be in a poor prognosis group (high risk). The above served as a template from which the FFPE NanoString®-based model was derived.

The NanoString® codeset was then used to analyze these genes. The NanoString® digital gene specific counts were normalized by dividing the counts of each sample by the geometric mean of the counts of the housekeeper genes, and then log 2 transformed. (The values for the normalization genes are set to 0.75 so that the sum over all coefficients (normalization, proliferation and anti-proliferation) sums to zero. In this way an increase in genetic material that would cause uniform signal increase of all genes by a constant amount will not affect the model score.) Based on this data, two signatures were generated based on the 13 positively correlated and 4 negatively correlated signatures, according to the following formula (Eqn. 4):

$$Score_j = \sum_i h_{ij} \cdot \rho_i Z_i \lambda_j$$

where $\rho_i$ and $Z_i$ are as before, $h_{ij}$ represents the $\log_2$ transformed normalized NanoString® count for gene i on sample j and $\lambda_j$ represents the Pearson correlation between the matched NanoString® counts and Affymetrix® signal values. A regression was fit between the two NanoString® based predictor scores and the FAPS for the matched samples, giving a final "MCL35" signature that mimicked the FAPS. The values for the proliferation and anti-proliferation genes are provided in Table 3.

TABLE 3

| Gene ID | rho | Z | lambda | Regression Adjust | Final coefficient |
|---|---|---|---|---|---|
| SPG3A/ATL1 | −0.496 | −5.244 | 0.654 | −11.535 | −19.637 |
| FMNL3 | −0.46 | −4.643 | 0.871 | −11.535 | −21.461 |
| GLIPR1 | −0.586 | −5.35 | 0.827 | −11.535 | −29.911 |
| ZDHHC21 | −0.549 | −4.695 | 0.789 | −11.535 | −23.474 |
| CCNB2 | 0.837 | 5.718 | 0.799 | 1.57 | 6.008 |
| CDC20 | 0.855 | 5.972 | 0.792 | 1.57 | 6.349 |
| CDKN3 | 0.794 | 6.084 | 0.844 | 1.57 | 6.404 |
| E2F2 | 0.83 | 5.803 | 0.796 | 1.57 | 6.018 |
| ESPL1 | 0.892 | 5.907 | 0.786 | 1.57 | 6.5 |
| FAM83D | 0.838 | 5.787 | 0.777 | 1.57 | 5.917 |
| FOXM1 | 0.828 | 6.195 | 0.813 | 1.57 | 6.549 |
| H2AFX | 0.802 | 6.409 | 0.753 | 1.57 | 6.077 |
| KIF2C | 0.843 | 5.98 | 0.782 | 1.57 | 6.19 |
| MKI67 | 0.832 | 6.295 | 0.809 | 1.57 | 6.654 |
| NCAPG | 0.837 | 5.933 | 0.826 | 1.57 | 6.437 |
| TOP2A | 0.824 | 6.155 | 0.811 | 1.57 | 6.462 |
| ZWINT | 0.76 | 5.133 | 0.883 | 1.57 | 5.41 |

The above can be rewritten as Eqn. 1:

$$y = \sum_i c_i \cdot \log_2(x_i)$$

(where y is the survival predictor score, $c_i$ is the coefficient value for gene i, and $x_i$ is the signal value for gene i), with $Score_j$ as y, $c_i$ equal to $\rho_i Z_i \lambda_i$ multiplied by the factor that takes into account the regression fit, and $h_{ij}$ as $\log_2(x_i)$.

The model was scaled so that the variance of the FFPE model matched that of the frozen model. All of the weights and scaling were combined into what is presented as the coefficients. The weights of the 18 normalization genes were set to a constant value chosen such that the total sum over all coefficients was equal to 0, which effectively normalizes the data so that a uniform increase of all expression values by a fixed proportion will have no effect on the score. The resulting FFPE score was found to be shifted by 386 and so equivalently shifted cut-points were used to the following subgroups according to the FFPE signature: a low risk group of those with model score less than −143; an intermediate risk for model score between −143 and −28; and a high risk for model score greater than −28.

Thereby the thresholds optimized for the FAPS could be directly used to divide samples by their MCL35 signature into low-, standard- and high-risk groups. The model, including the gene coefficients, adjustments and thresholds, was then "locked" and validated in an independent cohort of patients. Tables 4 and 5 contain outcome data and digital expression data for the MCL35 assay, for the independent validation cohort, respectively.

TABLE 4

Outcome data and MCL35, MIPI and Ki67 IHC categories for the validation cohort

| IDENTIFIER | ASCT ITT | MCL35 | MIPI | KI67 IHC (%) | CODE_OS | Overall survival (y) |
|---|---|---|---|---|---|---|
| MCL001 | YES | LOW | LOW | 10-29 | 0 | 4.50 |
| MCL002 | NO | FAIL | INTERMEDIATE | 10-29 | 1 | 1.56 |
| MCL006 | NO | STANDARD | NOT AVAILABLE | >=30 | 1 | 0.82 |
| MCL007 | YES | LOW | LOW | 10-29 | 1 | 5.96 |
| MCL008 | NO | LOW | NOT AVAILABLE | <10 | 0 | 9.22 |
| MCL009 | NO | STANDARD | HIGH | >=30 | 1 | 2.17 |
| MCL010 | YES | LOW | LOW | 10-29 | 0 | 10.90 |
| MCL011 | NO | LOW | LOW | <10 | 0 | 11.00 |
| MCL012 | NO | STANDARD | LOW | >=30 | 1 | 1.08 |
| MCL015 | NO | STANDARD | INTERMEDIATE | >=30 | 0 | 2.89 |
| MCL016 | YES | LOW | LOW | 10-29 | 0 | 1.54 |
| MCL017 | YES | LOW | LOW | 10-29 | 0 | 2.97 |
| MCL018 | NO | HIGH | HIGH | >=30 | 1 | 0.47 |
| MCL019 | YES | HIGH | HIGH | >=30 | 1 | 1.69 |
| MCL020 | YES | STANDARD | LOW | >=30 | 0 | 4.60 |
| MCL021 | YES | STANDARD | LOW | 10-29 | 0 | 5.70 |
| MCL022 | YES | LOW | LOW | 10-29 | 0 | 6.54 |
| MCL023 | YES | LOW | LOW | 10-29 | 1 | 2.43 |
| MCL024 | NO | LOW | HIGH | <10 | 1 | 2.18 |
| MCL025 | YES | STANDARD | LOW | 10-29 | 0 | 7.11 |
| MCL026 | NO | STANDARD | NOT AVAILABLE | >=30 | 1 | 1.89 |
| MCL027 | YES | LOW | INTERMEDIATE | 10-29 | 1 | 5.04 |
| MCL029 | YES | LOW | LOW | 10-29 | 0 | 3.45 |
| MCL031 | YES | HIGH | LOW | >=30 | 1 | 0.76 |
| MCL033 | NO | LOW | NOT AVAILABLE | 10-29 | 0 | 10.20 |
| MCL035 | NO | STANDARD | HIGH | 10-29 | 1 | 2.57 |
| MCL036 | YES | LOW | LOW | 10-29 | 0 | 6.52 |
| MCL037 | YES | STANDARD | INTERMEDIATE | >=30 | 1 | 3.24 |
| MCL038 | NO | HIGH | HIGH | >=30 | 1 | 0.45 |
| MCL040 | YES | HIGH | HIGH | >=30 | 1 | 0.54 |
| MCL041 | YES | LOW | LOW | <10 | 1 | 1.20 |
| MCL042 | YES | HIGH | HIGH | >=30 | 1 | 1.40 |
| MCL043 | NO | HIGH | HIGH | >=30 | 0 | 3.23 |
| MCL044 | NO | HIGH | HIGH | >=30 | 1 | 0.86 |
| MCL045 | YES | LOW | LOW | 10-29 | 0 | 3.56 |
| MCL047 | YES | LOW | LOW | >=30 | 0 | 4.46 |
| MCL048 | NO | LOW | HIGH | <10 | 1 | 0.91 |
| MCL050 | NO | HIGH | NOT AVAILABLE | >=30 | 1 | 2.78 |
| MCL052 | NO | HIGH | HIGH | >=30 | 1 | 0.37 |
| MCL053 | YES | STANDARD | LOW | >=30 | 1 | 2.09 |
| MCL054 | NO | STANDARD | INTERMEDIATE | >=30 | 1 | 5.94 |
| MCL055 | YES | LOW | HIGH | 10-29 | 0 | 8.18 |
| MCL057 | NO | HIGH | HIGH | >=30 | 1 | 0.30 |
| MCL059 | YES | LOW | LOW | >=30 | 0 | 9.84 |
| MCL060 | NO | LOW | HIGH | <10 | 1 | 5.42 |
| MCL061 | NO | HIGH | INTERMEDIATE | >=30 | 1 | 2.01 |
| MCL062 | YES | STANDARD | LOW | >=30 | 0 | 5.10 |
| MCL063 | YES | LOW | NOT AVAILABLE | 10-29 | 0 | 8.78 |
| MCL064 | YES | LOW | LOW | 10-29 | 1 | 8.58 |
| MCL065 | NO | LOW | HIGH | 10-29 | 0 | 2.89 |
| MCL067 | NO | HIGH | HIGH | >=30 | 0 | 3.10 |
| MCL068 | YES | LOW | LOW | <10 | 0 | 4.66 |
| MCL069 | YES | STANDARD | HIGH | >=30 | 1 | 2.44 |
| MCL071 | NO | LOW | HIGH | 10-29 | 0 | 5.43 |
| MCL072 | NO | HIGH | NOT AVAILABLE | >=30 | 1 | 2.60 |
| MCL074 | NO | LOW | LOW | <10 | 0 | 11.40 |
| MCL075 | NO | LOW | HIGH | <10 | 1 | 7.24 |
| MCL076 | NO | STANDARD | NOT AVAILABLE | >=30 | 1 | 3.93 |
| MCL078 | NO | LOW | INTERMEDIATE | <10 | 0 | 3.09 |
| MCL079 | YES | STANDARD | HIGH | >=30 | 1 | 2.96 |
| MCL080 | YES | STANDARD | HIGH | >=30 | 0 | 3.03 |
| MCL082 | YES | LOW | LOW | 10-29 | 0 | 3.39 |
| MCL083 | YES | LOW | LOW | 10-29 | 0 | 3.61 |
| MCL085 | YES | STANDARD | INTERMEDIATE | >=30 | 0 | 4.22 |
| MCL088 | YES | LOW | LOW | 10-29 | 0 | 5.18 |
| MCL089 | NO | HIGH | NOT AVAILABLE | >=30 | 1 | 2.26 |
| MCL091 | NO | HIGH | HIGH | >=30 | 1 | 0.92 |
| MCL092 | YES | LOW | HIGH | 10-29 | 1 | 3.61 |
| MCL093 | NO | HIGH | INTERMEDIATE | >=30 | 1 | 0.84 |

TABLE 4-continued

Outcome data and MCL35, MIPI and Ki67 IHC categories for the validation cohort

| IDENTIFIER | ASCT ITT | MCL35 | MIPI | KI67 IHC (%) | CODE_OS | Overall survival (y) |
|---|---|---|---|---|---|---|
| MCL094 | NO | HIGH | NOT AVAILABLE | >=30 | 1 | 0.79 |
| MCL095 | YES | LOW | LOW | 10-29 | 1 | 5.73 |
| MCL096 | YES | STANDARD | INTERMEDIATE | <10 | 1 | 2.00 |
| MCL097 | NO | HIGH | HIGH | >=30 | 1 | 0.35 |
| MCL098 | YES | FAIL | LOW | <10 | 1 | 5.85 |
| MCL099 | NO | LOW | INTERMEDIATE | 10-29 | 1 | 5.17 |
| MCL100 | NO | LOW | HIGH | 10-29 | 1 | 4.87 |
| MCL102 | YES | LOW | LOW | <10 | 0 | 8.60 |
| MCL103 | NO | STANDARD | NOT AVAILABLE | 10-29 | 1 | 1.75 |
| MCL104 | NO | LOW | LOW | 10-29 | 1 | 7.01 |
| MCL105 | YES | STANDARD | INTERMEDIATE | 10-29 | 1 | 1.66 |
| MCL106 | YES | LOW | LOW | 10-29 | 0 | 12.65 |
| MCL108 | NO | STANDARD | HIGH | >=30 | 1 | 1.66 |
| MCL109 | NO | STANDARD | NOT AVAILABLE | >=30 | 1 | 0.69 |
| MCL110 | YES | HIGH | LOW | >=30 | 1 | 0.80 |
| MCL113 | YES | HIGH | INTERMEDIATE | >=30 | 1 | 1.23 |
| MCL114 | YES | LOW | INTERMEDIATE | 10-29 | 1 | 6.00 |
| MCL115 | YES | HIGH | HIGH | >=30 | 1 | 1.02 |
| MCL116 | NO | LOW | LOW | <10 | 0 | 9.24 |
| MCL117 | NO | STANDARD | HIGH | >=30 | 1 | 1.25 |
| MCL119 | YES | LOW | INTERMEDIATE | <10 | 1 | 2.71 |
| MCL121 | YES | HIGH | NOT AVAILABLE | 10-29 | 0 | 9.68 |
| MCL122 | NO | HIGH | HIGH | 10-29 | 1 | 0.77 |
| MCL123 | YES | HIGH | HIGH | >=30 | 1 | 4.48 |
| MCL124 | NO | LOW | HIGH | 10-29 | 1 | 1.44 |
| MCL129 | NO | HIGH | INTERMEDIATE | >=30 | 1 | 1.51 |
| MCL131 | YES | STANDARD | LOW | >=30 | 0 | 6.57 |
| MCL134 | YES | STANDARD | LOW | >=30 | 0 | 6.18 |
| MCL138 | NO | HIGH | LOW | >=30 | 0 | 8.04 |
| MCL141 | NO | LOW | NOT AVAILABLE | >=30 | 0 | 2.77 |
| MCL143 | YES | LOW | INTERMEDIATE | <10 | 0 | 5.60 |
| MCL145 | NO | STANDARD | HIGH | >=30 | 1 | 1.16 |
| MCL146 | YES | LOW | LOW | <10 | 0 | 7.81 |
| MCL147 | YES | LOW | INTERMEDIATE | 10-29 | 1 | 6.21 |
| MCL148 | YES | STANDARD | INTERMEDIATE | >=30 | 1 | 5.87 |
| MCL149 | YES | LOW | LOW | >=30 | 0 | 2.99 |
| MCL150 | NO | STANDARD | INTERMEDIATE | >=30 | 0 | 3.50 |
| MCL152 | YES | STANDARD | HIGH | >=30 | 1 | 2.37 |
| MCL153 | YES | HIGH | INTERMEDIATE | >=30 | 0 | 6.28 |
| MCL154 | NO | LOW | NOT AVAILABLE | 10-29 | 1 | 4.38 |
| MCL155 | YES | STANDARD | HIGH | >=30 | 1 | 0.37 |

Table abbreviations: ASCT ITT: intention-to-treat with an autologous stem cell transplant; MIPI: mantle cell lymphoma International Prognostic Index; IHC: immunohistochemistry.
CODE_OS: 0 = alive at last follow-up, 1 = dead.

TABLE 5

Digital gene expression data for the MCL35 assay and CCND1 in the validation cohort

| Gene Name | Category | MCL001 | MCL002 | MCL006 | MCL007 | MCL008 | MCL009 |
|---|---|---|---|---|---|---|---|
| MKI67 | Proliferation | 451 | 42 | 253 | 407 | 234 | 204 |
| FOXM1 | Proliferation | 641 | 144 | 822 | 676 | 388 | 494 |
| ESPL1 | Proliferation | 427 | 58 | 168 | 498 | 204 | 192 |
| TOP2A | Proliferation | 753 | 109 | 494 | 686 | 316 | 391 |
| NCAPG | Proliferation | 433 | 50 | 349 | 426 | 232 | 215 |
| CDKN3 | Proliferation | 407 | 32 | 656 | 344 | 195 | 159 |
| CDC20 | Proliferation | 546 | 61 | 566 | 404 | 294 | 234 |
| KIF2C | Proliferation | 378 | 45 | 220 | 261 | 233 | 150 |
| H2AFX | Proliferation | 1051 | 85 | 494 | 787 | 435 | 396 |
| E2F2 | Proliferation | 699 | 92 | 157 | 467 | 317 | 300 |
| CCNB2 | Proliferation | 573 | 22 | 214 | 443 | 171 | 186 |
| FAM83D | Proliferation | 295 | 22 | 186 | 214 | 110 | 93 |
| ZWINT | Proliferation | 1685 | 168 | 660 | 1474 | 528 | 762 |
| ATL1 | Proliferation | 678 | 20 | 162 | 778 | 429 | 269 |
| FMNL3 | Proliferation | 3286 | 80 | 673 | 3862 | 1967 | 929 |
| ZDHHC21 | Proliferation | 4011 | 65 | 422 | 1859 | 1666 | 953 |
| GLIPR1 | Proliferation | 3915 | 54 | 2228 | 7601 | 3172 | 1343 |
| CHD4 | Housekeeper | 7539 | 206 | 2180 | 8991 | 4245 | 1940 |
| ERBB2IP | Housekeeper | 7062 | 185 | 1587 | 9091 | 4820 | 2235 |
| GIT2 | Housekeeper | 2432 | 70 | 579 | 2879 | 1514 | 919 |
| GSK3B | Housekeeper | 1045 | 46 | 480 | 1661 | 658 | 384 |
| HSPA9 | Housekeeper | 1546 | 77 | 710 | 1880 | 866 | 571 |

TABLE 5-continued

Digital gene expression data for the MCL35 assay and CCND1 in the validation cohort

| Gene Name | Category | | | | | |
|---|---|---:|---:|---:|---:|---:|---:|
| IK | Housekeeper | 2111 | 73 | 676 | 2155 | 1308 | 622 |
| MLL2 | Housekeeper | 2770 | 46 | 710 | 3230 | 1596 | 1031 |
| NEU3 | Housekeeper | 458 | 26 | 268 | 956 | 556 | 338 |
| R3HDM1 | Housekeeper | 2889 | 67 | 653 | 3178 | 1640 | 1106 |
| RANBP9 | Housekeeper | 3486 | 106 | 1518 | 4010 | 2117 | 1487 |
| RC3H2 | Housekeeper | 3517 | 116 | 961 | 2686 | 1963 | 875 |
| TRIM56 | Housekeeper | 2475 | 98 | 680 | 2601 | 1850 | 1101 |
| UBXN4 | Housekeeper | 2174 | 88 | 940 | 2966 | 1327 | 820 |
| VAC14 | Housekeeper | 2817 | 54 | 750 | 3049 | 1490 | 797 |
| VRK3 | Housekeeper | 2104 | 92 | 530 | 2294 | 1326 | 688 |
| WAC | Housekeeper | 4929 | 196 | 1502 | 5906 | 3067 | 1757 |
| WDR55 | Housekeeper | 1253 | 24 | 537 | 1553 | 718 | 431 |
| ZNF598 | Housekeeper | 1438 | 71 | 595 | 1674 | 957 | 601 |
| CCND1 | CCDN1 exonic | 82021 | 2201 | 3426 | 73008 | 27377 | 69939 |
| CCND1_A | CCDN1 probe A | 95705 | 1409 | 3736 | 75300 | 32629 | 87164 |
| CCND1_B | CCDN1 probe B | 52519 | 585 | 1898 | 33782 | 18592 | 44970 |

| Gene Name | Category | MCL010 | MCL011 | MCL012 | MCL015 | MCL016 | MCL017 |
|---|---|---:|---:|---:|---:|---:|---:|
| MKI67 | Proliferation | 149 | 83 | 772 | 372 | 163 | 196 |
| FOXM1 | Proliferation | 317 | 140 | 957 | 703 | 285 | 297 |
| ESPL1 | Proliferation | 161 | 80 | 560 | 452 | 163 | 238 |
| TOP2A | Proliferation | 239 | 118 | 888 | 1291 | 274 | 425 |
| NCAPG | Proliferation | 190 | 79 | 592 | 378 | 163 | 195 |
| CDKN3 | Proliferation | 141 | 63 | 526 | 428 | 167 | 348 |
| CDC20 | Proliferation | 184 | 95 | 822 | 604 | 193 | 274 |
| KIF2C | Proliferation | 168 | 61 | 388 | 438 | 245 | 171 |
| H2AFX | Proliferation | 379 | 256 | 984 | 910 | 480 | 632 |
| E2F2 | Proliferation | 243 | 101 | 1179 | 583 | 294 | 336 |
| CCNB2 | Proliferation | 118 | 38 | 487 | 478 | 143 | 220 |
| FAM83D | Proliferation | 74 | 30 | 290 | 224 | 92 | 123 |
| ZWINT | Proliferation | 669 | 218 | 1500 | 1269 | 853 | 597 |
| ATL1 | Proliferation | 479 | 200 | 295 | 381 | 537 | 259 |
| FMNL3 | Proliferation | 2152 | 1785 | 1751 | 1935 | 1710 | 1967 |
| ZDHHC21 | Proliferation | 2029 | 959 | 1406 | 1642 | 1689 | 1612 |
| GLIPR1 | Proliferation | 2780 | 2008 | 2349 | 2397 | 3046 | 2253 |
| CHD4 | Housekeeper | 3432 | 3150 | 3924 | 4283 | 5484 | 4106 |
| ERBB2IP | Housekeeper | 3743 | 2611 | 4275 | 4836 | 5154 | 3775 |
| GIT2 | Housekeeper | 1214 | 989 | 1624 | 1329 | 1311 | 1069 |
| GSK3B | Housekeeper | 749 | 668 | 700 | 1038 | 811 | 621 |
| HSPA9 | Housekeeper | 742 | 643 | 960 | 958 | 948 | 783 |
| IK | Housekeeper | 1061 | 771 | 1179 | 1081 | 1475 | 1157 |
| MLL2 | Housekeeper | 1361 | 1124 | 1366 | 1408 | 1630 | 1263 |
| NEU3 | Housekeeper | 483 | 435 | 611 | 624 | 594 | 491 |
| R3HDM1 | Housekeeper | 1136 | 898 | 1616 | 1903 | 1862 | 1425 |
| RANBP9 | Housekeeper | 1617 | 1349 | 2130 | 2663 | 2256 | 2002 |
| RC3H2 | Housekeeper | 1650 | 1406 | 1920 | 2627 | 2178 | 1940 |
| TRIM56 | Housekeeper | 1539 | 1481 | 1633 | 1404 | 1810 | 1280 |
| UBXN4 | Housekeeper | 1090 | 943 | 1524 | 1614 | 1566 | 1107 |
| VAC14 | Housekeeper | 1267 | 1095 | 1671 | 1494 | 1575 | 1234 |
| VRK3 | Housekeeper | 1247 | 889 | 1296 | 1130 | 1202 | 919 |
| WAC | Housekeeper | 2622 | 2183 | 2949 | 3648 | 3651 | 3099 |
| WDR55 | Housekeeper | 665 | 364 | 912 | 683 | 652 | 681 |
| ZNF598 | Housekeeper | 696 | 750 | 922 | 790 | 800 | 723 |
| CCND1 | CCDN1 exonic | 28605 | 23411 | 43704 | 27284 | 32417 | 18013 |
| CCND1_A | CCDN1 probe A | 27330 | 23479 | 42799 | 52579 | 42050 | 19355 |
| CCND1_B | CCDN1 probe B | 12810 | 9762 | 25736 | 22981 | 23044 | 6802 |

| Gene Name | Category | MCL018 | MCL019 | MCL020 | MCL021 | MCL022 | MCL023 |
|---|---|---:|---:|---:|---:|---:|---:|
| MKI67 | Proliferation | 4991 | 3236 | 1308 | 620 | 387 | 109 |
| FOXM1 | Proliferation | 10994 | 5841 | 2244 | 1676 | 700 | 289 |
| ESPL1 | Proliferation | 7697 | 3499 | 1450 | 773 | 341 | 169 |
| TOP2A | Proliferation | 6077 | 5411 | 2311 | 1498 | 450 | 281 |
| NCAPG | Proliferation | 4263 | 2844 | 1291 | 657 | 388 | 168 |
| CDKN3 | Ptoll feral ion | 3038 | 2823 | 1233 | 804 | 258 | 160 |
| CDC20 | Proliferation | 7136 | 3164 | 1329 | 804 | 527 | 233 |
| KIF2C | Proliferation | 4980 | 2649 | 1233 | 670 | 312 | 98 |
| H2AFX | Proliferation | 2729 | 3992 | 3617 | 2704 | 745 | 259 |
| E2F2 | Proliferation | 8202 | 4482 | 1892 | 1182 | 691 | 277 |
| CCNB2 | Proliferation | 3324 | 3516 | 1756 | 578 | 234 | 90 |
| FAM83D | Proliferation | 3259 | 1310 | 827 | 444 | 123 | 46 |
| ZWINT | Proliferation | 10993 | 7334 | 4003 | 2160 | 1496 | 571 |
| ATL1 | Proliferation | 244 | 1310 | 602 | 381 | 354 | 143 |
| FMNL3 | Proliferation | 800 | 5017 | 4096 | 4000 | 2354 | 986 |
| ZDHHC21 | Proliferation | 5205 | 5636 | 4471 | 3751 | 1875 | 919 |
| GLIPR1 | Proliferation | 3016 | 6224 | 5634 | 3556 | 3570 | 1021 |
| CHD4 | Housekeeper | 12383 | 16857 | 13713 | 8033 | 3265 | 2154 |

TABLE 5-continued

Digital gene expression data for the MCL35 assay and CCND1 in the validation cohort

| Gene Name | Category | | | | | |
|---|---|---|---|---|---|---|
| ERBB2IP | Housekeeper | 8434 | 11638 | 11684 | 11030 | 4328 | 1652 |
| GIT2 | Housekeeper | 2231 | 4191 | 3334 | 2599 | 1660 | 757 |
| GSK3B | Housekeeper | 1517 | 1972 | 1868 | 1586 | 912 | 475 |
| HSPA9 | Housekeeper | 2941 | 2459 | 1805 | 1345 | 903 | 435 |
| IK | Housekeeper | 2837 | 3350 | 2407 | 1962 | 1048 | 669 |
| MLL2 | Housekeeper | 2366 | 4507 | 3633 | 2632 | 1402 | 750 |
| NEU3 | Housekeeper | 1204 | 1247 | 1603 | 1181 | 674 | 219 |
| R3HDM1 | Housekeeper | 4112 | 4266 | 4085 | 2281 | 1961 | 678 |
| RANBP9 | Housekeeper | 5093 | 6254 | 6055 | 5270 | 1701 | 1164 |
| RC3H2 | Housekeeper | 4139 | 5482 | 5318 | 4865 | 2242 | 896 |
| TRIM56 | Housekeeper | 2870 | 3617 | 3351 | 3167 | 1975 | 750 |
| UBXN4 | Housekeeper | 2217 | 4331 | 3260 | 1780 | 1156 | 743 |
| VAC14 | Housekeeper | 2801 | 4343 | 3449 | 2533 | 1424 | 738 |
| VRK3 | Housekeeper | 2482 | 2779 | 2509 | 2133 | 1413 | 786 |
| WAC | Housekeeper | 6798 | 7343 | 9980 | 6940 | 3236 | 1500 |
| WDR55 | Housekeeper | 1998 | 2190 | 2097 | 1485 | 638 | 587 |
| ZNF598 | Housekeeper | 2667 | 2182 | 2181 | 1746 | 853 | 539 |
| CCND1 | CCDN1 exonic | 269048 | 70972 | 194373 | 49329 | 29722 | 22939 |
| CCND1_A | CCND1 probe A | 1386 | 44896 | 210072 | 76368 | 24270 | 17981 |
| CCND1_B | CCDN1 probe B | 177462 | 20820 | 102114 | 38119 | 10781 | 10799 |

| Gene Name | Category | MCL024 | MCL025 | MCL026 | MCL027 | MCL029 | MCL031 |
|---|---|---|---|---|---|---|---|
| MKI67 | Proliferation | 242 | 305 | 1084 | 470 | 403 | 1108 |
| FOXM1 | Proliferation | 519 | 773 | 1613 | 696 | 485 | 1682 |
| ESPL1 | Proliferation | 251 | 327 | 812 | 475 | 381 | 829 |
| TOP2A | Proliferation | 422 | 935 | 1525 | 682 | 552 | 1819 |
| NCAPG | Proliferation | 267 | 360 | 906 | 540 | 310 | 1057 |
| CDKN3 | Proliferation | 195 | 375 | 917 | 391 | 327 | 860 |
| CDC20 | Proliferation | 305 | 351 | 1375 | 501 | 480 | 1470 |
| KIF2C | Proliferation | 281 | 260 | 604 | 705 | 322 | 841 |
| H2AFX | Proliferation | 690 | 858 | 2045 | 787 | 695 | 1553 |
| E2F2 | Proliferation | 644 | 544 | 1147 | 693 | 777 | 1322 |
| CCNB2 | Proliferation | 208 | 317 | 802 | 370 | 237 | 880 |
| FAM83D | Proliferation | 102 | 223 | 768 | 263 | 118 | 477 |
| ZWINT | Proliferation | 836 | 1417 | 2096 | 2520 | 1154 | 2780 |
| ATL1 | Proliferation | 321 | 311 | 326 | 1206 | 692 | 384 |
| FMNL3 | Proliferation | 1744 | 849 | 2511 | 4251 | 5052 | 1210 |
| ZDHHC21 | Proliferation | 1849 | 1353 | 1864 | 6336 | 5708 | 1339 |
| GLIPR1 | Proliferation | 1895 | 1917 | 3731 | 7699 | 4569 | 2515 |
| CHD4 | Housekeeper | 3562 | 2990 | 7787 | 10726 | 7706 | 4738 |
| ERBB2IP | Housekeeper | 3625 | 3815 | 8489 | 10454 | 6898 | 5377 |
| GIT2 | Housekeeper | 1509 | 1236 | 2444 | 3726 | 2816 | 1665 |
| GSK3B | Housekeeper | 687 | 621 | 1520 | 1855 | 1434 | 1031 |
| HSPA9 | Housekeeper | 841 | 1062 | 1931 | 1930 | 1371 | 1439 |
| IK | Housekeeper | 926 | 885 | 1951 | 2467 | 1951 | 1328 |
| MLL2 | Housekeeper | 1420 | 1302 | 2520 | 3958 | 2921 | 2022 |
| NEU3 | Housekeeper | 614 | 566 | 1043 | 1182 | 634 | 819 |
| R3HDM1 | Housekeeper | 1599 | 1730 | 2836 | 3858 | 2481 | 2156 |
| RANBP9 | Housekeeper | 1780 | 2229 | 4363 | 4466 | 3300 | 2493 |
| RC3H2 | Housekeeper | 1881 | 1519 | 3773 | 3906 | 3330 | 1615 |
| TRIM56 | Housekeeper | 1720 | 1640 | 2409 | 3142 | 2519 | 2292 |
| UBXN4 | Housekeeper | 1270 | 1166 | 2684 | 2643 | 2290 | 1903 |
| VAC14 | Housekeeper | 1491 | 1548 | 2981 | 3471 | 2196 | 2110 |
| VRK3 | Housekeeper | 1175 | 1022 | 2058 | 2942 | 2146 | 1442 |
| WAC | Housekeeper | 3134 | 3469 | 5986 | 7150 | 5217 | 3716 |
| WDR55 | Housekeeper | 684 | 557 | 1460 | 2424 | 1572 | 1000 |
| ZNF598 | Housekeeper | 1006 | 994 | 1646 | 1936 | 1630 | 1117 |
| CCND1 | CCDN1 exonic | 32527 | 23686 | 37627 | 108732 | 74205 | 35908 |
| CCND1_A | CCND1 probe A | 35889 | 36210 | 51134 | 103154 | 65570 | 33714 |
| CCND1_B | CCDN1 probe B | 19832 | 17113 | 29673 | 65525 | 39615 | 21358 |

| Gene Name | Category | MCL033 | MCL035 | MCL036 | MCL037 | MCL038 | MCL040 |
|---|---|---|---|---|---|---|---|
| MKI67 | Proliferation | 263 | 316 | 307 | 483 | 1075 | 711 |
| FOXM1 | Proliferation | 337 | 598 | 578 | 967 | 1901 | 1560 |
| ESPL1 | Proliferation | 189 | 277 | 291 | 453 | 520 | 591 |
| TOP2A | Proliferation | 335 | 460 | 589 | 906 | 1601 | 1479 |
| NCAPG | Proliferation | 244 | 395 | 314 | 436 | 1197 | 751 |
| CDKN3 | Proliferation | 254 | 188 | 311 | 444 | 866 | 601 |
| CDC20 | Proliferation | 315 | 305 | 442 | 474 | 1558 | 864 |
| KIF2C | Proliferation | 167 | 193 | 323 | 357 | 637 | 580 |
| H2AFX | Proliferation | 504 | 630 | 863 | 1224 | 739 | 1328 |
| E2F2 | Proliferation | 236 | 394 | 745 | 907 | 880 | 1230 |
| CCNB2 | Proliferation | 176 | 183 | 308 | 222 | 705 | 557 |
| FAM83D | Proliferation | 103 | 126 | 194 | 220 | 418 | 461 |
| ZWINT | Proliferation | 617 | 862 | 739 | 1294 | 2694 | 2922 |
| ATL1 | Proliferation | 242 | 236 | 651 | 483 | 209 | 314 |

TABLE 5-continued

Digital gene expression data for the MCL35 assay and CCND1 in the validation cohort

| Gene Name | Category | | | | | |
|---|---|---|---|---|---|---|
| FMNL3 | Proliferation | 2152 | 485 | 3062 | 2243 | 487 | 1040 |
| ZDHHC21 | Proliferation | 2085 | 1246 | 2431 | 2632 | 1086 | 1376 |
| GLIPR1 | Proliferation | 2659 | 2375 | 3585 | 2876 | 1501 | 2004 |
| CHD4 | Housekeeper | 4040 | 2207 | 5882 | 6111 | 3919 | 3456 |
| ERBB2IP | Housekeeper | 3934 | 2933 | 4917 | 6786 | 2901 | 4212 |
| GIT2 | Housekeeper | 1517 | 1189 | 1540 | 1881 | 1127 | 1234 |
| GSK3B | Housekeeper | 728 | 613 | 1019 | 1349 | 705 | 654 |
| HSPA9 | Housekeeper | 773 | 641 | 1037 | 1250 | 1057 | 905 |
| IK | Housekeeper | 1308 | 652 | 1304 | 1825 | 912 | 1100 |
| MLL2 | Housekeeper | 1617 | 1019 | 1653 | 2408 | 824 | 1269 |
| NEU3 | Housekeeper | 487 | 418 | 586 | 717 | 542 | 472 |
| R3HDM1 | Housekeeper | 1482 | 1677 | 1738 | 2619 | 1657 | 1848 |
| RANBP9 | Housekeeper | 2084 | 1418 | 3126 | 3501 | 1514 | 2063 |
| RC3H2 | Housekeeper | 1872 | 1473 | 2565 | 3298 | 1777 | 1760 |
| TRIM56 | Housekeeper | 1810 | 1350 | 1627 | 2515 | 897 | 2035 |
| UBXN4 | Housekeeper | 1382 | 990 | 1581 | 2016 | 1043 | 1335 |
| VAC14 | Housekeeper | 1590 | 963 | 1552 | 1895 | 1115 | 1428 |
| VRK3 | Housekeeper | 1201 | 1123 | 1447 | 1586 | 796 | 1040 |
| WAC | Housekeeper | 3159 | 2022 | 3531 | 4937 | 1995 | 3153 |
| WDR55 | Housekeeper | 753 | 439 | 703 | 977 | 554 | 722 |
| ZNF598 | Housekeeper | 888 | 582 | 975 | 1128 | 950 | 845 |
| CCND1 | CCND1 exonic | 27511 | 26005 | 39463 | 45318 | 39601 | 38134 |
| CCND1_A | CCND1 probe A | 32542 | 26631 | 46941 | 50438 | 16652 | 58537 |
| CCND1_B | CCND1 probe B | 17315 | 12068 | 20503 | 19745 | 6494 | 27341 |

| Gene Name | Category | MCL041 | MCL042 | MCL043 | MCL044 | MCL045 | MCL047 |
|---|---|---|---|---|---|---|---|
| MKI67 | Proliferation | 159 | 385 | 1788 | 1664 | 119 | 154 |
| FOXM1 | Proliferation | 288 | 1600 | 2375 | 3243 | 235 | 532 |
| ESPL1 | Proliferation | 209 | 733 | 1396 | 1433 | 99 | 206 |
| TOP2A | Proliferation | 231 | 1306 | 1523 | 2560 | 193 | 363 |
| NCAPG | Proliferation | 178 | 700 | 1379 | 1745 | 132 | 199 |
| CDKN3 | Proliferation | 131 | 482 | 1614 | 1499 | 111 | 186 |
| CDC20 | Proliferation | 200 | 695 | 1885 | 1907 | 174 | 158 |
| KIF2C | Proliferation | 165 | 519 | 1106 | 1355 | 104 | 108 |
| H2AFX | Proliferation | 305 | 1075 | 2372 | 1855 | 283 | 627 |
| E2F2 | Proliferation | 208 | 1111 | 1469 | 1496 | 214 | 261 |
| CCNB2 | Proliferation | 127 | 452 | 1385 | 1926 | 78 | 122 |
| FAM83D | Proliferation | 55 | 222 | 1093 | 1112 | 46 | 81 |
| ZWINT | Proliferation | 543 | 683 | 3207 | 3580 | 405 | 685 |
| ATL1 | Proliferation | 287 | 50 | 128 | 562 | 274 | 137 |
| FMNL3 | Proliferation | 1796 | 232 | 1858 | 2355 | 1182 | 1582 |
| ZDHHC21 | Proliferation | 860 | 599 | 2208 | 3858 | 1558 | 1291 |
| GLIPR1 | Proliferation | 2045 | 1836 | 2927 | 3353 | 1854 | 1258 |
| CHD4 | Housekeeper | 2677 | 2206 | 5609 | 10984 | 2817 | 3628 |
| ERBB2IP | Housekeeper | 2746 | 2555 | 6072 | 10006 | 2708 | 2487 |
| GIT2 | Housekeeper | 1073 | 1093 | 1576 | 2908 | 1029 | 864 |
| GSK3B | Housekeeper | 408 | 429 | 1190 | 1691 | 445 | 283 |
| HSPA9 | Housekeeper | 680 | 901 | 1384 | 1693 | 628 | 482 |
| IK | Housekeeper | 858 | 591 | 1564 | 2158 | 795 | 729 |
| MLL2 | Housekeeper | 965 | 1050 | 2181 | 2861 | 1021 | 1093 |
| NEU3 | Housekeeper | 424 | 420 | 841 | 1028 | 417 | 266 |
| R3HDM1 | Housekeeper | 1380 | 1618 | 2705 | 3296 | 1112 | 1383 |
| RANBP9 | Housekeeper | 1656 | 1241 | 2848 | 4021 | 1710 | 1473 |
| RC3H2 | Housekeeper | 1410 | 854 | 2642 | 4393 | 1433 | 1254 |
| TRIM56 | Housekeeper | 1200 | 1187 | 1910 | 2169 | 1333 | 1083 |
| UBXN4 | Housekeeper | 950 | 824 | 1846 | 2541 | 1103 | 812 |
| VAC14 | Housekeeper | 931 | 891 | 2722 | 3207 | 1150 | 806 |
| VRK3 | Housekeeper | 878 | 769 | 1470 | 2240 | 995 | 730 |
| WAC | Housekeeper | 2172 | 1897 | 3958 | 5550 | 2434 | 2464 |
| WDR55 | Housekeeper | 522 | 360 | 1332 | 1647 | 454 | 444 |
| ZNF598 | Housekeeper | 658 | 526 | 1447 | 1469 | 656 | 611 |
| CCND1 | CCDN1 exonic | 21688 | 51111 | 34669 | 38034 | 34423 | 19141 |
| CCND1_A | CCDN1 probe A | 21367 | 541 | 11784 | 37700 | 28759 | 39175 |
| CCND1_B | CCDN1 probe B | 9655 | 269 | 1313 | 19305 | 14658 | 16110 |

| Gene Name | Category | MCL048 | MCL050 | MCL052 | MCL053 | MCL054 | MCL055 |
|---|---|---|---|---|---|---|---|
| MKI67 | Proliferation | 50 | 827 | 2996 | 628 | 1225 | 298 |
| FOXM1 | Proliferation | 198 | 1837 | 3859 | 1480 | 2161 | 533 |
| ESPL1 | Proliferation | 76 | 748 | 2437 | 504 | 1124 | 305 |
| TOP2A | Proliferation | 211 | 1704 | 3820 | 785 | 2418 | 482 |
| NCAPG | Proliferation | 114 | 858 | 3073 | 429 | 1311 | 339 |
| CDKN3 | Proliferation | 174 | 649 | 2045 | 545 | 939 | 286 |
| CDC20 | Proliferation | 112 | 1102 | 2652 | 893 | 1473 | 392 |
| KIF2C | Proliferation | 62 | 726 | 1934 | 514 | 981 | 268 |
| H2AFX | Proliferation | 502 | 1200 | 3236 | 1372 | 2506 | 624 |
| E2F2 | Proliferation | 152 | 1223 | 3506 | 1107 | 2013 | 518 |

TABLE 5-continued

Digital gene expression data for the MCL35 assay and CCND1 in the validation cohort

| Gene Name | Category | | | | | |
|---|---|---|---|---|---|---|
| CCNB2 | Proliferation | 73 | 610 | 1883 | 393 | 1491 | 252 |
| FAM83D | Proliferation | 67 | 475 | 1062 | 357 | 556 | 188 |
| ZWINT | Proliferation | 208 | 2486 | 6153 | 1924 | 4036 | 1110 |
| ATL1 | Proliferation | 75 | 112 | 304 | 126 | 582 | 506 |
| FMNL3 | Proliferation | 1056 | 1744 | 2943 | 1437 | 2516 | 2190 |
| ZDHHC21 | Proliferation | 1324 | 1075 | 3208 | 2200 | 4591 | 2704 |
| GLIPR1 | Proliferation | 2262 | 1654 | 5828 | 1845 | 4588 | 3577 |
| CHD4 | Housekeeper | 2328 | 4423 | 6937 | 3838 | 7842 | 4904 |
| ERBB2IP | Housekeeper | 2854 | 4312 | 9007 | 4475 | 7733 | 5017 |
| GIT2 | Housekeeper | 710 | 1304 | 3635 | 1360 | 2971 | 1671 |
| GSK3B | Housekeeper | 618 | 1070 | 1810 | 848 | 923 | 794 |
| HSPA9 | Housekeeper | 503 | 1296 | 1901 | 1187 | 1606 | 981 |
| IK | Housekeeper | 869 | 1443 | 2512 | 1154 | 2177 | 1403 |
| MLL2 | Housekeeper | 1068 | 1844 | 3777 | 1490 | 3227 | 1982 |
| NEU3 | Housekeeper | 449 | 734 | 1075 | 680 | 876 | 589 |
| R3HDM1 | Housekeeper | 1647 | 1784 | 4295 | 1439 | 2842 | 1841 |
| RANBP9 | Housekeeper | 1444 | 3015 | 3427 | 2494 | 4077 | 3475 |
| RC3H2 | Housekeeper | 1872 | 1976 | 4543 | 2228 | 3850 | 2356 |
| TRIM56 | Housekeeper | 1305 | 1890 | 2877 | 2069 | 2417 | 1790 |
| UBXN4 | Housekeeper | 744 | 1741 | 2477 | 1694 | 2759 | 1613 |
| VAC14 | Housekeeper | 887 | 2274 | 2695 | 1846 | 3249 | 1921 |
| VRK3 | Housekeeper | 567 | 1382 | 2695 | 1316 | 2194 | 1402 |
| WAC | Housekeeper | 3298 | 3769 | 6684 | 3654 | 5746 | 3535 |
| WDR55 | Housekeeper | 419 | 939 | 1571 | 857 | 1969 | 1021 |
| ZNF598 | Housekeeper | 642 | 1298 | 2102 | 1066 | 1497 | 1061 |
| CCND1 | CCDN1 exonic | 13861 | 30899 | 156762 | 20360 | 127270 | 61662 |
| CCND1_A | CCDN1 probe A | 34158 | 5003 | 1292 | 24066 | 134479 | 46876 |
| CCND1_B | CCDN1 probe B | 11987 | 2686 | 666 | 12031 | 82143 | 1170 |

| Gene Name | Category | MCL057 | MCL059 | MCL060 | MCL061 | MCL062 | MCL063 |
|---|---|---|---|---|---|---|---|
| MKI67 | Proliferation | 3281 | 269 | 246 | 936 | 635 | 78 |
| FOXM1 | Proliferation | 5067 | 447 | 400 | 1968 | 1003 | 265 |
| ESPL1 | Proliferation | 2665 | 299 | 289 | 1012 | 516 | 105 |
| TOP2A | Proliferation | 4172 | 363 | 421 | 2040 | 912 | 144 |
| NCAPG | Proliferation | 3210 | 298 | 292 | 923 | 698 | 118 |
| CDKN3 | Proliferation | 1545 | 203 | 209 | 857 | 618 | 53 |
| CDC20 | Proliferation | 2726 | 337 | 314 | 1333 | 651 | 60 |
| KIF2C | Proliferation | 1814 | 396 | 307 | 1138 | 488 | 73 |
| H2AFX | Proliferation | 2501 | 518 | 515 | 1357 | 1795 | 230 |
| E2F2 | Proliferation | 4265 | 473 | 535 | 1731 | 663 | 299 |
| CCNB2 | Proliferation | 1610 | 206 | 120 | 1086 | 577 | 34 |
| FAM83D | Proliferation | 961 | 98 | 102 | 726 | 363 | 37 |
| ZWINT | Proliferation | 8296 | 1038 | 853 | 3760 | 1599 | 498 |
| ATL1 | Proliferation | 191 | 532 | 877 | 463 | 643 | 180 |
| FMNL3 | Proliferation | 1569 | 3176 | 3806 | 2236 | 3577 | 1038 |
| ZDHHC21 | Proliferation | 3928 | 4767 | 4501 | 1974 | 2832 | 522 |
| GLIPR1 | Proliferation | 5914 | 2971 | 4115 | 2954 | 3110 | 966 |
| CHD4 | Housekeeper | 7252 | 4484 | 6273 | 8909 | 6082 | 1142 |
| ERBB2IP | Housekeeper | 8758 | 4707 | 5911 | 7654 | 6988 | 1369 |
| GIT2 | Housekeeper | 2696 | 1857 | 2657 | 1986 | 2058 | 598 |
| GSK3B | Housekeeper | 1728 | 864 | 1042 | 1763 | 1116 | 220 |
| HSPA9 | Housekeeper | 2574 | 962 | 1127 | 1729 | 1299 | 441 |
| IK | Housekeeper | 2267 | 1463 | 1565 | 1871 | 1480 | 386 |
| MLL2 | Housekeeper | 4062 | 1797 | 2158 | 2940 | 2243 | 533 |
| NEU3 | Housekeeper | 1622 | 609 | 693 | 950 | 820 | 229 |
| R3HDM1 | Housekeeper | 3308 | 1620 | 1923 | 3006 | 2263 | 693 |
| RANBP9 | Housekeeper | 4113 | 2366 | 3047 | 3788 | 3121 | 649 |
| RC3H2 | Housekeeper | 2300 | 2520 | 3164 | 3401 | 3165 | 520 |
| TRIM56 | Housekeeper | 3343 | 1767 | 2169 | 2043 | 2255 | 837 |
| UBXN4 | Housekeeper | 2653 | 1672 | 1828 | 2193 | 1884 | 530 |
| VAC14 | Housekeeper | 2865 | 1741 | 2252 | 2939 | 2158 | 487 |
| VRK3 | Housekeeper | 2482 | 1528 | 1719 | 1750 | 1948 | 754 |
| WAC | Housekeeper | 6238 | 3734 | 4808 | 4900 | 4395 | 1166 |
| WDR55 | Housekeeper | 1927 | 1144 | 1265 | 1277 | 1414 | 199 |
| ZNF598 | Housekeeper | 3014 | 1011 | 1321 | 1768 | 1212 | 487 |
| CCND1 | CCDN1 exonic | 179225 | 47941 | 54962 | 33967 | 36027 | 15295 |
| CCND1_A | CCDN1 probe A | 86947 | 30831 | 49807 | 33070 | 34852 | 12396 |
| CCND1_B | CCDN1 probe B | 41806 | 15775 | 26082 | 18610 | 17137 | 4740 |

| Gene Name | Category | MCL064 | MCL065 | MCL067 | MCL068 | MCL069 | MCL071 |
|---|---|---|---|---|---|---|---|
| MKI67 | Proliferation | 423 | 290 | 1549 | 325 | 834 | 109 |
| FOXM1 | Proliferation | 495 | 449 | 3356 | 481 | 1724 | 319 |
| ESPL1 | Proliferation | 357 | 356 | 1816 | 332 | 797 | 102 |
| TOP2A | Proliferation | 545 | 396 | 1947 | 455 | 1271 | 164 |
| NCAPG | Proliferation | 387 | 321 | 1845 | 273 | 740 | 121 |
| CDKN3 | Proliferation | 368 | 221 | 1128 | 230 | 590 | 117 |

TABLE 5-continued

Digital gene expression data for the MCL35 assay and CCND1 in the validation cohort

| Gene Name | Category | | | | | |
|---|---|---|---|---|---|---|
| CDC20 | Proliferation | 505 | 266 | 1633 | 284 | 617 | 308 |
| KIF2C | Proliferation | 300 | 276 | 1347 | 293 | 728 | 169 |
| H2AFX | Proliferation | 512 | 450 | 2814 | 564 | 1847 | 375 |
| E2F2 | Proliferation | 678 | 458 | 1696 | 489 | 1458 | 250 |
| CCNB2 | Proliferation | 340 | 310 | 1831 | 193 | 923 | 152 |
| FAM83D | Proliferation | 184 | 92 | 962 | 148 | 730 | 45 |
| ZWINT | Proliferation | 998 | 1353 | 4321 | 1174 | 2714 | 414 |
| ATL1 | Proliferation | 480 | 271 | 203 | 707 | 601 | 335 |
| FMNL3 | Proliferation | 2432 | 1877 | 3930 | 3368 | 1605 | 1709 |
| ZDHHC21 | Proliferation | 2821 | 2514 | 872 | 3373 | 638 | 792 |
| GLIPR1 | Proliferation | 2897 | 1914 | 1431 | 4060 | 3872 | 1055 |
| CHD4 | Housekeeper | 5722 | 5498 | 5323 | 7039 | 5225 | 2052 |
| ERBB2IP | Housekeeper | 4337 | 5149 | 4877 | 5656 | 5119 | 2258 |
| GIT2 | Housekeeper | 1783 | 1841 | 1375 | 2136 | 1860 | 899 |
| GSK3B | Housekeeper | 768 | 787 | 1160 | 954 | 829 | 438 |
| HSPA9 | Housekeeper | 1042 | 1168 | 1295 | 1431 | 1281 | 401 |
| IK | Housekeeper | 1396 | 1354 | 1006 | 1630 | 1336 | 436 |
| MLL2 | Housekeeper | 1827 | 2107 | 1327 | 2213 | 1789 | 700 |
| NEU3 | Housekeeper | 686 | 586 | 761 | 690 | 583 | 247 |
| R3HDM1 | Housekeeper | 1652 | 2148 | 2170 | 2432 | 2232 | 924 |
| RANBP9 | Housekeeper | 2335 | 2215 | 2301 | 2872 | 2348 | 885 |
| RC3H2 | Housekeeper | 2503 | 2792 | 2282 | 2396 | 2246 | 714 |
| TRIM56 | Housekeeper | 1737 | 1744 | 1372 | 2022 | 1698 | 1043 |
| UBXN4 | Housekeeper | 1849 | 1792 | 1296 | 1827 | 1568 | 554 |
| VAC14 | Housekeeper | 2289 | 2116 | 2138 | 1983 | 1849 | 692 |
| VRK3 | Housekeeper | 1208 | 1424 | 1368 | 1493 | 1332 | 665 |
| WAC | Housekeeper | 3550 | 3656 | 3422 | 4419 | 4624 | 1380 |
| WDR55 | Housekeeper | 992 | 1017 | 1000 | 1241 | 820 | 254 |
| ZNF598 | Housekeeper | 1047 | 887 | 1190 | 1023 | 1278 | 595 |
| CCND1 | CCDN1 exonic | 32332 | 42531 | 108825 | 59795 | 68614 | 34291 |
| CCND1_A | CCDN1 probe A | 31016 | 44175 | 3604 | 69977 | 15611 | 27997 |
| CCND1_B | CCDN1 probe B | 16831 | 28013 | 2055 | 37312 | 6042 | 9529 |

| Gene Name | Category | MCL072 | MCL074 | MCL075 | MCL076 | MCL078 | MCL079 |
|---|---|---|---|---|---|---|---|
| MKI67 | Proliferation | 2021 | 33 | 173 | 370 | 21 | 508 |
| FOXM1 | Proliferation | 2332 | 41 | 466 | 759 | 44 | 680 |
| ESPL1 | Proliferation | 1214 | 19 | 256 | 365 | 39 | 519 |
| TOP2A | Proliferation | 2536 | 32 | 353 | 810 | 53 | 327 |
| NCAPG | Proliferation | 1720 | 37 | 202 | 370 | 51 | 609 |
| CDKN3 | Proliferation | 1236 | 22 | 197 | 396 | 69 | 465 |
| CDC20 | Proliferation | 1344 | 30 | 173 | 394 | 39 | 643 |
| KIF2C | Proliferation | 1056 | 15 | 115 | 307 | 34 | 370 |
| H2AFX | Proliferation | 1690 | 90 | 512 | 1419 | 273 | 674 |
| E2F2 | Proliferation | 1843 | 28 | 353 | 573 | 64 | 1111 |
| CCNB2 | Proliferation | 1364 | 10 | 109 | 529 | 18 | 375 |
| FAM83D | Proliferation | 858 | 10 | 80 | 209 | 40 | 284 |
| ZWINT | Proliferation | 3799 | 118 | 693 | 1207 | 134 | 1806 |
| ATL1 | Proliferation | 459 | 75 | 207 | 383 | 212 | 657 |
| FMNL3 | Proliferation | 1896 | 593 | 1681 | 998 | 500 | 1333 |
| ZDHHC21 | Proliferation | 4036 | 304 | 1197 | 616 | 1612 | 2606 |
| GLIPR1 | Proliferation | 2798 | 634 | 2234 | 1783 | 3112 | 3421 |
| CHD4 | Housekeeper | 9421 | 663 | 2036 | 3339 | 3822 | 5277 |
| ERBB2IP | Housekeeper | 7666 | 893 | 2528 | 3932 | 3018 | 5847 |
| GIT2 | Housekeeper | 1968 | 375 | 1274 | 1166 | 1127 | 1774 |
| GSK3B | Housekeeper | 1194 | 171 | 432 | 584 | 614 | 1015 |
| HSPA9 | Housekeeper | 1742 | 228 | 460 | 415 | 626 | 1366 |
| IK | Housekeeper | 2037 | 206 | 572 | 987 | 1070 | 1658 |
| MLL2 | Housekeeper | 2746 | 297 | 898 | 1129 | 1607 | 2093 |
| NEU3 | Housekeeper | 880 | 151 | 346 | 654 | 387 | 805 |
| R3HDM1 | Housekeeper | 2714 | 355 | 1070 | 1820 | 1252 | 2059 |
| RANBP9 | Housekeeper | 3610 | 407 | 1279 | 2387 | 1949 | 3056 |
| RC3H2 | Housekeeper | 3660 | 358 | 1230 | 1055 | 1879 | 1708 |
| TRIM56 | Housekeeper | 2230 | 492 | 1048 | 1168 | 1608 | 1538 |
| UBXN4 | Housekeeper | 2598 | 352 | 879 | 982 | 915 | 1734 |
| VAC14 | Housekeeper | 2406 | 341 | 786 | 864 | 1125 | 2106 |
| VRK3 | Housekeeper | 1896 | 293 | 641 | 1028 | 964 | 1465 |
| WAC | Housekeeper | 4561 | 647 | 2528 | 2614 | 3175 | 4027 |
| WDR55 | Housekeeper | 1304 | 123 | 424 | 515 | 529 | 1173 |
| ZNF598 | Housekeeper | 1161 | 278 | 617 | 623 | 695 | 938 |
| CCND1 | CCDN1 exonic | 41735 | 5493 | 17378 | 49446 | 22666 | 58905 |
| CCND1_A | CCDN1 probe A | 48540 | 5453 | 24050 | 63738 | 30594 | 50676 |
| CCND1_B | CCDN1 probe B | 24716 | 2585 | 8871 | 25685 | 11960 | 19695 |

| Gene Name | Category | MCL080 | MCL082 | MCL083 | MCL085 | MCL088 | MCL089 |
|---|---|---|---|---|---|---|---|
| MKI67 | Proliferation | 626 | 404 | 344 | 725 | 530 | 1610 |
| FOXM1 | Proliferation | 999 | 574 | 676 | 989 | 1017 | 2734 |

TABLE 5-continued

Digital gene expression data for the MCL35 assay and CCND1 in the validation cohort

| Gene Name | Category | | | | | |
|---|---|---|---|---|---|---|---|
| ESPL1 | Proliferation | 482 | 351 | 383 | 655 | 614 | 1503 |
| TOP2A | Proliferation | 1048 | 707 | 669 | 959 | 1097 | 3520 |
| NCAPG | Proliferation | 497 | 362 | 300 | 763 | 499 | 1758 |
| CDKN3 | Proliferation | 545 | 467 | 399 | 457 | 483 | 1627 |
| CDC20 | Proliferation | 684 | 622 | 463 | 728 | 597 | 3218 |
| KIF2C | Proliferation | 485 | 363 | 257 | 327 | 680 | 2186 |
| H2AFX | Proliferation | 1170 | 758 | 1046 | 990 | 1178 | 3037 |
| E2F2 | Proliferation | 706 | 493 | 541 | 612 | 1264 | 2032 |
| CCNB2 | Proliferation | 495 | 379 | 247 | 426 | 566 | 1142 |
| FAM83D | Proliferation | 234 | 217 | 169 | 243 | 322 | 944 |
| ZWINT | Proliferation | 1230 | 1126 | 1237 | 1420 | 2116 | 4282 |
| ATL1 | Proliferation | 406 | 501 | 656 | 440 | 1627 | 175 |
| FMNL3 | Proliferation | 1724 | 3221 | 1751 | 1353 | 5988 | 1061 |
| ZDHHC21 | Proliferation | 1767 | 3927 | 2263 | 2769 | 5407 | 3512 |
| GLIPR1 | Proliferation | 3516 | 4752 | 3631 | 2982 | 6344 | 3906 |
| CHD4 | Housekeeper | 4668 | 7492 | 4534 | 2796 | 13926 | 9100 |
| ERBB2IP | Housekeeper | 5820 | 7346 | 5294 | 5426 | 10842 | 7744 |
| GIT2 | Housekeeper | 1720 | 2108 | 1647 | 2638 | 3485 | 2343 |
| GSK3B | Housekeeper | 867 | 1479 | 865 | 722 | 2470 | 1691 |
| HSPA9 | Housekeeper | 1093 | 1365 | 891 | 1140 | 1853 | 2504 |
| IK | Housekeeper | 1443 | 1891 | 1628 | 1178 | 2487 | 2275 |
| MLL2 | Housekeeper | 1873 | 2352 | 1947 | 1131 | 3503 | 2436 |
| NEU3 | Housekeeper | 761 | 815 | 685 | 841 | 1152 | 844 |
| R3HDM1 | Housekeeper | 2052 | 2243 | 2255 | 2023 | 3330 | 3039 |
| RANBP9 | Housekeeper | 3162 | 3367 | 2411 | 3826 | 5194 | 3862 |
| RC3H2 | Housekeeper | 2930 | 3155 | 2402 | 3313 | 5337 | 3279 |
| TRIM56 | Housekeeper | 2360 | 2136 | 1993 | 2209 | 2584 | 1986 |
| UBXN4 | Housekeeper | 1693 | 2265 | 1560 | 1688 | 2947 | 2231 |
| VAC14 | Housekeeper | 2084 | 2303 | 1747 | 2104 | 3143 | 3520 |
| VRK3 | Housekeeper | 1587 | 1821 | 1399 | 1213 | 2672 | 2184 |
| WAC | Housekeeper | 4390 | 4981 | 5356 | 4454 | 7337 | 5432 |
| WDR55 | Housekeeper | 887 | 1160 | 829 | 1260 | 1889 | 1494 |
| ZNF598 | Housekeeper | 1156 | 1216 | 1019 | 1019 | 1798 | 2073 |
| CCND1 | CCDN1 exonic | 43984 | 43200 | 33907 | 42450 | 74127 | 39997 |
| CCND1_A | CCDN1 probe A | 39428 | 38181 | 36476 | 36682 | 91063 | 21544 |
| CCND1_B | CCDN1 probe B | 20125 | 19024 | 17463 | 19623 | 48101 | 9440 |

| Gene Name | Category | MCL091 | MCL092 | MCL093 | MCL094 | MCL095 | MCL096 |
|---|---|---|---|---|---|---|---|
| MKI67 | Proliferation | 828 | 326 | 4313 | 2635 | 216 | 130 |
| FOXM1 | Proliferation | 2676 | 417 | 5166 | 3734 | 445 | 562 |
| ESPL1 | Proliferation | 832 | 348 | 3061 | 2772 | 143 | 170 |
| TOP2A | Proliferation | 3478 | 500 | 5058 | 5107 | 322 | 276 |
| NCAPG | Proliferation | 1549 | 287 | 3669 | 2237 | 201 | 172 |
| CDKN3 | Proliferation | 1054 | 273 | 4810 | 1849 | 137 | 99 |
| CDC20 | Proliferation | 811 | 413 | 4442 | 2748 | 214 | 182 |
| KIF2C | Proliferation | 478 | 300 | 2892 | 1146 | 158 | 153 |
| H2AFX | Proliferation | 1732 | 713 | 10638 | 3873 | 528 | 608 |
| E2F2 | Proliferation | 1768 | 297 | 5441 | 2607 | 266 | 350 |
| CCNB2 | Proliferation | 578 | 231 | 3425 | 2664 | 95 | 114 |
| FAM83D | Proliferation | 388 | 157 | 2013 | 1344 | 90 | 123 |
| ZWINT | Proliferation | 2318 | 963 | 8298 | 8061 | 725 | 727 |
| ATL1 | Proliferation | 135 | 252 | 903 | 408 | 291 | 212 |
| FMNL3 | Proliferation | 810 | 4690 | 5453 | 1593 | 1224 | 955 |
| ZDHHC21 | Proliferation | 966 | 3322 | 5638 | 2343 | 661 | 337 |
| GLIPR1 | Proliferation | 1515 | 3977 | 3965 | 2233 | 1429 | 1085 |
| CHD4 | Housekeeper | 2801 | 7469 | 12055 | 9334 | 1702 | 1843 |
| ERBB2IP | Housekeeper | 3672 | 7058 | 8362 | 7069 | 1854 | 1909 |
| GIT2 | Housekeeper | 763 | 2081 | 2929 | 2164 | 845 | 712 |
| GSK3B | Housekeeper | 643 | 1088 | 1384 | 1322 | 362 | 300 |
| HSPA9 | Housekeeper | 427 | 1583 | 2219 | 1834 | 611 | 469 |
| IK | Housekeeper | 661 | 1875 | 2532 | 1934 | 521 | 435 |
| MLL2 | Housekeeper | 1247 | 2229 | 3341 | 3495 | 887 | 732 |
| NEU3 | Housekeeper | 329 | 664 | 1735 | 851 | 294 | 310 |
| R3HDM1 | Housekeeper | 2310 | 2086 | 3784 | 3147 | 993 | 851 |
| RANBP9 | Housekeeper | 1628 | 3387 | 4237 | 4032 | 1031 | 990 |
| RC3H2 | Housekeeper | 1791 | 3712 | 5865 | 1990 | 975 | 658 |
| TRIM56 | Housekeeper | 1250 | 2074 | 2444 | 2142 | 1207 | 1066 |
| UBXN4 | Housekeeper | 726 | 1870 | 2731 | 2536 | 783 | 415 |
| VAC14 | Housekeeper | 774 | 1785 | 4281 | 2333 | 688 | 543 |
| VRK3 | Housekeeper | 722 | 1543 | 3339 | 2003 | 702 | 635 |
| WAC | Housekeeper | 3361 | 5004 | 7445 | 4740 | 1668 | 1824 |
| WDR55 | Housekeeper | 404 | 1190 | 1963 | 1130 | 276 | 253 |
| ZNF598 | Housekeeper | 799 | 1298 | 2151 | 1475 | 613 | 551 |
| CCND1 | CCDN1 exonic | 48022 | 40121 | 226145 | 43737 | 19782 | 18532 |
| CCND1_A | CCDN1 probe A | 501 | 43298 | 10503 | 54829 | 27682 | 31884 |
| CCND1_B | CCDN1 probe B | 235 | 25262 | 1220 | 27689 | 15292 | 11647 |

TABLE 5-continued

Digital gene expression data for the MCL35 assay and CCND1 in the validation cohort

| Gene Name | Category | MCL097 | MCL098 | MCL099 | MCL100 | MCL102 | MCL103 |
|---|---|---|---|---|---|---|---|
| MKI67 | Proliferation | 645 | 3 | 174 | 433 | 213 | 662 |
| FOXM1 | Proliferation | 1684 | 31 | 293 | 507 | 315 | 941 |
| ESPL1 | Proliferation | 889 | 4 | 248 | 404 | 176 | 628 |
| TOP2A | Proliferation | 882 | 13 | 330 | 666 | 261 | 857 |
| NCAPG | Proliferation | 753 | 10 | 189 | 374 | 150 | 559 |
| CDKN3 | Proliferation | 592 | 4 | 184 | 440 | 193 | 425 |
| CDC20 | Proliferation | 1226 | 8 | 251 | 574 | 260 | 604 |
| KIF2C | Proliferation | 867 | 6 | 232 | 410 | 170 | 538 |
| H2AFX | Proliferation | 1163 | 14 | 459 | 681 | 384 | 796 |
| E2F2 | Proliferation | 1203 | 9 | 342 | 718 | 287 | 950 |
| CCNB2 | Proliferation | 677 | 2 | 162 | 407 | 132 | 412 |
| FAM83D | Proliferation | 629 | 1 | 100 | 265 | 93 | 148 |
| ZWINT | Proliferation | 2504 | 25 | 598 | 1276 | 443 | 1430 |
| ATL1 | Proliferation | 163 | 12 | 586 | 1037 | 189 | 456 |
| FMNL3 | Proliferation | 1342 | 29 | 3429 | 3828 | 1476 | 2297 |
| ZDHHC21 | Proliferation | 1367 | 26 | 2920 | 6321 | 1236 | 2317 |
| GLIPR1 | Proliferation | 2518 | 26 | 3176 | 4727 | 1700 | 3167 |
| CHD4 | Housekeeper | 4526 | 50 | 6715 | 9777 | 3200 | 6864 |
| ERBB2IP | Housekeeper | 5294 | 86 | 5310 | 9393 | 3079 | 5185 |
| GIT2 | Housekeeper | 1491 | 50 | 1914 | 3949 | 1194 | 1673 |
| GSK3B | Housekeeper | 872 | 12 | 902 | 1393 | 515 | 964 |
| HSPA9 | Housekeeper | 1095 | 36 | 1254 | 1747 | 727 | 1257 |
| IK | Housekeeper | 1412 | 28 | 1523 | 2414 | 965 | 1619 |
| MLL2 | Housekeeper | 1832 | 21 | 2524 | 3123 | 1190 | 2178 |
| NEU3 | Housekeeper | 702 | 5 | 723 | 1010 | 392 | 474 |
| R3HDM1 | Housekeeper | 2093 | 30 | 2084 | 2570 | 1220 | 1744 |
| RANBP9 | Housekeeper | 2199 | 47 | 2838 | 3944 | 1769 | 3537 |
| RC3H2 | Housekeeper | 1849 | 36 | 3339 | 4204 | 1618 | 2145 |
| TRIM56 | Housekeeper | 1849 | 50 | 1930 | 1701 | 1390 | 1762 |
| UBXN4 | Housekeeper | 1535 | 40 | 1910 | 2696 | 1057 | 2059 |
| VAC14 | Housekeeper | 2297 | 19 | 1940 | 2500 | 1166 | 2075 |
| VRK3 | Housekeeper | 1325 | 31 | 1728 | 2032 | 899 | 1598 |
| WAC | Housekeeper | 4139 | 54 | 3858 | 5705 | 2470 | 4045 |
| WDR55 | Housekeeper | 956 | 5 | 1080 | 1443 | 498 | 854 |
| ZNF598 | Housekeeper | 1280 | 21 | 1652 | 1549 | 715 | 1309 |
| CCND1 | CCDN1 exonic | 30455 | 699 | 42981 | 63694 | 17680 | 39145 |
| CCND1_A | CCDN1 probe A | 36795 | 1080 | 45840 | 62178 | 20728 | 40908 |
| CCND1_B | CCDN1 probe B | 18280 | 525 | 22665 | 29575 | 10045 | 22895 |

| Gene Name | Category | MCL104 | MCL105 | MCL106 | MCL108 | MCL109 | MCL110 |
|---|---|---|---|---|---|---|---|
| MKI67 | Proliferation | 267 | 334 | 214 | 841 | 933 | 868 |
| FOXM1 | Proliferation | 375 | 792 | 488 | 1953 | 1418 | 2332 |
| ESPL1 | Proliferation | 290 | 376 | 196 | 1510 | 800 | 1070 |
| TOP2A | Proliferation | 442 | 535 | 541 | 1860 | 1213 | 2527 |
| NCAPG | Proliferation | 254 | 382 | 217 | 907 | 758 | 1473 |
| CDKN3 | Proliferation | 254 | 301 | 258 | 881 | 776 | 1422 |
| CDC20 | Proliferation | 326 | 481 | 216 | 1071 | 1112 | 1821 |
| KIF2C | Proliferation | 169 | 268 | 160 | 669 | 650 | 1260 |
| H2AFX | Proliferation | 524 | 973 | 771 | 2608 | 1503 | 746 |
| E2F2 | Proliferation | 275 | 680 | 340 | 1026 | 1089 | 1601 |
| CCNB2 | Proliferation | 212 | 261 | 151 | 687 | 656 | 1235 |
| FAM83D | Proliferation | 134 | 152 | 139 | 516 | 412 | 566 |
| ZWINT | Proliferation | 772 | 1299 | 935 | 3845 | 2238 | 3593 |
| ATL1 | Proliferation | 950 | 381 | 344 | 255 | 234 | 21 |
| FMNL3 | Proliferation | 2431 | 2096 | 1930 | 2727 | 1485 | 302 |
| ZDHHC21 | Proliferation | 3298 | 1189 | 2564 | 1739 | 3241 | 557 |
| GLIPR1 | Proliferation | 4321 | 1071 | 2439 | 5054 | 3748 | 495 |
| CHD4 | Housekeeper | 6338 | 3721 | 3479 | 4747 | 5988 | 3337 |
| ERBB2IP | Housekeeper | 5873 | 3117 | 3941 | 4651 | 6207 | 4957 |
| GIT2 | Housekeeper | 1818 | 1298 | 1057 | 1710 | 1726 | 543 |
| GSK3B | Housekeeper | 990 | 663 | 736 | 791 | 1037 | 679 |
| HSPA9 | Housekeeper | 1183 | 894 | 819 | 1115 | 1322 | 1401 |
| IK | Housekeeper | 1758 | 1127 | 995 | 1051 | 1839 | 845 |
| MLL2 | Housekeeper | 2244 | 1317 | 1233 | 1051 | 2304 | 1135 |
| NEU3 | Housekeeper | 699 | 483 | 532 | 517 | 766 | 361 |
| R3HDM1 | Housekeeper | 1862 | 1191 | 1971 | 2039 | 2333 | 3281 |
| RANBP9 | Housekeeper | 2697 | 1578 | 1848 | 2462 | 2625 | 3357 |
| RC3H2 | Housekeeper | 2797 | 1457 | 2036 | 2723 | 2909 | 855 |
| TRIM56 | Housekeeper | 1578 | 1175 | 1681 | 1586 | 2104 | 1125 |
| UBXN4 | Housekeeper | 1970 | 1384 | 1300 | 1437 | 1880 | 1363 |
| VAC14 | Housekeeper | 1870 | 829 | 1073 | 1610 | 1919 | 1079 |
| VRK3 | Housekeeper | 1388 | 766 | 977 | 1096 | 1606 | 824 |
| WAC | Housekeeper | 3880 | 2276 | 3272 | 3951 | 4212 | 2756 |
| WDR55 | Housekeeper | 1147 | 656 | 466 | 620 | 1126 | 477 |
| ZNF598 | Housekeeper | 1145 | 771 | 735 | 1267 | 1216 | 1505 |

TABLE 5-continued

Digital gene expression data for the MCL35 assay and CCND1 in the validation cohort

| | | | | | | | |
|---|---|---|---|---|---|---|---|
| CCND1 | CCDN1 exonic | 63355 | 62287 | 25158 | 66669 | 71412 | 60999 |
| CCND1_A | CCDN1 probe A | 51808 | 61162 | 43606 | 21974 | 1738 | 7988 |
| CCND1_B | CCDN1 probe B | 23116 | 30823 | 17321 | 10447 | 976 | 3928 |

| Gene Name | Category | MCL113 | MCL114 | MCL115 | MCL116 | MCL117 | MCL119 |
|---|---|---|---|---|---|---|---|
| MKI67 | Proliferation | 1054 | 139 | 794 | 149 | 504 | 157 |
| FOXM1 | Proliferation | 890 | 549 | 1474 | 278 | 819 | 257 |
| ESPL1 | Proliferation | 696 | 280 | 569 | 138 | 513 | 220 |
| TOP2A | Proliferation | 1392 | 521 | 1126 | 267 | 811 | 268 |
| NCAPG | Proliferation | 1152 | 201 | 490 | 176 | 383 | 150 |
| CDKN3 | Proliferation | 518 | 211 | 396 | 137 | 561 | 159 |
| CDC20 | Proliferation | 967 | 193 | 521 | 174 | 785 | 169 |
| KIF2C | Proliferation | 475 | 139 | 400 | 116 | 574 | 251 |
| H2AFX | Proliferation | 998 | 710 | 1564 | 488 | 937 | 435 |
| E2F2 | Proliferation | 568 | 591 | 695 | 293 | 702 | 202 |
| CCNB2 | Proliferation | 458 | 126 | 394 | 147 | 471 | 124 |
| FAM83D | Proliferation | 468 | 115 | 356 | 66 | 184 | 101 |
| ZWINT | Proliferation | 1802 | 671 | 1207 | 492 | 991 | 521 |
| ATL1 | Proliferation | 137 | 202 | 47 | 297 | 183 | 535 |
| FMNL3 | Proliferation | 1326 | 1719 | 682 | 1487 | 1074 | 3049 |
| ZDHHC21 | Proliferation | 926 | 1777 | 996 | 1251 | 1827 | 2648 |
| GLIPR1 | Proliferation | 2119 | 1673 | 1245 | 1927 | 2740 | 3939 |
| CHD4 | Housekeeper | 2391 | 2489 | 2251 | 3151 | 3465 | 6222 |
| ERBB2IP | Housekeeper | 3919 | 3247 | 3026 | 3211 | 4313 | 5162 |
| GIT2 | Housekeeper | 710 | 932 | 970 | 1277 | 1389 | 1891 |
| GSK3B | Housekeeper | 686 | 506 | 635 | 763 | 780 | 881 |
| HSPA9 | Housekeeper | 952 | 510 | 820 | 810 | 947 | 1242 |
| IK | Housekeeper | 831 | 563 | 620 | 753 | 961 | 1406 |
| MLL2 | Housekeeper | 1183 | 966 | 1108 | 1219 | 1461 | 2115 |
| NEU3 | Housekeeper | 440 | 457 | 368 | 428 | 618 | 650 |
| R3HDM1 | Housekeeper | 1763 | 1355 | 1485 | 1305 | 1906 | 1768 |
| RANBP9 | Housekeeper | 1797 | 1723 | 1047 | 1333 | 1543 | 2170 |
| RC3H2 | Housekeeper | 2062 | 2306 | 1071 | 1450 | 2140 | 2094 |
| TRIM56 | Housekeeper | 1571 | 1493 | 1319 | 1450 | 1462 | 1945 |
| UBXN4 | Housekeeper | 1006 | 855 | 676 | 991 | 1371 | 1733 |
| VAC14 | Housekeeper | 1373 | 840 | 1076 | 1136 | 1602 | 1709 |
| VRK3 | Housekeeper | 1058 | 915 | 814 | 1033 | 1095 | 1557 |
| WAC | Housekeeper | 3098 | 3126 | 2404 | 2536 | 4762 | 3909 |
| WDR55 | Housekeeper | 549 | 344 | 527 | 427 | 619 | 807 |
| ZNF598 | Housekeeper | 1044 | 838 | 964 | 802 | 1328 | 1150 |
| CCND1 | CCDN1 exonic | 35131 | 28710 | 20694 | 28124 | 28528 | 58155 |
| CCND1_A | CCDN1 probe A | 25068 | 53146 | 10824 | 34064 | 27184 | 61184 |
| CCND1_B | CCDN1 probe B | 4185 | 19956 | 1574 | 18365 | 15336 | 35661 |

| Gene Name | Category | MCL121 | MCL122 | MCL123 | MCL124 | MCL129 | MCL131 |
|---|---|---|---|---|---|---|---|
| MKI67 | Proliferation | 250 | 82 | 140 | 267 | 801 | 670 |
| FOXM1 | Proliferation | 514 | 394 | 339 | 481 | 1594 | 1179 |
| ESPL1 | Proliferation | 218 | 107 | 116 | 209 | 567 | 482 |
| TOP2A | Proliferation | 451 | 514 | 486 | 483 | 897 | 975 |
| NCAPG | Proliferation | 221 | 149 | 148 | 249 | 811 | 649 |
| CDKN3 | Proliferation | 363 | 141 | 179 | 283 | 368 | 451 |
| CDC20 | Proliferation | 406 | 94 | 285 | 319 | 448 | 732 |
| KIF2C | Proliferation | 158 | 87 | 125 | 208 | 452 | 448 |
| H2AFX | Proliferation | 666 | 362 | 317 | 705 | 693 | 976 |
| E2F2 | Proliferation | 498 | 222 | 176 | 373 | 817 | 825 |
| CCNB2 | Proliferation | 163 | 58 | 91 | 224 | 280 | 423 |
| FAM83D | Proliferation | 120 | 34 | 85 | 159 | 224 | 259 |
| ZWINT | Proliferation | 659 | 401 | 317 | 898 | 1815 | 2244 |
| ATL1 | Proliferation | 82 | 75 | 23 | 368 | 76 | 468 |
| FMNL3 | Proliferation | 689 | 276 | 134 | 2641 | 1459 | 1336 |
| ZDHHC21 | Proliferation | 530 | 208 | 286 | 1864 | 519 | 1435 |
| GLIPR1 | Proliferation | 515 | 171 | 221 | 3109 | 1857 | 2285 |
| CHD4 | Housekeeper | 1244 | 681 | 608 | 5432 | 1715 | 3606 |
| ERBB2IP | Housekeeper | 1592 | 696 | 616 | 5813 | 2884 | 4264 |
| GIT2 | Housekeeper | 435 | 225 | 208 | 1568 | 1248 | 1441 |
| GSK3B | Housekeeper | 238 | 193 | 93 | 924 | 528 | 542 |
| HSPA9 | Housekeeper | 302 | 168 | 212 | 1171 | 858 | 896 |
| IK | Housekeeper | 336 | 169 | 182 | 1212 | 542 | 1021 |
| MLL2 | Housekeeper | 419 | 189 | 191 | 1827 | 1103 | 1326 |
| NEU3 | Housekeeper | 201 | 110 | 90 | 652 | 594 | 661 |
| R3HDM1 | Housekeeper | 644 | 461 | 201 | 1631 | 1207 | 1656 |
| RANBP9 | Housekeeper | 679 | 393 | 308 | 2614 | 1196 | 1819 |
| RC3H2 | Housekeeper | 733 | 236 | 360 | 2246 | 652 | 1879 |
| TRIM56 | Housekeeper | 521 | 342 | 286 | 1836 | 1443 | 1765 |
| UBXN4 | Housekeeper | 422 | 188 | 199 | 1732 | 909 | 1208 |
| VAC14 | Housekeeper | 460 | 180 | 266 | 1523 | 1051 | 1596 |

TABLE 5-continued

Digital gene expression data for the MCL35 assay and CCND1 in the validation cohort

| Gene Name | Category | | | | | |
|---|---|---|---|---|---|---|
| VRK3 | Housekeeper | 438 | 245 | 205 | 1633 | 952 | 1104 |
| WAC | Housekeeper | 1084 | 953 | 815 | 3871 | 2066 | 3085 |
| WDR55 | Housekeeper | 201 | 77 | 84 | 810 | 523 | 675 |
| ZNF598 | Housekeeper | 344 | 253 | 292 | 987 | 1029 | 849 |
| CCND1 | CCDN1 exonic | 7143 | 6904 | 4989 | 33568 | 38241 | 28370 |
| CCND1_A | CCDN1 probe A | 8871 | 6272 | 7950 | 37515 | 7302 | 32111 |
| CCND1_B | CCDN1 probe B | 4718 | 1844 | 4864 | 16005 | 3635 | 18005 |

| Gene Name | Category | MCL134 | MCL138 | MCL141 | MCL143 | MCL145 | MCL146 |
|---|---|---|---|---|---|---|---|
| MKI67 | Proliferation | 989 | 1719 | 253 | 123 | 220 | 87 |
| FOXM1 | Proliferation | 1638 | 2707 | 757 | 204 | 347 | 244 |
| ESPL1 | Proliferation | 812 | 1302 | 380 | 131 | 157 | 75 |
| TOP2A | Proliferation | 1482 | 1784 | 529 | 269 | 216 | 187 |
| NCAPG | Proliferation | 822 | 1331 | 337 | 143 | 230 | 88 |
| CDKN3 | Proliferation | 923 | 1342 | 334 | 140 | 127 | 98 |
| CDC20 | Proliferation | 942 | 2006 | 269 | 161 | 221 | 121 |
| KIF2C | Proliferation | 779 | 1187 | 278 | 111 | 192 | 62 |
| H2AFX | Proliferation | 1385 | 3059 | 1518 | 398 | 612 | 373 |
| E2F2 | Proliferation | 941 | 1084 | 1089 | 252 | 389 | 172 |
| CCNB2 | Proliferation | 1069 | 1269 | 241 | 107 | 127 | 55 |
| FAM83D | Proliferation | 716 | 994 | 155 | 84 | 101 | 44 |
| ZWINT | Proliferation | 2608 | 4064 | 1382 | 453 | 938 | 286 |
| ATL1 | Proliferation | 458 | 180 | 309 | 289 | 141 | 128 |
| FMNL3 | Proliferation | 1909 | 1728 | 2409 | 1951 | 923 | 1056 |
| ZDHHC21 | Proliferation | 1659 | 1064 | 1975 | 1494 | 662 | 791 |
| GLIPR1 | Proliferation | 4889 | 4617 | 2440 | 1983 | 678 | 1605 |
| CHD4 | Housekeeper | 6048 | 5602 | 4015 | 3240 | 1013 | 1603 |
| ERBB2IP | Housekeeper | 7066 | 6759 | 5044 | 3333 | 1647 | 2073 |
| GIT2 | Housekeeper | 3120 | 1528 | 1052 | 1044 | 684 | 706 |
| GSK3B | Housekeeper | 932 | 1071 | 751 | 497 | 252 | 424 |
| HSPA9 | Housekeeper | 1389 | 1878 | 667 | 710 | 491 | 396 |
| IK | Housekeeper | 1503 | 1647 | 965 | 1043 | 364 | 522 |
| MLL2 | Housekeeper | 2139 | 1873 | 1393 | 1193 | 531 | 641 |
| NEU3 | Housekeeper | 1027 | 685 | 677 | 448 | 337 | 311 |
| R3HDM1 | Housekeeper | 2362 | 1739 | 1948 | 1202 | 701 | 786 |
| RANBP9 | Housekeeper | 3280 | 3475 | 2499 | 1550 | 964 | 1074 |
| RC3H2 | Housekeeper | 3169 | 2722 | 2340 | 1543 | 769 | 1019 |
| TRIM56 | Housekeeper | 1921 | 1560 | 1368 | 1336 | 796 | 1042 |
| UBXN4 | Housekeeper | 1919 | 2038 | 1139 | 865 | 693 | 588 |
| VAC14 | Housekeeper | 2449 | 2959 | 1196 | 1195 | 607 | 647 |
| VRK3 | Housekeeper | 1890 | 1204 | 1299 | 834 | 604 | 567 |
| WAC | Housekeeper | 4834 | 4643 | 2956 | 2552 | 1672 | 1801 |
| WDR55 | Housekeeper | 1201 | 1481 | 774 | 475 | 256 | 220 |
| ZNF598 | Housekeeper | 1168 | 2023 | 731 | 777 | 459 | 502 |
| CCND1 | CCDN1 exonic | 80302 | 40921 | 37608 | 23197 | 10373 | 10023 |
| CCND1_A | CCDN1 probe A | 72162 | 3332 | 74164 | 24031 | 11775 | 13017 |
| CCND1_B | CCDN1 probe B | 42136 | 30666 | 27752 | 10177 | 5547 | 4100 |

| Gene Name | Category | MCL147 | MCL148 | MCL149 | MCL150 | MCL152 | MCL153 |
|---|---|---|---|---|---|---|---|
| MKI67 | Proliferation | 467 | 676 | 504 | 622 | 790 | 615 |
| FOXM1 | Proliferation | 774 | 955 | 756 | 684 | 1007 | 889 |
| ESPL1 | Proliferation | 432 | 444 | 496 | 456 | 750 | 302 |
| TOP2A | Proliferation | 646 | 876 | 788 | 695 | 1228 | 638 |
| NCAPG | Proliferation | 505 | 619 | 479 | 479 | 594 | 638 |
| CDKN3 | Proliferation | 349 | 586 | 491 | 403 | 755 | 491 |
| CDC20 | Proliferation | 451 | 702 | 707 | 552 | 799 | 526 |
| KIF2C | Proliferation | 360 | 467 | 447 | 390 | 551 | 338 |
| H2AFX | Proliferation | 833 | 1127 | 837 | 598 | 1203 | 806 |
| E2F2 | Proliferation | 498 | 970 | 600 | 690 | 772 | 459 |
| CCNB2 | Proliferation | 355 | 441 | 457 | 371 | 903 | 291 |
| FAM83D | Proliferation | 226 | 277 | 248 | 330 | 320 | 223 |
| ZWINT | Proliferation | 1519 | 1921 | 1990 | 1460 | 1971 | 1640 |
| ATL1 | Proliferation | 491 | 361 | 465 | 239 | 483 | 136 |
| FMNL3 | Proliferation | 2748 | 2303 | 2858 | 1526 | 3712 | 1021 |
| ZDHHC21 | Proliferation | 1810 | 2040 | 2857 | 1126 | 2291 | 689 |
| GLIPR1 | Proliferation | 3406 | 2510 | 4315 | 3032 | 2559 | 766 |
| CHD4 | Housekeeper | 4723 | 4564 | 6401 | 3464 | 9555 | 1912 |
| ERBB2IP | Housekeeper | 5537 | 4856 | 6578 | 4009 | 5518 | 2152 |
| GIT2 | Housekeeper | 1623 | 1684 | 2061 | 1620 | 1493 | 789 |
| GSK3B | Housekeeper | 835 | 716 | 910 | 608 | 845 | 444 |
| HSPA9 | Housekeeper | 1050 | 1105 | 1357 | 1113 | 1667 | 1003 |
| IK | Housekeeper | 1190 | 1428 | 1876 | 1220 | 1621 | 606 |
| MLL2 | Housekeeper | 1736 | 1546 | 2201 | 1597 | 1852 | 800 |
| NEU3 | Housekeeper | 684 | 769 | 848 | 626 | 991 | 381 |
| R3HDM1 | Housekeeper | 1807 | 1723 | 2316 | 1210 | 1896 | 1036 |
| RANBP9 | Housekeeper | 2736 | 2519 | 2687 | 1723 | 3281 | 1496 |

TABLE 5-continued

Digital gene expression data for the MCL35 assay and CCND1 in the validation cohort

| Gene Name | Category | | | | | |
|---|---|---|---|---|---|---|
| RC3H2 | Housekeeper | 2186 | 2071 | 2918 | 1898 | 2569 | 863 |
| TRIM56 | Housekeeper | 1792 | 1800 | 1971 | 1512 | 1620 | 1261 |
| UBXN4 | Housekeeper | 1609 | 1618 | 2081 | 1228 | 2071 | 808 |
| VAC14 | Housekeeper | 1819 | 1555 | 2400 | 1840 | 1713 | 1077 |
| VRK3 | Housekeeper | 1333 | 1371 | 1660 | 1061 | 1504 | 691 |
| WAC | House keeper | 4056 | 3105 | 4610 | 3213 | 3553 | 1729 |
| WDR55 | Housekeeper | 796 | 861 | 1043 | 971 | 935 | 526 |
| ZNF598 | Housekeeper | 1021 | 1009 | 1187 | 855 | 1383 | 741 |
| CCND1 | CCDN1 exonic | 43833 | 54884 | 43727 | 23334 | 54688 | 14066 |
| CCND1_A | CCDN1 probe A | 47601 | 42919 | 48136 | 22448 | 47026 | 14884 |
| CCND1_B | CCDN1 probe B | 22416 | 22568 | 24108 | 13227 | 23209 | 7481 |

| Gene Name | Category | MCL154 | MCL155 |
|---|---|---|---|
| MKI67 | Proliferation | 240 | 1174 |
| FOXM1 | Proliferation | 335 | 1722 |
| ESPL1 | Proliferation | 207 | 664 |
| TOP2A | Proliferation | 361 | 2105 |
| NCAPG | Proliferation | 196 | 1040 |
| CDKN3 | Proliferation | 178 | 770 |
| CDC20 | Proliferation | 274 | 1113 |
| KIF2C | Proliferation | 127 | 648 |
| H2AFX | Proliferation | 485 | 796 |
| E2F2 | Proliferation | 249 | 1141 |
| CCNB2 | Proliferation | 161 | 878 |
| FAM83D | Proliferation | 96 | 416 |
| ZWINT | Proliferation | 725 | 2583 |
| ATL1 | Proliferation | 386 | 215 |
| FMNL3 | Proliferation | 1003 | 1817 |
| ZDHHC21 | Proliferation | 1744 | 1489 |
| GLIPR1 | Proliferation | 4436 | 4860 |
| CHD4 | Housekeeper | 3460 | 5908 |
| ERBB2IP | Housekeeper | 3764 | 4781 |
| GIT2 | Housekeeper | 1372 | 1427 |
| GSH3B | Housekeeper | 920 | 790 |
| HSPA9 | Housekeeper | 794 | 1103 |
| IK | Housekeeper | 1022 | 1219 |
| MLL2 | Housekeeper | 1362 | 2182 |
| NEU3 | Housekeeper | 493 | 567 |
| R3HDM1 | Housekeeper | 1414 | 1812 |
| RANBP9 | Housekeeper | 1477 | 2667 |
| RC3H2 | Housekeeper | 1473 | 2616 |
| TRIM56 | Housekeeper | 1426 | 1973 |
| UBXN4 | Housekeeper | 1128 | 1700 |
| VAC14 | Housekeeper | 1164 | 1651 |
| VRK3 | Housekeeper | 1061 | 1274 |
| WAC | Housekeeper | 2572 | 2864 |
| WDR55 | Housekeeper | 581 | 769 |
| ZNF598 | Housekeeper | 844 | 1145 |
| CCND1 | CCDN1 exonic | 22851 | 106606 |
| CCND1_A | CCDN1 probe A | 18512 | 896 |
| CCND1_B | CCDN1 probe B | 7603 | 361 |

CCND1 3' UTR Analysis

Figure 4A:
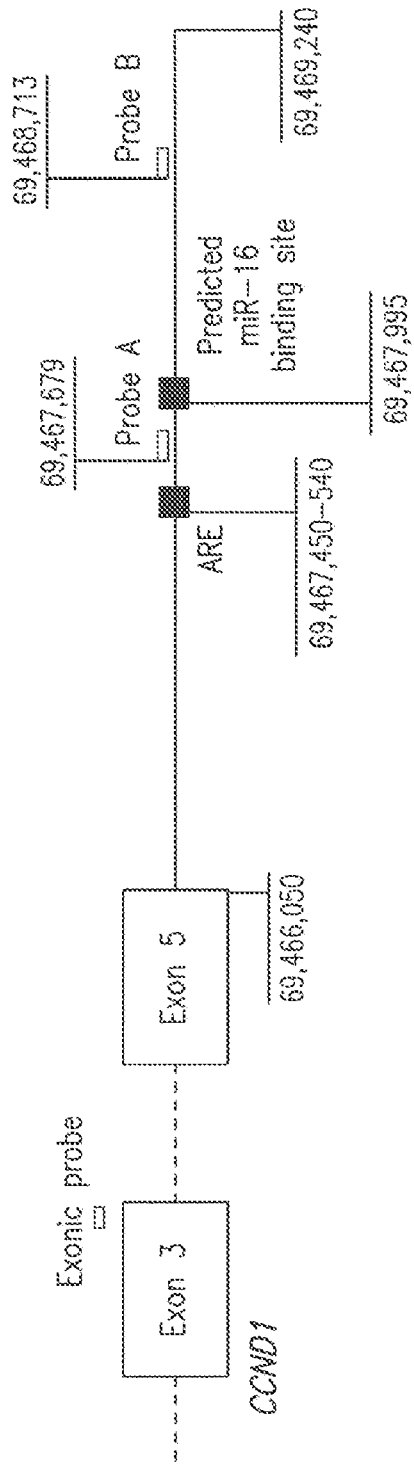
FIG. 4A is a diagram of CCND1 showing the location of the sites of binding of the NanoString® probes. The exonic probe targets a region within exon 3, while probe A binds between the Au-rich element (ARE) and the putative binding sites for miR-16 within the 3'UTR and probe B binds downstream of these elements. Coordinates are shown on chromosome 11 (Hg19).
Figure 4B:
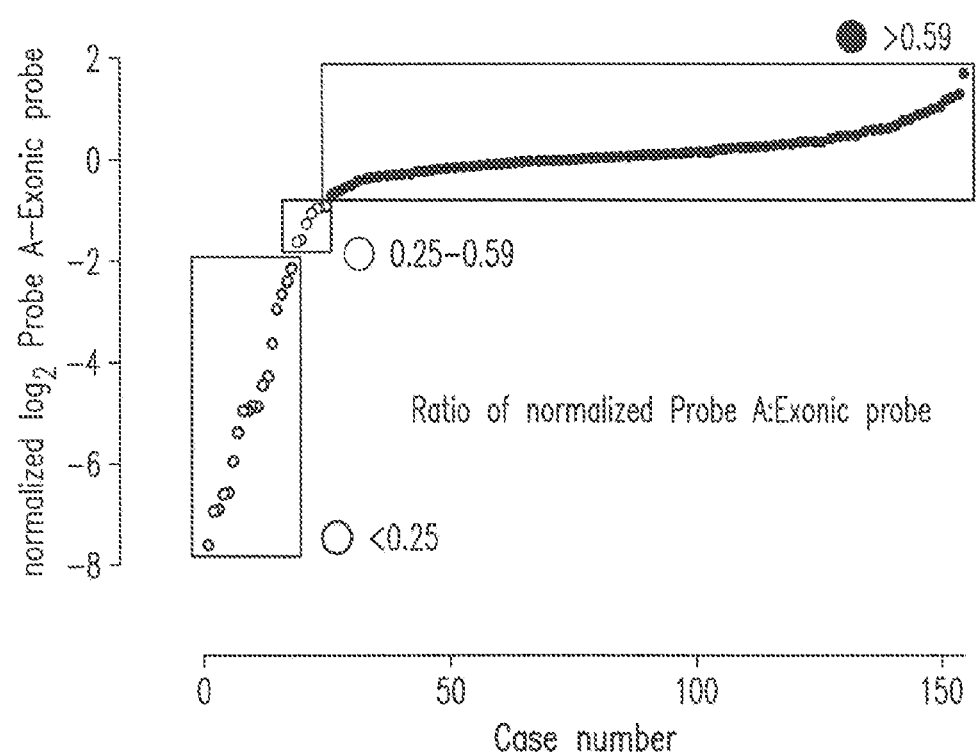
FIG. 4B shows the difference of the log 2 normalized expression of probe A and the exonic probe for CCND1, ordered in ascending values, left to right, in the training and validation cohort. The dots indicate biopsies with truncated CCND1 3' UTR mRNA: transcripts with low relative 3' UTR counts (ratio of <0.25 for normalized counts), moderately low relative 3'UTR counts (ratio between 0.25 to 0.59 for normalized counts), or no evidence for truncated CCND1 3' UTR mRNA transcripts (ratio >0.59 for normalized counts).
Figure 4C:
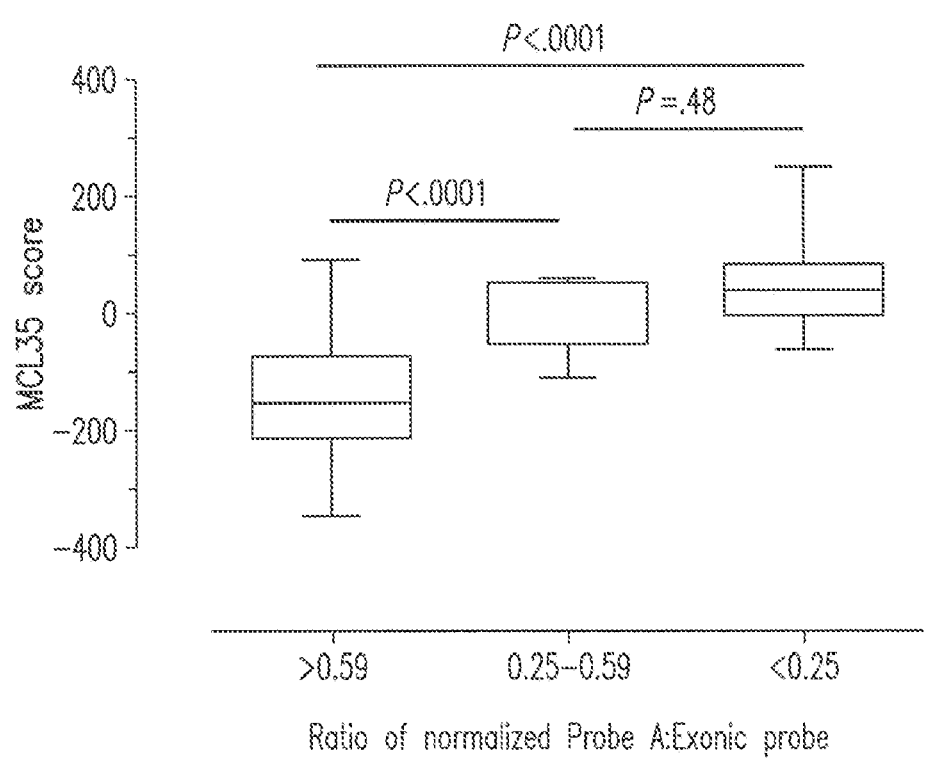
FIG. 4C shows the MCL35 scores in the three categories of relative 3' UTR expression identified in FIG. 4B displayed as box and whisker plots. Pairwise comparisons were made using Mann-Whitney tests.
Figure 4D:
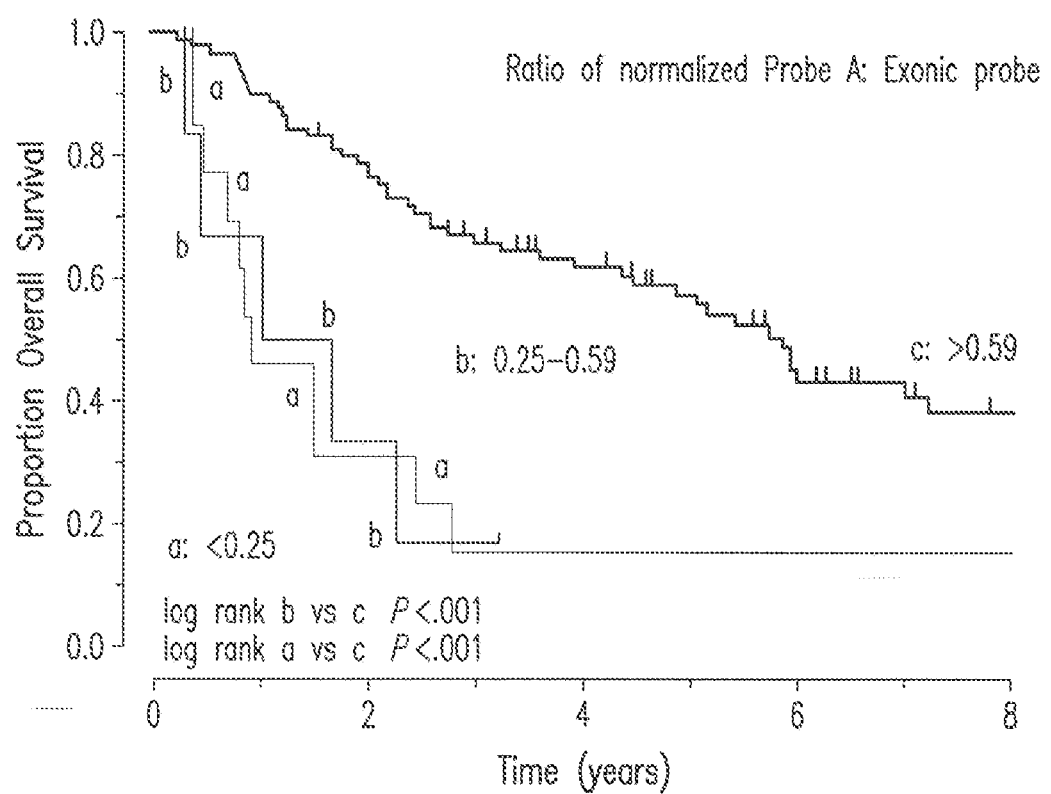
FIG. 4D shows Kaplan-Meier curves of overall survival for the three categories of relative 3'UTR expression identified in FIG. 4B in the validation cohort.
Figure 5A:
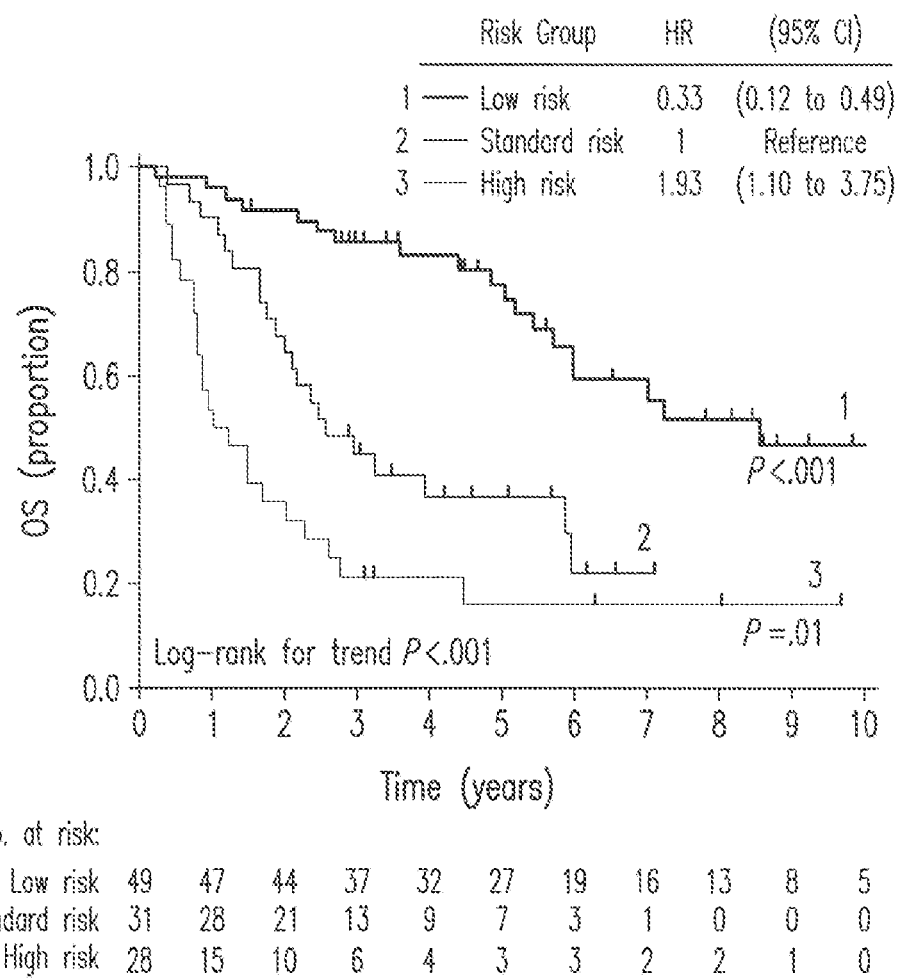
FIG. 5A shows Kaplan-Meier curves of the overall survival (OS) of the three patient groups in the validation cohort identified by the MCL35 assay. Hazard ratios (HR) are reported with the standard-risk group used as the reference.
Figure 5B:
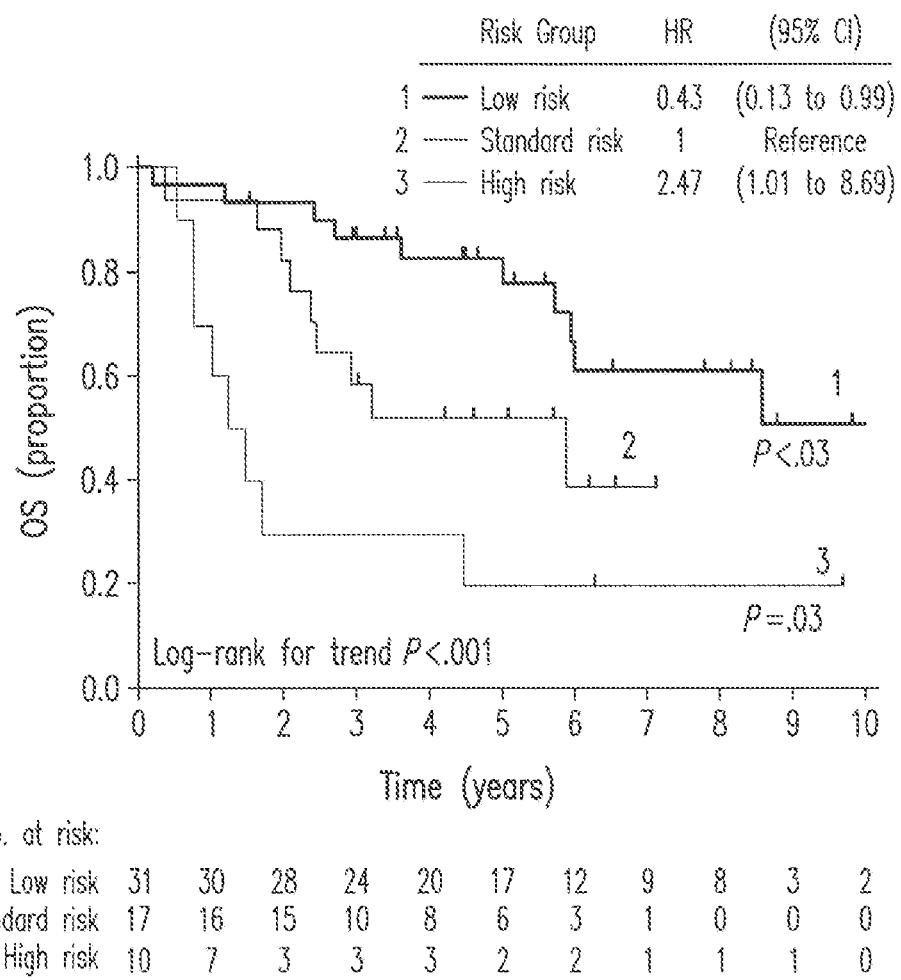
FIG. 5B shows Kaplan-Meier curves of the overall survival of the three patient groups within the subgroup of patients for whom there was an intention to consolidate response with an autologous stem-cell transplantation (ASCT). HRs are reported with the standard-risk group used as the reference. IHC, immunohistochemistry; UTR, untranslated region.

Truncation of the 3'UTR of CCND1 mRNA transcripts leads to increased mRNA stability, higher levels of CCND1 mRNA levels, and higher proliferation. The position of 2 putative regions that control degradation of the CCND1 transcript are the ARE element and the predicted binding site of miR-16. Detection of truncated 3' UTR transcripts of CCND1 was performed using probes to exon 3 and to two regions in the 3' UTR (see FIG. 4A and Table 5). Briefly, gene expression was normalized using the geometric mean of the 18 housekeeping genes and the log 2 of the normalized gene expression counts of the exonic probe was subtracted from that of the 3' UTR probe. Thresholds used to define biopsies with the presence of truncated 3' UTR are shown in FIG. 4B. The MCL35 scores of the cases with low and moderately low 3' UTR expression were equivalent as were the outcomes, justifying the grouping of these cases as shown in FIGS. 5A and 5B (see FIGS. 4C and 4D, respectively). There were two cases where the expression of the upstream 3' UTR probe was the same level as the exonic probe, while the downstream 3' UTR probe was low—these cases were not included in the group defined as having truncated 3' UTR.

Concordance Analysis

Figure 6A:
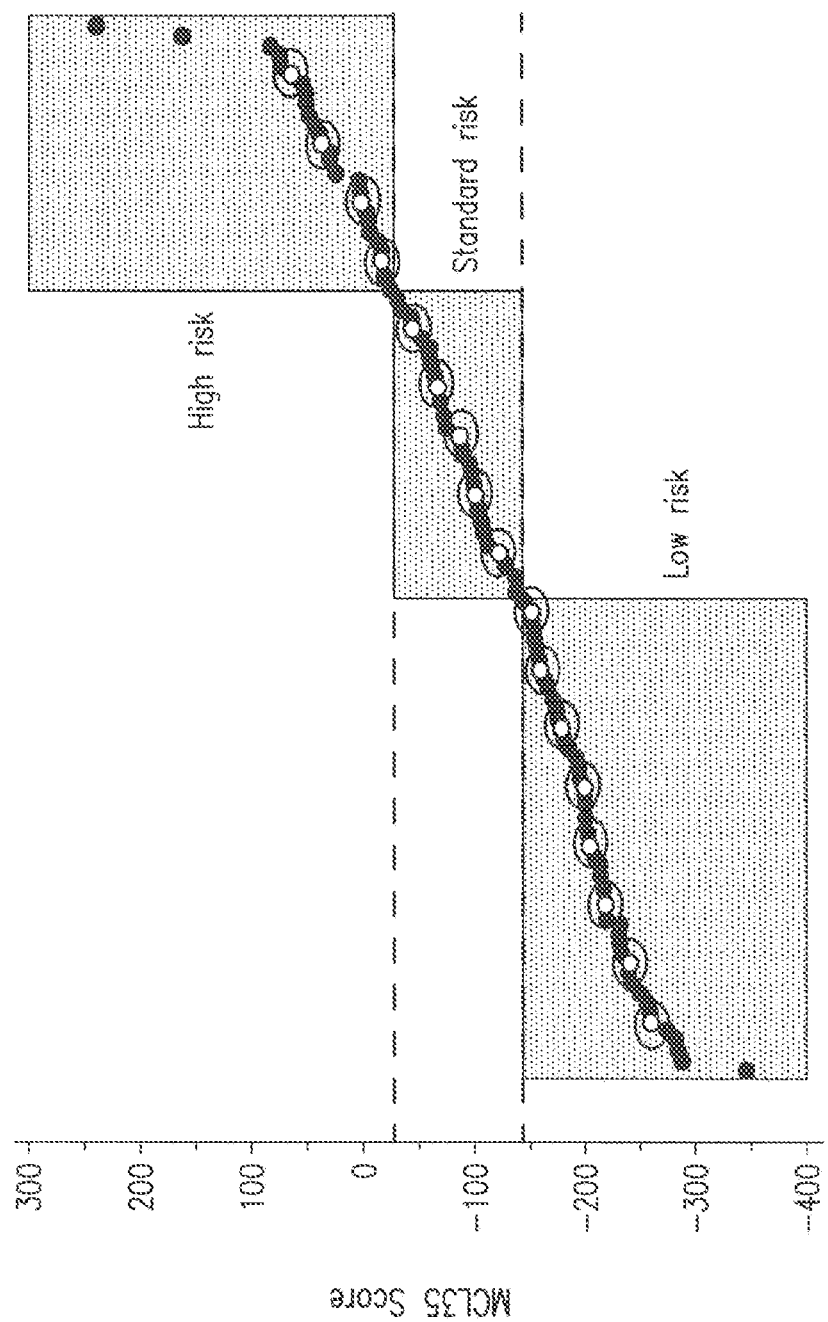
FIG. 6A shows MCL35 scores in ascending order, left to right, in the validation cohort. Circled gray dots represent the scores of the 17 biopsies (equally spread across the spectrum of scores) selected for the analytic validation studies. The other dots represent the scores of the biopsies not selected.

Technical variability (intra-laboratory variability) was assessed by calculating the average standard deviation of the MCL35 score across three replicates from 17 samples FIG. 6. One extreme outlier replicate was detected and removed from the analysis, but it was found to have negligible effect on the overall variability (see below). Inter-laboratory variability was calculated from the average variance across the laboratories for the 17 samples adjusted by the estimated technical variability. Bias was estimated by calculating the mean difference between the average Vancouver MCL35 scores, and the Barcelona and Würzburg MCL35 scores, with confidence intervals calculated based on the estimated technical and inter-laboratory variability. To model the likelihood of agreement between samples of the same patient replicated in different laboratories, it was assumed that true model scores would be distributed according to the empirical distribution of the model scores observed on the validation set. Errors were assumed to be normally distributed with variance equal to total technical plus inter-laboratory variability multiplied by two (to account for the possibility of variability in both of the hypothetical replicates). Based on this model, the likelihood that that this additional noise would cause a sample to cross the threshold from one risk group into another was calculated.

Outlier MCL35 Score

Figure 6B:
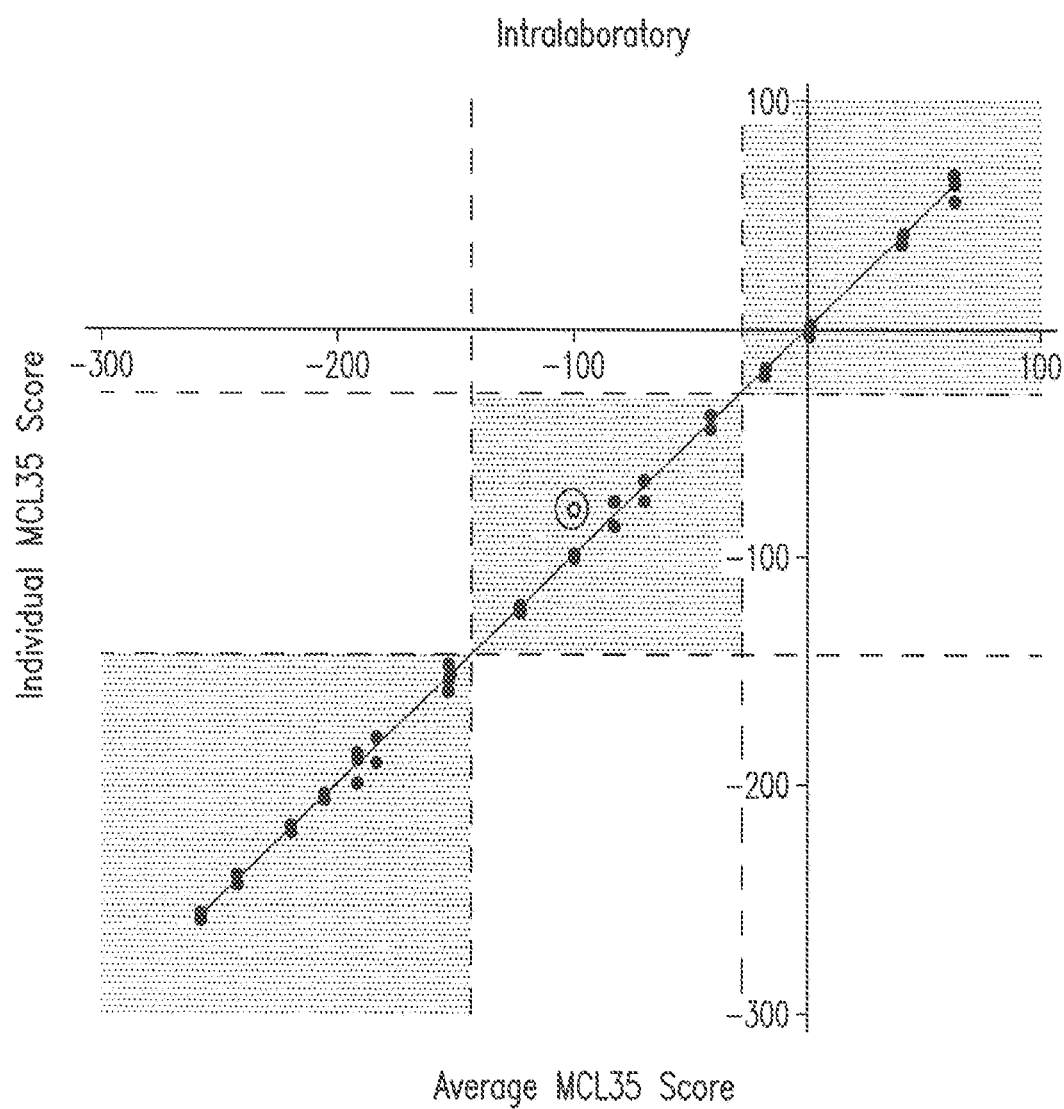
FIG. 6B shows MCL35 scores of RNA from the 17 biopsies identified in FIG. 6A run in triplicate (y-axis) plotted against the average of the three scores (x-axis). The circled dot represents an outlier score.
Figure 7:
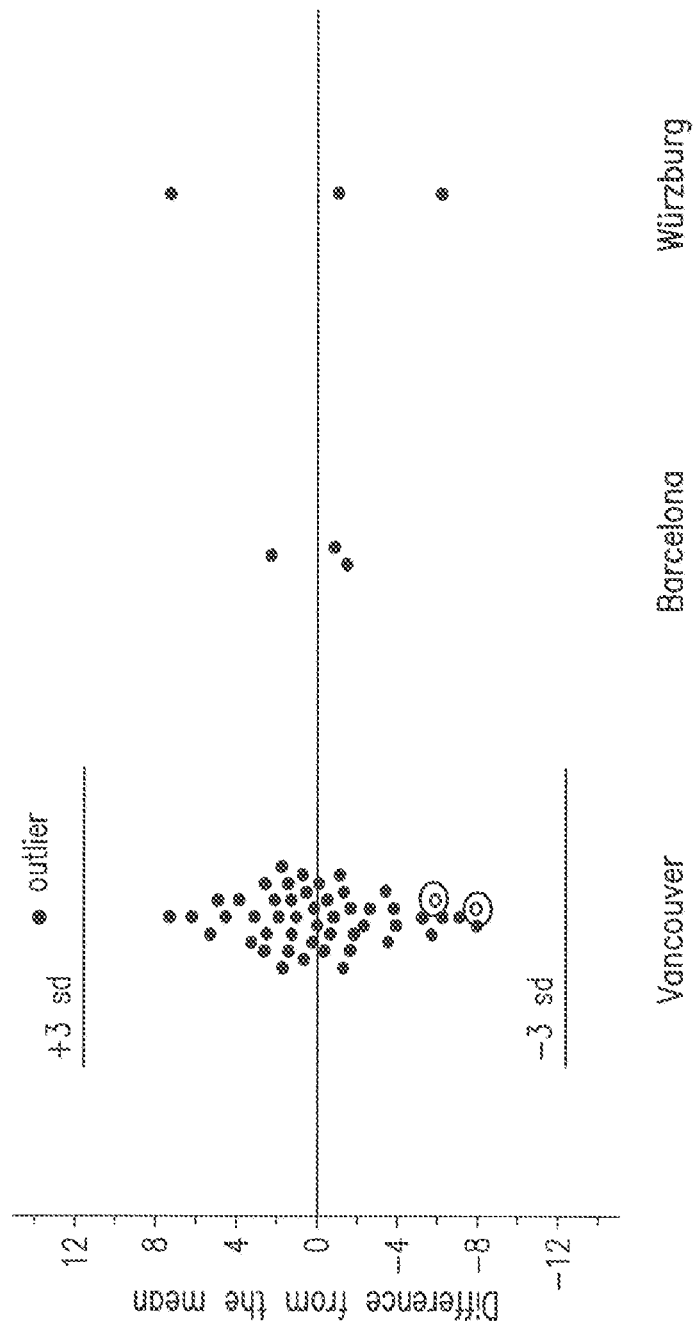
FIG. 7 is a plot that shows the difference from the mean for individual MCL35 scores within triplicates runs of RNA. At the left, the results are shown for the 17 triplicates run in Vancouver. Lines indicate the differences from the mean that represent 3 standard deviations from the mean difference. The outlier score is shown, while the other values from the triplicate containing the outlier are shown circled. In the middle and right are the differences from the mean of RNA from the same biopsy that generated the outlier score extracted and run in two independent laboratories.

A single score from one of the triplicate runs used to examine intra-laboratory variability was identified as an outlier (circled dot in FIG. 6B, see also FIG. 7). Examination of the distribution of difference from the mean of the individual replicates, showed a standard deviation of 4.06 points. This outlier was 13.8 points from the mean of that triplicate, making it an extreme outlier (P<0.001). In order to determine whether this was a property of the biopsy, independent scrolls of the biopsy were sent to the laboratories in Barcelona and Würzburg. The MCL35 scores, run in triplicate, at these laboratories showed differences from the mean that fell within expected limits, making the origin of this outlier likely to be technical rather than biological.

Assuming sample scores distributed similarly to the validation set observed, even an error the size observed for this outlying sample would result in a change in predicted class only 4.3% of the time, and so including for the possibility of low frequency (approximately 1 out of 85 trials) outliers of this magnitude will have a negligible effect on the overall estimated reproducibility of the model as a whole.

Results

Development of the MCL35 Assay

The proliferation signature was originally described using gene expression defined on the basis of RNA derived from 92 FF tissue biopsies on custom Lymphochip microarrays (Rosenwald et al., Cancer Cell, 3:185-197 (2003)). In a first step toward producing a new assay, gene expression analysis was performed on the 80 available samples from the original 92 FF RNA samples using Affymetrix® U133 plus 2.0 microarrays because these arrays provide broader coverage of the coding genome. Comparison of the correlation of expression of individual genes and the proliferation signature with the relationship between gene expression and overall survival, expressed as the Z-score from univariable Cox models, is shown in FIG. 3. The strong association observed ($r^2$=0.82) suggests that the proliferation signature encompasses much of the prognostic information present in gene expression in MCL. Furthermore, whereas the original proliferation signature solely contained genes that were over-expressed in biopsies with a high proliferation score, it is evident that a number of genes are under-expressed in these biopsies, allowing the design of a "balanced" gene expression model. Sixty-nine genes of interest, along with 30 potential housekeeping genes, were selected for further assay development, on the basis of this analysis and other published studies that have described the relationship between gene expression and outcomes m MCL (Kienle et al., J. Clin. Oncol., 25:2770-2777 (2007) and Hartmann et al., J. Clin. Oncol., 26:4966-4972 (2008), incorporated by reference herein) (see Table 6).

TABLE 6

Genes tested for selection in the MCL35 assay

| Gene symbol | Gene "Class" | Selection Criteria | MCL35 Assay |
|---|---|---|---|
| POLE2 | Proliferation | Hartmann et al | |
| RAN | Proliferation | Hartmann et al | |
| SLC29A2 | Proliferation | Hartmann et al | |
| TNFRSF10B | Proliferation | Hartmann et al | |
| ATM | Proliferation | Kienle et al | |
| CDKN1B | Proliferation | Kienle et al | |
| EZH2 | Proliferation | Kienle et al | |
| MDM2 | Proliferation | Kienle et al | |
| RB1 | Proliferation | Kienle et al | |
| ANLN | Proliferation | Rosenwald et al | |
| ARMCX4 | Proliferation | Rosenwald et al | |
| ASPM | Proliferation | Rosenwald et al | |
| ATL1 | Anti-Proliferation | Rosenwald et al | YES |
| BIRC5 | Proliferation | Rosenwald et al | |
| BTN2A1 | Proliferation | Rosenwald et al | |
| BUB1 | Proliferation | Rosenwald et al | |
| BUB1B | Proliferation | Rosenwald et al | |
| CCNA2 | Proliferation | Rosenwald et al | |
| CCNB1 | Proliferation | Rosenwald et al | |
| CCNB2 | Proliferation | Rosenwald et al | YES |
| CDC2 | Proliferation | Rosenwald et al | |
| CDC20 | Proliferation | Rosenwald et al | YES |
| CDCA3 | Proliferation | Rosenwald et al | |
| CDCA5 | Proliferation | Rosenwald et al | |
| CDCA8 | Proliferation | Rosenwald et al | |
| CDKN3 | Proliferation | Rosenwald et al | YES |
| CENPA | Proliferation | Rosenwald et al | |
| CENPE | Proliferation | Rosenwald et al | |
| CENPF | Proliferation | Rosenwald et al | |
| CEP55 | Proliferation | Rosenwald et al | |
| CTPS | Proliferation | Rosenwald et at | |
| DLGAP5 | Proliferation | Rosenwald et al | |
| E2F2 | Proliferation | Rosenwald et al | YES |
| ESPL1 | Proliferation | Rosenwald et al | YES |
| EXO1 | Proliferation | Rosenwald et al | |
| FAM83D | Proliferation | Rosenwald et al | YES |
| FMNL3 | Anti-Proliferation | Rosenwald et al | YES |
| FOXM1 | Proliferation | Rosenwald et al | YES |
| GLIPR1 | Anti-Proliferation | Rosenwald et al | YES |
| GRAMD3 | Proliferation | Rosenwald et al | |
| GTSE1 | Proliferation | Rosenwald et al | |
| H2AFX | Proliferation | Rosenwald et al | YES |
| HBP1 | Proliferation | Rosenwald et al | |
| HJURP | Proliferation | Rosenwald et al | |
| KIF11 | Proliferation | Rosenwald et al | |
| KIF14 | Proliferation | Rosenwald et al | |
| KIP15 | Proliferation | Rosenwald et al | |
| KIF18B | Proliferation | Rosenwald et al | |
| KIF23 | Proliferation | Rosenwald et al | |
| KIF2C | Proliferation | Rosenwald et al | YES |
| KIF4A | Proliferation | Rosenwald et al | |
| LAPTM4A | Proliferation | Rosenwald et al | |
| MCM10 | Proliferation | Rosenwald et al | |
| MKI67 | Proliferation | Rosenwald et al | YES |
| NCAPG | Proliferation | Rosenwald et al | YES |
| NCAPH | Proliferation | Rosenwald et al | |
| NUSAP1 | Proliferation | Rosenwald et al | |
| SGOL2 | Proliferation | Rosenwald et al | |
| SPAG5 | Proliferation | Rosenwald et al | |
| TK1 | Proliferation | Rosenwald et al | |
| TOP2A | Proliferation | Rosenwald et al | YES |
| TPX2 | Proliferation | Rosenwald et al | |
| TRIP13 | Proliferation | Rosenwald et al | |
| TUBG1 | Proliferation | Rosenwald et al | |
| TYMS | Proliferation | Rosenwald et al | |
| WHSC1 | Proliferation | Rosenwald et al | |
| YPEL5 | Proliferation | Rosenwald et al | |
| ZDHHC21 | Anti-Proliferation | Rosenwald et al | YES |
| ZWINT | Proliferation | Rosenwald et al | YES |
| AKAP9 | Housekeeping | Rosenwald et al | |
| CDK5RAP2 | Housekeeping | Rosenwald et al | |
| CHD4 | Housekeeping | Rosenwald et al | YES |
| DNAJB12 | Housekeeping | Rosenwald et al | |
| ERBB2IP | Housekeeping | Rosenwald et al | YES |
| GIT2 | Housekeeping | Rosenwald et al | YES |

TABLE 6-continued

Genes tested for selection in the MCL35 assay

| Gene symbol | Gene "Class" | Selection Criteria | MCL35 Assay |
|---|---|---|---|
| GSK3B | Housekeeping | Rosenwald et al | YES |
| HARBI1 | Housekeeping | Rosenwald et al | |
| HSPA9 | Housekeeping | Rosenwald et al | YES |
| IK | Housekeeping | Rosenwald et al | YES |
| ISY1 | Housekeeping | Rosenwald et al | |
| MLL2 | Housekeeping | Rosenwald et al | YES |
| MLLT10 | Housekeeping | Rosenwald et al | |
| NEU3 | Housekeeping | Rosenwald et al | YES |
| OPA1 | Housekeeping | Rosenwald et al | |
| PHF23 | Housekeeping | Rosenwald et al | |
| R3HDM1 | Housekeeping | Rosenwald et al | YES |
| RANBP9 | Housekeeping | Rosenwald et al | YES |
| RC3H2 | Housekeeping | Rosenwald et al | YES |
| RNF214 | Housekeeping | Rosenwald et al | |
| THOC5 | Housekeeping | Rosenwald et al | |
| TRIM56 | Housekeeping | Rosenwald et al | YES |
| TRIM62 | Housekeeping | Rosenwald et al | |
| UBXN4 | Housekeeping | Rosenwald et al | YES |
| VAC14 | Housekeeping | Rosenwald et al | YES |
| VRK3 | Housekeeping | Rosenwald et al | YES |
| WAC | Housekeeping | Rosenwald et al | YES |
| WDR55 | Housekeeping | Rosenwald et al | YES |
| ZCCHC2 | Housekeeping | Rosenwald et al | |
| ZNF598 | Housekeeping | Rosenwald et al | YES |

The selection criteria column indicates the source for the decision to include the gene. These include two manuscripts (Kienle et al., J. Clin. Oncol., 25:2770-2777 (2007) and Hartmann et al., J. Clin. Oncol., 26:4966-4972 (2008)) and the re-analysis of 80 biopsies from (Rosenwald et al., Cancer Cell, 3:185-197 (2003)) as described above and shown in FIG. 3.

Genes that were part of the analysis but were not used as part of the refined gene list in Table 1, but which may subtly influence the set due to their absence or presence, are shown in Table 7 below.

TABLE 7

| Human Gene | GenBank Accession | Position | Target DNA (SEQ ID No.) | Capture Probe (SEQ ID NO:) | Reporter Probe (SEQ ID NO:) |
|---|---|---|---|---|---|
| BTLA | NM_181780.2 | 306-405 | 36 | 91 | 146 |
| CCND1 | NM_053056.2 | 691-790 | 37 | 92 | 147 |
| CCND1_2 | NM_053056.2 | 3760-3859 | 38 | 93 | 148 |
| CCND1_8 | NM_053056.2 | 2726-2825 | 39 | 94 | 149 |
| CD200 | NM_005944.5 | 666-765 | 40 | 95 | 150 |
| CNN3 | NM_001839.4 | 1133-1232 | 41 | 96 | 151 |
| CNR1 | NM_016083.3 | 3001-3100 | 42 | 97 | 152 |
| DBN1 | NM_004395.3 | 999-1098 | 43 | 98 | 153 |
| DCHS1 | NM_003737.2 | 7261-7360 | 44 | 99 | 154 |
| FARP1 | NM_005766.2 | 4374-4473 | 45 | 100 | 155 |
| FHL1 | NM_001449.4 | 1033-1132 | 46 | 101 | 156 |
| FNBP1L | NM_001024948.1 | 1156-1255 | 47 | 102 | 157 |
| HDGFRP3 | NM_016073.3 | 1897-1996 | 48 | 103 | 158 |
| MYC | NM_002467.3 | 1611-1710 | 49 | 104 | 159 |
| NINL | NM_025176.4 | 3347-3446 | 50 | 105 | 160 |
| NREP | NM_001142474.1 | 991-1090 | 51 | 106 | 161 |
| PLXNB1 | NM_001130082.1 | 6036-6135 | 52 | 107 | 162 |
| PON2 | NM_000305.2 | 943-1042 | 53 | 108 | 163 |
| SLAMF1 | NM_003037.2 | 581-680 | 54 | 109 | 164 |
| SOX11 | NM_003108.3 | 5651-5750 | 55 | 110 | 165 |

Digital gene expression was performed to quantitate these 99 genes in RNA extracted from 47 FFPE biopsies, including all 39 suitable biopsies with matched Affymetrix® gene expression data on RNA from FF biopsies. Seventeen genes were selected to replicate the proliferation signature based on the following criteria: being highly correlated across the NanoString® (FFPE) and Affymetrix® (FF) platforms, being moderately- to highly-expressed on the NanoString® platform, and having high variance across the samples. Eighteen housekeeping genes were also selected on the basis of having low variance across the samples and moderate to high expression levels. Digital gene expression was then performed on the same 47 FFPE RNA samples using a smaller code set containing these 35 genes.

Figure 8:
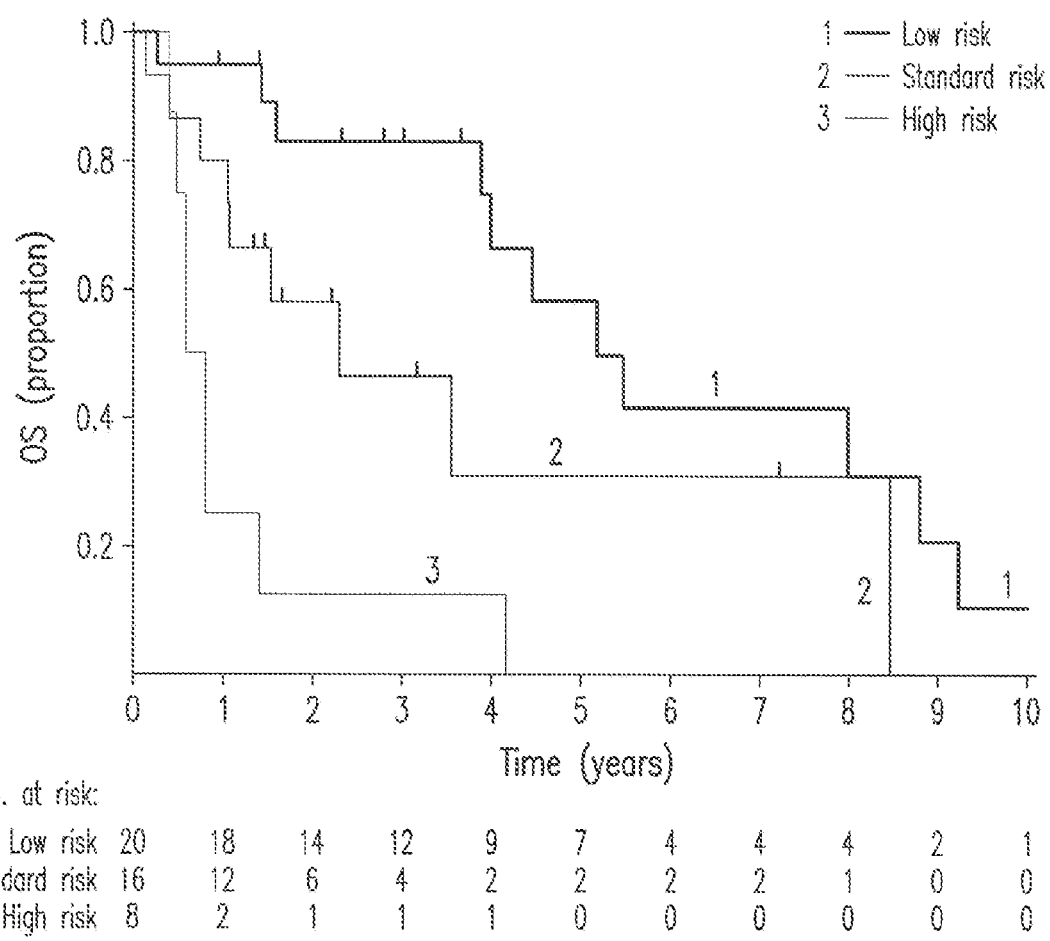
FIG. 8 shows Kaplan-Meier curves of the overall survival (OS) of the three patient groups identified by the MCL35 assay. Outcome data were available for 44 of the 47 patients.

After normalization with the 18 housekeeping genes, a model was developed using expression of the 17 proliferation genes to replicate the proliferation signature score described by Rosenwald et al., Cancer Cell, 3:185-197 (2003). Optimal thresholds for defining three groups with distinct outcomes (i.e., OS) were determined using Affymetrix® data from 123 FF biopsies, including the 80 biopsies from Rosenwald et al., Cancer Cell, 3:185-197 (2003) (FIG. 8). The final model, named the MCL35 assay, including the gene coefficients and thresholds, was then locked and validated in an independent cohort of patients.

MCL35 assay is prognostic in patients treated with R-CHOP

The MCL35 assay was then applied to pre-treatment FFPE lymph node biopsies from 110 patients treated with R-CHOP with or without ASCT at the BCCA (Table 2, FIG. 2). Adequate gene expression was obtained in 108 (98%) of the biopsies. As a continuous variable, the MCL35 score was significantly associated with OS (univariate P<0.001, Harrell's C-index 0.74 (95% CI, 0.66-0.82)). The assay assigned 28 (26%) patients to the high-risk group, 31 (29%) to the standard-risk group, and 49 (45%) to the low-risk group. The outcomes were significantly different among these three groups, with median OS of 1.1, 2.6, and 8.6 years in the high-, standard- and low-risk groups, respectively (log-rank for trend P<0.001, FIG. 5A).

Recognized high-risk MCL features were more frequently encountered in the high-risk group, including morphological characteristics (pleomorphic and blastoid variants), TP53 positivity by IHC, and the presence of CCND1 mRNA with truncated 3' UTRs (Table 2). In a planned subgroup analysis, the assay also defined groups with significantly different OS in patients aged 65 years or under for whom there was intention-to-treat with R-CHOP followed by a consolidative ASCT. In this group the median OS was 1.4 years, 5.9 years, and not reached in the high-, standard- and low-risk groups, respectively (log rank for trend P<0.001, FIG. 5B). The MIPI also identified groups of patients with significantly different OS in the total validation cohort (log rank for trend P<0.001, Harrell's C-index 0.74 (95% CI, 0.66-0.82)). In multivariable analyses, both the MCL35 and the MIPI independently contributed to OS (P<0.001 for both variables) whether the variables were continuous or grouped. See Table 8.

TABLE 8

Multivariate Analyses of the MIPI and the MCL35 on the validation

| | | Overall Survival | | |
|---|---|---|---|---|
| Variable | | HR | 95% CI | P* |
| Multivariate: | | | | |
| MCL35 | per Single level shift High v Standard v Low | 2.0 | 1.4-2.8 | <.001 |
| MIPI | per Single level shift High v Intermediate v Low | 2.4 | 1.7-3.5 | <.001 |

TABLE 8-continued

Multivariate Analyses of the MIPI and the MCL35 on the validation

| | | Overall Survival | | |
|---|---|---|---|---|
| Variable | | HR | 95% CI | P* |
| Multivariate: | | | | |
| MCL35 | continuous variable per 100 units (scores range from −346 to +240) | 1.6 | 1.2-2.1 | <.001 |
| MIPI | continuous variable per unit (score range from 4.87 to 8.17) | 2.8 | 1.8-4.1 | <.001 |

*One-sided score test

Figure 9A:
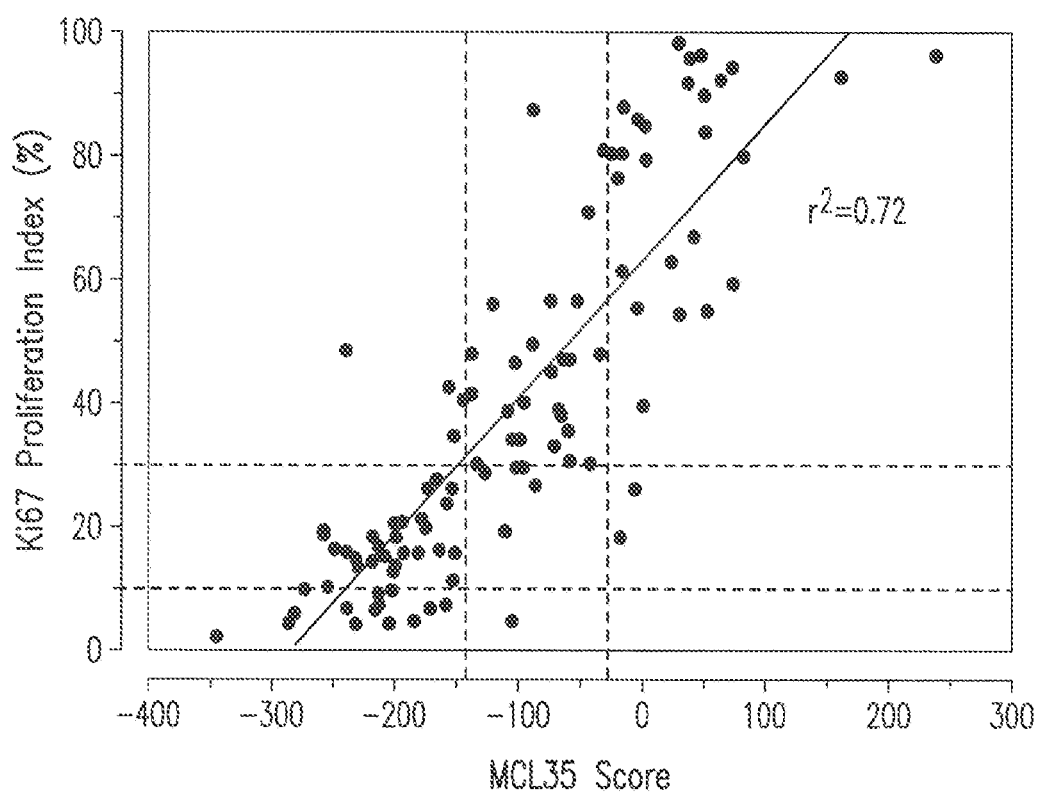
FIG. 9A shows a plot of the Ki67 Proliferation Index (MIB-1) against the MCL35 score. The horizontal lines are placed at 10% and 30%, while the vertical lines are at the thresholds that separate low-risk (left section) from standard-risk (middle section) and high-risk (right section).
Figure 9B:
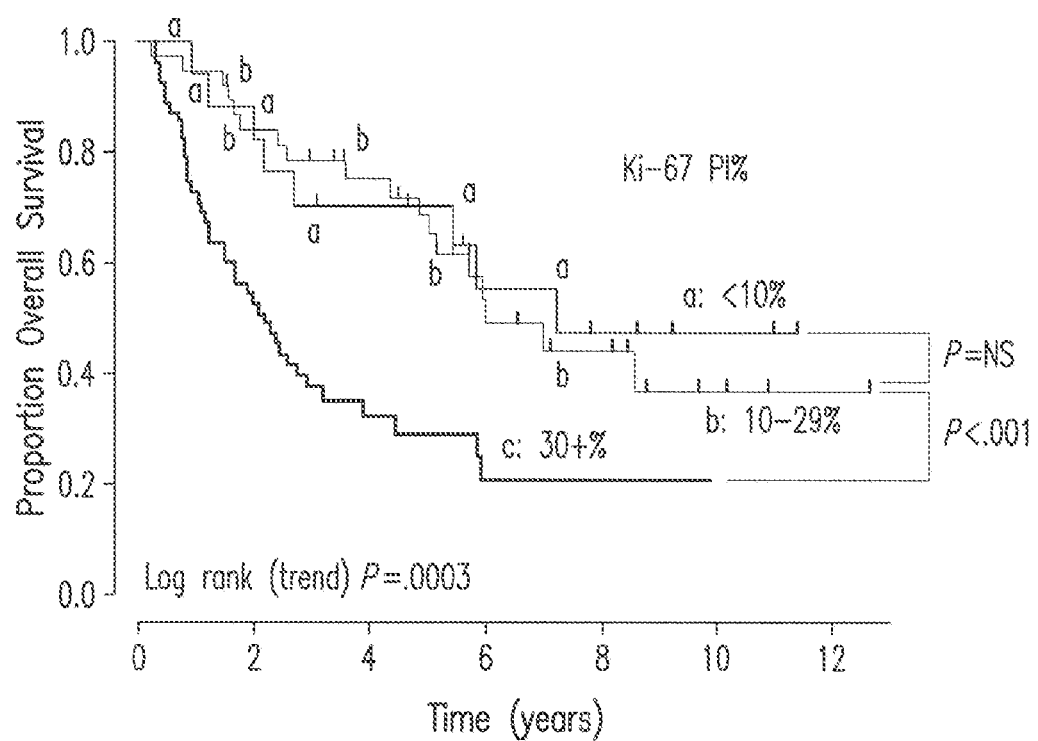
FIG. 9B shows a Kaplan-Meier curve of overall survival in groups defined using the Ki67 proliferation index (PI).

There was a significant positive correlation between the Ki-67 PI and the MCL35 score ($r^2$=0.72). As a continuous variable, the Ki-67 PI was significantly associated with OS (univariable P<0.001; Harrell's C-index, 0.69 [95% CI, 0.61 to 0.77]). Applying previously published thresholds (Determann et al., Blood, 111:2385-2387 (2008), incorporated by reference herein), 55 (50%) of the biopsies had a Ki-67 PI≥30%, 38 (35%) had a Ki-67 PT of 10% to 29%, and 17 (15%) had a Ki-67 PI<10%. A Ki-67 PI≥30% was associated with inferior OS (median, 2.2 years; log-rank v Ki-67 PI 10% to 29%, P<0.001), whereas the lengths of OS when the Ki-67 PI was 10% to 29% and <10% were not significantly different from one another (median, 6 and 7.2 years, respectively; log-rank P=0.75). In multivariable Cox models, the Ki-67 PT (P=0.36) did not contribute prognostically when adjusted for the MCL35 assay results, whereas the MCL35 did contribute (P<0.001) when adjusted for the Ki-67 PI, whether the variables were continuous or grouped (Ki-67 PI groups: 0% to 29% and ≥30%). See Table 9 and FIGS. 9A and 9B.

TABLE 9

Multivariate Analyses of the Ki67 and MCL35 on the validation cohort

| | | Overall Survival | | |
|---|---|---|---|---|
| Variable | | HR | 95% CI | P* |
| Multivariate: | | | | |
| MCL35 | per Single level shift High v Standard v Low | 2.0 | 1.4-3.0 | <.001 |
| Ki67 | Ki67 < 30% vs Ki67 >= 30% | 1.3 | .67-2.7 | .36 |
| Multivariate: | | | | |
| MCL35 | Continuous variable per 100 units (scores range from −346 to +240) | 2.1 | 1.4-3.2 | <.001 |
| Ki67 | Continuous variable per 10% (percentages range from 2% to 98%) | .97 | .84-1.1 | .56 |

*One-sided score test

Analytic Validity of the MCL35 Assay

Experiments were then performed to determine the intra- and inter-laboratory reproducibility of the MCL35 assay. Seventeen biopsies were selected on the basis that the MCL35 scores were equally distributed across the population (FIG. 6A) and thus representative of the distribution of MCL35 scores in the validation cohort. For intra-laboratory comparison, the RNA from each of these biopsies was run on the MCL35 assay in triplicate, with each run performed on a different aliquot of RNA and on different NanoString® cartridges. The results showed 100% concordance of risk group assignment (FIG. 6B) across the triplicates. One outlier result was observed, where the gene expression was disparate from the other replicates. This outlier result was removed from further analyses. The standard deviation of the intra-laboratory error was 4 points, compared with a range of scores across the validation cohort of 586 points. For inter-laboratory comparison, scrolls of tissue from the 17 biopsies were distributed to two independent laboratories in Barcelona, Spain and Würzburg, Germany, where RNA was extracted and run on the MCL35 assay. There was 100% concordance of risk group assignment and no significant bias was seen compared with the mean of the triplicate results from the laboratory in Vancouver, BC, Canada (95% confidence intervals (CIs) of bias: Barcelona −6.1 to 0.6; Würzburg −3.7 to 3.0 points). The standard deviation of the inter-laboratory error was 3 points giving a standard deviation of the total (intra-plus inter-laboratory) error of 5 points. Given that the examination of a small number of samples provides an imprecise estimate of concordance over a population, the distribution of the MCL35 score in this study and the calculated distributions of error were used to estimate concordance of risk group assignment between laboratories over a large population (see above). This model estimated that 1.2% of biopsies would change risk group assignment between laboratories. The supplement contains these analyses if the outlier result was retained.

Figure 10A:
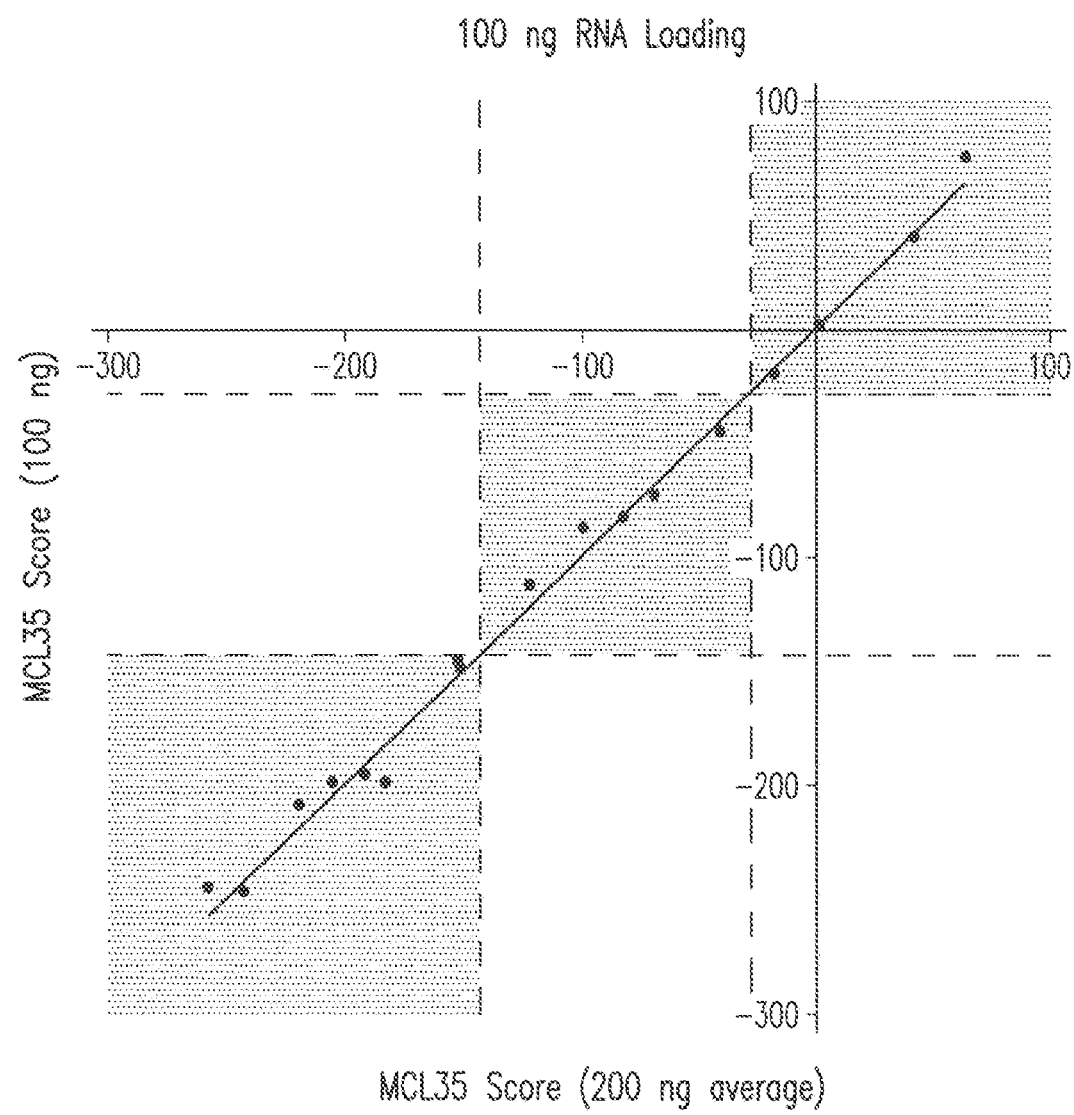
FIG. 10A shows MCL35 scores from 100 ng of RNA from the 17 biopsies (y-axis) plotted against the score when 200 ng was loaded. The solid line represents the line-of-best-fit.
Figure 10B:
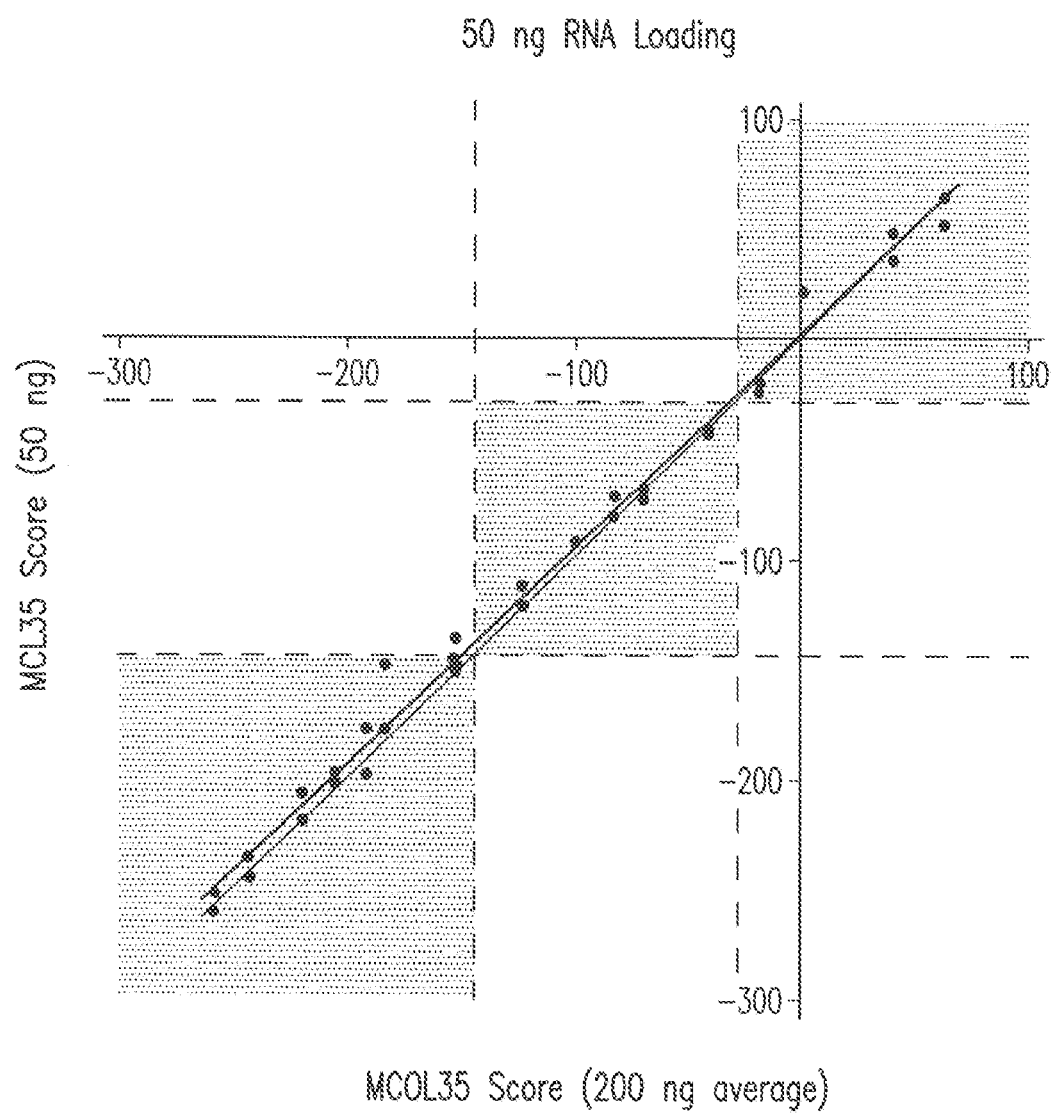
FIG. 10B shows MCL35 scores from 50 ng of RNA run in duplicate from the 17 biopsies (y-axis) plotted against the score when 200 ng was loaded. The thick solid line represents the line-of-best-fit; the thin solid line represents a line on the 45 degree angle.
Figure 10C:
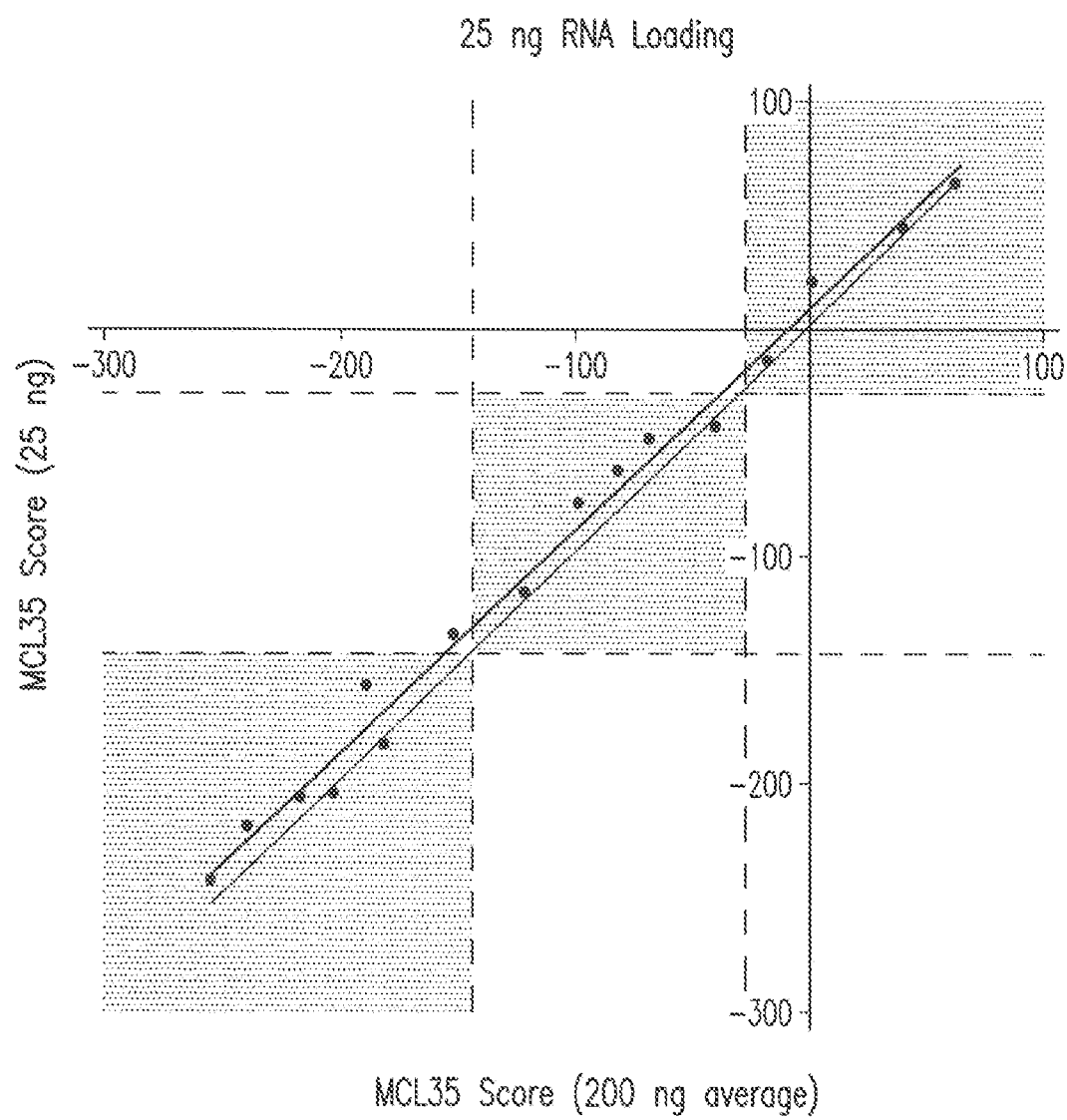
FIG. 10C shows MCL35 scores from 25 ng of RNA from the 17 biopsies (y-axis) plotted against the score when 200 ng was loaded. The thick solid line represents the line-of-best-fit; the thin solid line represents a line on the 45 degree angle.

In order to determine the lower limit of RNA input for the MCL35 assay, RNA from the same 17 biopsies was run on the assay with input of 100 ng, 50 ng (in duplicate) and 25 ng (FIGS. 10A-10C). No significant bias was observed at 100 and 50 ng compared to mean of the triplicates at 200 ng. However, at 25 ng there was a consistent trend towards higher MCL35 scores.

Discussion

The clinical validity of the MCL35 assay, identifying patient groups at significantly different risk of death, was demonstrated in an independent cohort of uniformly treated patients. The assay was demonstrated to be a powerful prognostic biomarker in patients treated with R-CHOP, identifying sizeable groups of patients with dismal or excellent outcomes. Furthermore, the prognostic power of the assay was maintained in younger patients for whom there was a plan to consolidate with an ASCT.

Similar to the original proliferation signature, the assay summates established high-risk disease features, including blastoid and pleomorphic morphology, TP53 overexpression, and truncation of the 3'UTR of CCND1 mRNA transcripts. In addition, the prognostic power of the assay was independent of the MIPI.

This study was restricted to lymph node biopsies with a tumor content of ≥60%, which encompasses the vast majority of patients with conventional MCL. Further studies are required to establish the clinical validity of the assay in biopsies that have low tumor content or are from extranodal sites. Similarly, this study exclusively used biopsies fixed in formalin, which is the methodology used by the vast majority of clinical laboratories. Further study would be required to determine whether the performance of the assay is affected by alternative fixation methodologies. Proliferation of MCL cells in peripheral blood is typically, but not universally, lower than in matched lymph node infiltrates; this effect is thought to reflect activation of the NF-κB pathway in the malignant cells by the tumor microenvironment, which dissipates upon exit from the lymph node. This inconsistent relationship of proliferation between different tumor compartments might require alteration of the assay parameters and may affect the clinical validity of the MCL35 assay in peripheral blood samples. Similarly, it is also not known whether the assay will have clinical validity in the rare leukemic non-nodal subtype of the disease.

The analytic validity of the assay was demonstrated by examining both intra- and inter-laboratory variability, showing a very low estimated 1.2% rate of discordance across laboratories. This reproducibility sharply contrasts with the published literature regarding the Ki67 PI as a surrogate marker for the proliferation signature, which has high inter-laboratory and inter-observer variability in lymphoma. This study was not designed or powered to directly compare the clinical validity of the new assay with this surrogate marker, but the MCL35 assay subsumed the prognostic power of the Ki67 PI in pairwise multivariate analyses. Finally, the demonstration that there is no appreciable bias with RNA loading down to 50 ng will allow the assay to be applied to the majority of tissue biopsies, including core needle biopsies.

Clinical utility, as defined by improving patient outcomes, relies on the ability of the biomarker to guide clinical management. It is appreciated that the design of this study does not establish the assay as a predictive biomarker because it was tested in a homogeneously treated population. To establish the MCL35 assay as a predictive biomarker, it will need to be applied to prospectively collected samples from clinical trials testing the efficacy of modern treatment regimens. The recognition of highly variable treatment outcomes in this disease, along with the increasing range of efficacious treatment options, makes risk-stratified approaches attractive whereby toxic and/or expensive therapies are provided to patients in whom the most benefit will be accrued.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Also, everywhere "comprising" (or its equivalent) is recited, the "comprising" is considered to incorporate "consisting essentially of" and "consisting of" Thus, an embodiment "comprising" (an) element(s) supports embodiments "consisting essentially of" and "consisting of" the recited element(s). Everywhere "consisting essentially of" is recited is considered to incorporate "consisting of" Thus, an embodiment "consisting essentially of" (an) element(s) supports embodiments "consisting of" the recited element(s). Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of determining a survival predictor score of a human subject having mantle cell lymphoma (MCL), which method comprises:

(a) providing a formalin-fixed and paraffin-embedded (FFPE) biopsy sample from the subject;

(b) isolating RNA gene expression product from the biopsy sample;

(c) obtaining gene expression data from the RNA gene expression product, wherein the gene expression data comprises signal values that represent expression levels for each gene of the table below:

| Human Gene | Anti-Proliferation/ Housekeeper/ Proliferation Gene | Coeff. Value | Gen-Bank Accession | Position | Target DNA (SEQ ID NO:) | Capture Probe (SEQ ID NO:) | Reporter Probe (SEQ ID NO:) |
|---|---|---|---|---|---|---|---|
| ATL1 | Anti-Proliferation | −19.64 | NM_015915.4 | 1141-1240 | 1 | 56 | 111 |
| FMNL3 | Anti-Proliferation | −21.46 | NM_175736.4 | 2434-2533 | 2 | 57 | 112 |
| GLIPR1 | Anti-Proliferation | −29.91 | NM_006851.2 | 256-355 | 3 | 58 | 113 |
| ZDHHC21 | Anti-Proliferation | −23.47 | NM_178566.4 | 713-812 | 4 | 59 | 114 |
| CHD4 | Housekeeper | 0.75 | NM_001273.2 | 2681-2780 | 5 | 60 | 115 |
| ERBB2IP | Housekeeper | 0.75 | NM_018695.2 | 3676-3775 | 6 | 61 | 116 |
| GIT2 | Housekeeper | 0.75 | NM_057169.2 | 606-705 | 7 | 62 | 117 |
| GSK3B | Housekeeper | 0.75 | NM_002093.2 | 926-1025 | 8 | 63 | 118 |
| HSPA9 | Housekeeper | 0.75 | NM_004134.4 | 976-1075 | 9 | 64 | 119 |

-continued

| Human Gene | Anti-Proliferation/ Housekeeper/ Proliferation Gene | Coeff. Value | GenBank Accession | Target DNA Position | Target DNA Probe (SEQ ID NO:) | Capture Probe (SEQ ID NO:) | Reporter Probe (SEQ ID NO:) |
|---|---|---|---|---|---|---|---|
| IK | Housekeeper | 0.75 | NM_006083.3 | 557-656 | 10 | 65 | 120 |
| MLL2 | Housekeeper | 0.75 | NM_003482.3 | 6071-6170 | 11 | 66 | 121 |
| NEU3 | Housekeeper | 0.75 | NM_006656.5 | 1841-1940 | 12 | 67 | 122 |
| R3HDM1 | Housekeeper | 0.75 | NM_015361.2 | 1276-1375 | 13 | 68 | 123 |
| RANBP9 | Housekeeper | 0.75 | NM_005493.2 | 2001-2100 | 14 | 69 | 124 |
| RC3H2 | Housekeeper | 0.75 | NM_018835.2 | 2911-3010 | 15 | 70 | 125 |
| TRIM56 | Housekeeper | 0.75 | NM_030961.1 | 2571-2670 | 16 | 71 | 126 |
| UBXN4 | Housekeeper | 0.75 | NM_014607.3 | 344-443 | 17 | 72 | 127 |
| VAC14 | Housekeeper | 0.75 | NM_018052.3 | 1476-1575 | 18 | 73 | 128 |
| VRK3 | Housekeeper | 0.75 | NM_016440.3 | 821-920 | 19 | 74 | 129 |
| WAC | Housekeeper | 0.75 | NM_100486.2 | 756-855 | 20 | 75 | 130 |
| WDR55 | Housekeeper | 0.75 | NM_017706.4 | 816-915 | 21 | 76 | 131 |
| ZNF598 | Housekeeper | 0.75 | NM_178167.2 | 2369-2468 | 22 | 77 | 132 |
| CCNB2 | Proliferation | 6.01 | NM_004701.2 | 981-1080 | 23 | 78 | 133 |
| CDC20 | Proliferation | 6.35 | NM_001255.2 | 431-530 | 24 | 79 | 134 |
| CDKN3 | Proliferation | 6.4 | NM_005192.3 | 511-610 | 25 | 80 | 135 |
| E2F2 | Proliferation | 6.02 | NM_004091.2 | 3606-3705 | 26 | 81 | 136 |
| ESPL1 | Proliferation | 6.5 | NM_012291.4 | 1286-1385 | 27 | 82 | 137 |
| FAM83D | Proliferation | 5.92 | NM_030919.2 | 866-965 | 28 | 83 | 138 |
| FOXM1 | Proliferation | 6.55 | NM_021953.2 | 3209-3308 | 29 | 84 | 139 |
| H2AFX | Proliferation | 6.08 | NM_002105.2 | 1393-1492 | 30 | 85 | 140 |
| KIF2C | Proliferation | 6.19 | NM_006845.3 | 1941-2040 | 31 | 86 | 141 |
| MKI67 | Proliferation | 6.65 | NM_002417.2 | 4021-4120 | 32 | 87 | 142 |
| NCAPG | Proliferation | 6.44 | NM_022346.3 | 781-880 | 33 | 88 | 143 |
| TOP2A | Proliferation | 6.46 | NM_001067.2 | 5377-5476 | 34 | 89 | 144 |
| ZWINT | Proliferation | 5.41 | NM_007057.3 | 851-950 | 35 | 90 | 145; | and
(d) determining a survival predictor score from the gene expression data, wherein the survival predictor score is determined by:
(1) log transforming each signal value of each gene obtained in (c) to obtain a log transformed value for each gene,
(2) multiplying the log transformed value of each gene obtained in (d)(1) by the corresponding coefficient value for the respective gene listed in the table in (c) to obtain a multiplication product for each gene, and
(3) summing the multiplication products of each gene obtained in (d)(2).

2. The method of claim 1, wherein the survival predictor score is determined by the equation:

$$y = \sum_i c_i \cdot \log_2(x_i)$$

wherein y is the survival predictor score, the summation of over the set of genes listed in the table in (c) with each gene in the set being represented by i, $c_i$ is the corresponding coefficient value for the respective gene i in the table in (c), and $x_i$ is the signal value for gene i.

3. The method of claim 1, wherein the RNA gene expression data is obtained using an assay comprising color-coded probes.

4. A method of predicting the survival outcome of a human subject having mantle cell lymphoma (MCL) comprising:
(a) determining the survival predictor score of the subject according to claim 1; and
(b) classifying the subject as belonging to one of the following groups based on the survival predictor score: (i) good prognosis, (ii) intermediate prognosis, and (iii) poor prognosis.

5. A method of selecting a treatment for a human subject having mantle cell lymphoma (MCL) comprising:
(a) predicting a survival outcome of the human subject having MCL according to claim 4; and
(b) selecting a treatment for the subject based on the subject's classification.

6. The method of claim 5, wherein the subject is classified as belonging to the group of (i) good prognosis wherein the survival predictor score is determined as less than −143.

7. The method of claim 5, wherein the subject is classified as belonging to the group of (iii) poor prognosis wherein the survival predictor score is determined as greater than −28.

8. The method of claim 5, wherein the treatment includes administration of R-CHOP (rituximab, cyclophosphamide, hydroxydaunorubicin, vincristine, and prednisone).

9. A method of treating a human subject having mantle cell lymphoma (MCL) comprising:
(a) selecting a treatment for the human subject having MCL according to claim 6; and
(b) treating the subject with (i) cyclophosphamide, hydroxydaunorubicin, vincristine, and prednisone, (ii) rituximab, (iii) BTK inhibitors, (iv) IMiDs, (v) mTor inhibitors, (vi) bendamustine, or (vii) any combination of (i)-(vi).

10. A method of predicting the survival outcome of a human subject having mantle cell lymphoma (MCL) comprising:
(a) determining the survival predictor score of the subject according to claim 1; and
(b) classifying the subject as belonging to one of the following groups based on the survival predictor score: (i) good prognosis wherein y is determined as less than −143, (ii) intermediate prognosis wherein the survival predictor score is determined as between −143 and −28, and (iii) poor prognosis wherein the survival predictor score is determined as greater than −28.

11. A method of determining a survival predictor score of a human subject having mantle cell lymphoma (MCL), which method comprises:
(a) providing a formalin-fixed and paraffin-embedded (FFPE) biopsy sample from the subject;
(b) isolating RNA gene expression product from the biopsy sample;
(c) obtaining gene expression data from the RNA gene expression product, wherein the gene expression data comprises signal values that represent expression levels for each gene of the table below:

| Human Gene | Anti-Proliferation/ House keeper/ Proliferation Gene | Coeff. Value | GenBank Accession | Position | Target DNA (SEQ ID NO:) | Capture Probe (SEQ ID NO:) | Reporter Probe (SEQ ID NO:) |
|---|---|---|---|---|---|---|---|
| ATL1 | Anti-Proliferation | −19.64 | NM_015915.4 | 1141-1240 | 1 | 56 | 111 |
| FMNL3 | Anti-Proliferation | −21.46 | NM_175736.4 | 2434-2533 | 2 | 57 | 112 |
| GLIPR1 | Anti-Proliferation | −29.91 | NM_006851.2 | 256-355 | 3 | 58 | 113 |
| ZDHHC21 | Anti-Proliferation | −23.47 | NM_178566.4 | 713-812 | 4 | 59 | 114 |
| CHD4 | House keeper | 0.75 | NM_001273.2 | 2681-2780 | 5 | 60 | 115 |
| ERBB2IP | House keeper | 0.75 | NM_018695.2 | 3676-3775 | 6 | 61 | 116 |
| GIT2 | House keeper | 0.75 | NM_057169.2 | 606-705 | 7 | 62 | 117 |
| GSK3B | House keeper | 0.75 | NM_002093.2 | 926-1025 | 8 | 63 | 118 |
| HSPA9 | House keeper | 0.75 | NM_004134.4 | 976-1075 | 9 | 64 | 119 |
| IK | House keeper | 0.75 | NM_006083.3 | 557-656 | 10 | 65 | 120 |
| MLL2 | House keeper | 0.75 | NM_003482.3 | 6071-6170 | 11 | 66 | 121 |
| NEU3 | House keeper | 0.75 | NM_006656.5 | 1841-1940 | 12 | 67 | 122 |
| R3HDM1 | House keeper | 0.75 | NM_015361.2 | 1276-1375 | 13 | 68 | 123 |
| RANBP9 | House keeper | 0.75 | NM_005493.2 | 2001-2100 | 14 | 69 | 124 |
| RC3H2 | House keeper | 0.75 | NM_018835.2 | 2911-3010 | 15 | 70 | 125 |
| TRIM56 | House keeper | 0.75 | NM_030961.1 | 2571-2670 | 16 | 71 | 126 |
| UBXN4 | House keeper | 0.75 | NM_014607.3 | 344-443 | 17 | 72 | 127 |
| VAC14 | House keeper | 0.75 | NM_018052.3 | 1476-1575 | 18 | 73 | 128 |
| VRK3 | House keeper | 0.75 | NM_016440.3 | 821-920 | 19 | 74 | 129 |
| WAC | House keeper | 0.75 | NM_100486.2 | 756-855 | 20 | 75 | 130 |
| WDR55 | House keeper | 0.75 | NM_017706.4 | 816-915 | 21 | 76 | 131 |
| ZNF598 | House keeper | 0.75 | NM_178167.2 | 2369-2468 | 22 | 77 | 132 |
| CCNB2 | Proliferation | 6.01 | NM_004701.2 | 981-1080 | 23 | 78 | 133 |
| CDC20 | Proliferation | 6.35 | NM_001255.2 | 431-530 | 24 | 79 | 134 |
| CDKN3 | Proliferation | 6.4 | NM_005192.3 | 511-610 | 25 | 80 | 135 |
| E2F2 | Proliferation | 6.02 | NM_004091.2 | 3606-3705 | 26 | 81 | 136 |
| ESPL1 | Proliferation | 6.5 | NM_012291.4 | 1286-1385 | 27 | 82 | 137 |
| FAM83D | Proliferation | 5.92 | NM_030919.2 | 866-965 | 28 | 83 | 138 |
| FOXM1 | Proliferation | 6.55 | NM_021953.2 | 3209-3308 | 29 | 84 | 139 |
| H2AFX | Proliferation | 6.08 | NM_002105.2 | 1393-1492 | 30 | 85 | 140 |
| KIF2C | Proliferation | 6.19 | NM_006845.3 | 1941-2040 | 31 | 86 | 141 |
| MKI67 | Proliferation | 6.65 | NM_002417.2 | 4021-4120 | 32 | 87 | 142 |
| NCAPG | Proliferation | 6.44 | NM_022346.3 | 781-880 | 33 | 88 | 143 |
| TOP2A | Proliferation | 6.46 | NM_001067.2 | 5377-5476 | 34 | 89 | 144 |
| ZWINT | Proliferation | 5.41 | NM_007057.3 | 851-950 | 35 | 90 | 145; | and
  (d) determining a survival predictor score from the gene expression data, wherein the survival predictor score is determined by:
   (1) multiplying each signal value of each gene obtained in (c) by the corresponding coefficient value for the respective gene listed in the table in (c) to obtain a multiplication product for each gene, and
   (2) summing the multiplication products of each gene obtained in (d)(1).

12. The method of claim 11, wherein the survival predictor score is determined by the equation:

$$y = \sum_i c_i \cdot (x_i)$$

wherein y is the survival predictor score the summation is over the set of genes listed in the table in (c) with each gene in the set being represented by i, ci is the corresponding coefficient value for the respective gene i in the table in (c), and xi is the signal value for gene i.

13. The method of claim 11, wherein the RNA gene expression data is obtained using an assay comprising color-coded probes.

14. A method of predicting a survival outcome of a human subject having mantle cell lymphoma (MCL) comprising:
(a) determining a survival predictor score of the subject according to claim 11; and
(b) classifying the subject as belonging to one of the following groups based on the survival predictor score: (i) good prognosis, (ii) intermediate prognosis, and (iii) poor prognosis.

15. A method of selecting a treatment for a human subject having mantle cell lymphoma (MCL) comprising:
(a) predicting a survival outcome of the human subject having MCL according to claim 14; and
(b) selecting a treatment for the subject based on the subject's classification.

16. The method of claim 15, wherein the subject is classified as belonging to the group of (i) good prognosis wherein the survival predictor score is determined as less than about −100000.

17. The method of claim 15, wherein the subject is classified as belonging to the group of (iii) poor prognosis wherein the survival predictor score is determined as greater than about −32000.

18. The method of claim 15, wherein the treatment includes administration of R-CHOP (rituximab, cyclophosphamide, hydroxydaunorubicin, vincristine, and prednisone).

19. A method of treating a human subject having mantle cell lymphoma (MCL) comprising:
(a) selecting a treatment for the human subject having MCL according to claim 15; and
(b) treating the subject with (i) cyclophosphamide, hydroxydaunorubicin, vincristine, and prednisone, (ii) rituximab, (iii) BTK inhibitors, (iv) IMiDs, (v) mTor inhibitors, (vi) bendamustine, or (vii) any combination of (i)-(vi).

20. A method of predicting a survival outcome of a human subject having mantle cell lymphoma (MCL) comprising:
(a) determining a survival predictor score of the subject according to claim 11; and
(b) classifying the subject as belonging to one of the following groups based on the survival predictor score: (i) good prognosis wherein the survival predictor score is determined as less than about −100000, (ii) intermediate prognosis wherein the survival predictor score is determined as between about −100000 and about −32000, and (iii) poor prognosis wherein the survival predictor score is determined as greater than about −32000.

* * * * *